US010023865B2

(12) United States Patent
Tuschl et al.

(10) Patent No.: US 10,023,865 B2
(45) Date of Patent: *Jul. 17, 2018

(54) RNA-INTERFERENCE BY SINGLE-STRANDED RNA MOLECULES

(71) Applicant: Max-Planck-Gesellschaft zur Foerderung der Wissenschaften e.V., Munich (DE)

(72) Inventors: Thomas Tuschl, New York, NY (US); Javier Martinez, New York, NY (US); Agnieszka Patkaniowska, New York, NY (US); Henning Urlaub, Goettingen (DE); Reinhard Luehrmann, Marburg-Michelbach (DE)

(73) Assignee: Max-Planck-Gesellschaft zur Förderung de Wissenschaften e.V., München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/258,603

(22) Filed: Sep. 7, 2016

(65) Prior Publication Data

US 2017/0067050 A1     Mar. 9, 2017

Related U.S. Application Data

(60) Division of application No. 14/337,710, filed on Jul. 22, 2014, now Pat. No. 9,476,044, which is a continuation of application No. 13/329,710, filed on Dec. 19, 2011, now abandoned, which is a division of application No. 10/520,470, filed as application No. PCT/EP03/07516 on Jul. 10, 2003, now Pat. No. 8,101,348.

(30) Foreign Application Priority Data

Jul. 10, 2002  (EP) .................................. 02015532
Aug. 23, 2002  (EP) .................................. 02018906

(51) Int. Cl.
| | | |
|---|---|---|
| *C12N 15/11* | (2006.01) | |
| *C12N 15/113* | (2010.01) | |
| *C07K 14/47* | (2006.01) | |
| *C07K 19/00* | (2006.01) | |
| *A61K 47/54* | (2017.01) | |

(52) U.S. Cl.
CPC .......... *C12N 15/113* (2013.01); *A61K 47/549* (2017.08); *A61K 47/557* (2017.08); *C07K 14/4705* (2013.01); *C07K 19/00* (2013.01); *C12N 15/111* (2013.01); *C12N 2310/14* (2013.01); *C12N 2310/351* (2013.01); *C12N 2310/3513* (2013.01); *C12N 2320/30* (2013.01); *C12N 2320/51* (2013.01); *C12N 2330/30* (2013.01)

(58) Field of Classification Search
None
See application file for complete search history.

(56) References Cited

U.S. PATENT DOCUMENTS

| 4,469,863 A | 9/1984 | Ts'o et al. |
| 6,379,931 B1 * | 4/2002 | Rossi .................... C12N 15/113 435/6.14 |
| 2002/0150945 A1 | 10/2002 | Finney et al. |
| 2002/0162126 A1 * | 10/2002 | Beach .................... C12N 15/102 800/8 |
| 2003/0125281 A1 * | 7/2003 | Lewis ..................... A61K 31/58 514/44 A |
| 2003/0153521 A1 | 8/2003 | McSwiggen |
| 2003/0170891 A1 | 9/2003 | McSwiggen |
| 2004/0014108 A1 | 1/2004 | Eldrup et al. |
| 2004/0203145 A1 | 10/2004 | Zamore et al. |

OTHER PUBLICATIONS

Kuramochi-Miyagawa et al., Two mouse piwi-related genes: miwi and mili, 2001, Mechanisms of Development, vol. 108, pp. 121-133.*
Agrawal et al., "Antisense oligonucleotides as antiviral agents", Trends in Biotechnol., vol. 10, May 1992, pp. 152-158.
Chiu et al., RNAi in human cells: Basic structural and functional features of small interfering RNA, 2002, Molecular Cell, vol. 10, pp. 549-561.
Hamada et al., Effects on RNA interference in gene expression (RNAi) in cultured mammalian cells of mismatches and the introduction of chemical modifications at the 3' ends of siRNAs, 2002, Antisense and Nucleic Acid Drug Development, vol. 12, pp. 301-309.
Chiu et al., siRNA function in RNAi: A chemical modification analysis, 2003, RNA, vol. 9, pp. 1034-1048.
Hamilton et al., A species of small antisense RNA in post-transcriptional gene silencing in plants, 1999, Science, vol. 286. pp. 950-952.
Vaucheret et al., Post-transcriptional gene silencing in plants, Journal of Cell Science, vol. 114, pp. 3083-3091, 2001.
Bernstein et al., Role for a bidentate ribonuclease in the initiation step of RNA interference, Jan. 18, 2001, Nature, vol. 409, pp. 363-366.
Elbashir et al., Duplexes of 21-nucleotide RNAs mediate RNA interference in cultured mammalian cells, May 2001, Nature vol. 411, pp. 494-498.
Opalinska et al., Nucleic-acid therapeutics: Basic principles and recent applications, Jul. 2002, Nature Reviews Drug Discovery, vol. 1, pp. 503-514.
Charlie Schmidt, Negotiating the RNAi patent thicket, Mar. 2007, Nature Biotechnology, vol. 25, pp. 273-275.
Bernstein et al., "The rest is silence", RNA, 2001, vol. 7, pp. 1509-1521.

(Continued)

*Primary Examiner* — Dana H Shin
(74) *Attorney, Agent, or Firm* — Rothwell, Figg, Ernst & Manbeck, P.C.

(57) ABSTRACT

The present invention relates to sequence and structural features of single-stranded (ss)RNA molecules required to mediate target-specific nucleic acid modifications by RNA-interference (RNAi), such as target mRNA degradation and/or DNA methylation.

16 Claims, 26 Drawing Sheets

(56) References Cited

OTHER PUBLICATIONS

Caplen et al., "Rescue of polyglutamine-mediated cytotoxicity by double-stranded RNA-mediated RNA interference", Human Molecular Genetics, 2002, vol. 11, No. 2, pp. 175-184.
Canadian Office Action No. 2,489,174 dated May 28, 2010 (5 pages).
Schmitz et al., Effect of s'-0-methyl antisense ORNs on expression of thymidylate synthase in human colon cancer RKO cells, 2001, Nucleic Acids Research, vol. 29, pp. 415-422.
Tijsterman Marcel et al., "RNA helicase MUT-14-dependent gene silencing triggered in C.elegans by short antisense RNAs", Science vol. 295, No. 5555, Jan. 25, 2002, pp. 694-697.
Boutla A et al., "Short 5'-phosphorylated double-stranded RNAs induce RNA interference in *Drosophila*", Current Biology, Current Science, vol. 11, No. 22, Nov. 13, 2001, pp. 1776-1780.
Elbashir S M et al., "Analysis of gene function in somatic mammalian cells using small interfering RNAs", Methods: a Companion to Methods in Enzymology, vol. 26, No. 2, Feb. 2002, pp. 199-213.
Yu Jenn-Yah et al., "RNA interference by expression of short-interfering RNAs and hairpin RNAs in mammalian cells", Proceedings of the National Academy of Sciences of the United States, vol. 99, No. 9, Apr. 30, 2002, pp. 6047-6052.
Schwarz Dianne et al., "Evidence that siRNAs function as guides, not primers, in the *Drosophila* and human RNAi pathways", Molecular Cell, vol. 10, No. 3, Sep. 2002, pp. 537-548.
Hammond S M et al. "Argonaute2, a link between genetic and biochemical analyses of RNAi", Science, Aug. 10, 2001, LNKD-PubMed: 11498593 vol. 293,No. 5532, pp. 1146-1150, XP002183120.
Mourelatos Zissimos et al."miRNPs: a novel class of ribonucleoproteins containing numerous microRNAs", Genes & Development, Mar. 15, 2002, LNKD-PubMed: 11914277, vol. 16, No. 6, pp. 720-728, XP002619532.
Martinez Javler et al. "Single-stranded antisense siRNAs guide target RNA cleavage in RNAi", Cell, vol. 110, No. 5, Sep. 6, 2002, pp. 563-574, XP00225781.
Meister Gunter et al. Human Argonaute2 mediates RNA cleavage targeted by miRNAs and siRNAs, Molecular Cell, Jul. 23, 2004, LNKD-PubMed: 15260970, vol. 15, No. 2, pp. 185-197, XP002619534.
McManus Michael T et al. "Gene silencing using micro-RNA designed hairpins", RNA (New York) Jun. 2002, LNKD PubMed: 12088155, vol. 8, No. 6, pp. 842-850, XP008021481.
Paddison Patrick J et al. "Short hairpin RNAs (shRNAs) induce sequence-specific silencing in mammalian cells", Genes and Development, Apr. 15, 2002, LNKD-PubMed: 11959843, vol. 16, No. 8, pp. 948-958, XP002204653.
Van Den Berg Aden et al. "RISC—target interaction: cleavage and translational suppression", Blochimica et Biophysica Acta, LNKD-PubMed: 18692607, vol. 1779, No. 11,(2008), pp. 668-677, XP002619533.
Brummelkamp Thijn R et al. "A system for stable expression of short interfering RNAs in mammalian cells", Science (New York), Apr. 19, 2002, LNKD-PubMed: 11910072, pp. 550-553, XP002626048.
Zeng Yan et al. "Both natural and designed micro RNAs can inhibit the expression of cognate mRNAs when expressed in human cells", Molecular Cell, Jun. 2002, LNKD-PubMed: 12086629, vol. 9, No. 6, pp. 1327-1333, XP002296481.
Conklin Douglas S. "RNA-interference-based silencing of mammalian gene expression", ChemBiochem: A European Journal of Chemical Biology, Oct. 6, 2003, LNKD-PubMed: 14523921, vol. 4, No. 10, pp. 1033-1039, XP002623636.
Yoda et al., ATP-dependent human RISC assembly pathways, 2010, Nature Structural & Molecular Biology, vol. 17, pp. 17-24.
Lima et al., Single-stranded siRNAs activate RNAi in animals, 2012, Cell, vol. 150, pp. 883-894.

\* cited by examiner

Superdex 200 glycerol gradient 5-20%

Fig. 7 A
Fig. 7 B
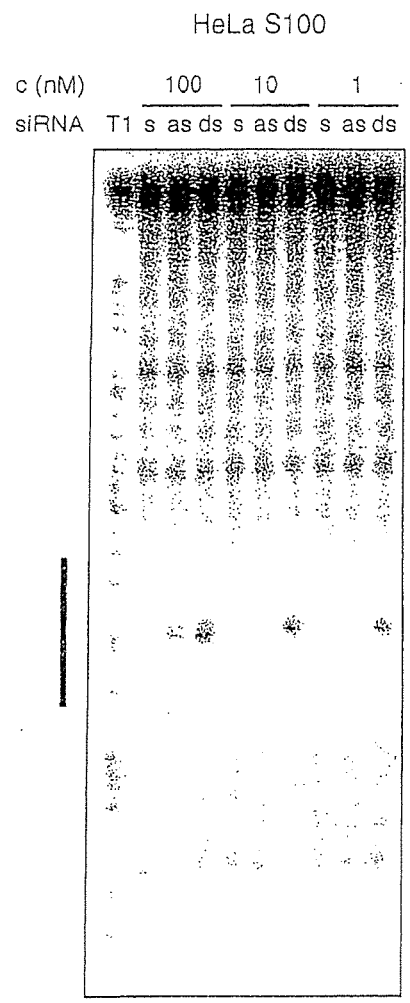
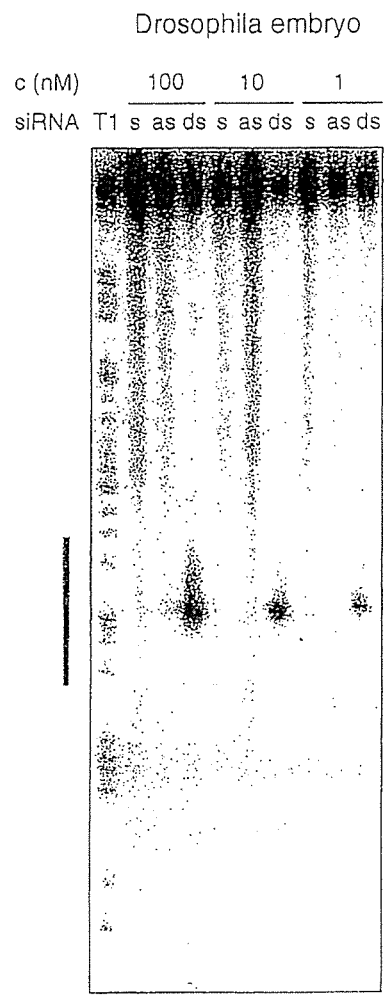

Fig. 13 A

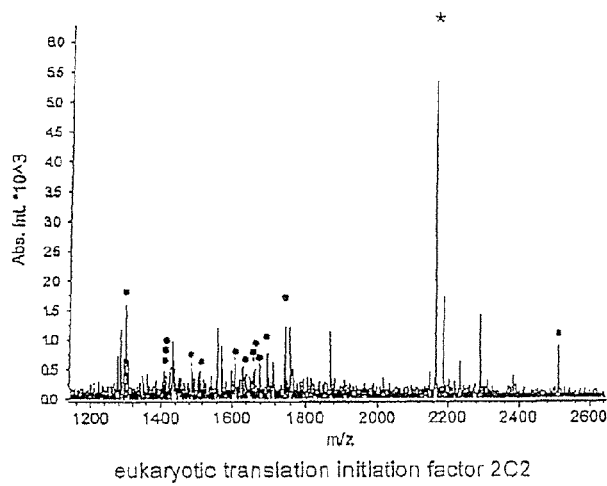

eukaryotic translation initiation factor 2C2

| Observed | Mr(expt) | Mr(calc) | Delta | Position | Miss | Peptide | |
|---|---|---|---|---|---|---|---|
| 1299.67 | 1298.67 | 1298.73 | -0.07 | 413 – 424 | 0 | VLQPPSILYGGR | [SEQ ID NO: 42] |
| 1402.64 | 1401.64 | 1401.74 | -0.10 | 637 – 648 | 0 | QEIIQDLAAMVR Oxidation (M) | [SEQ ID NO: 43] |
| 1413.62 | 1412.61 | 1412.73 | -0.12 | 169 – 180 | 1 | HLPSMRYTPVGR | [SEQ ID NO: 44] |
| 1423.60 | 1422.59 | 1422.71 | -0.12 | 356 – 367 | 1 | KLTDNQTSTMIR Oxidation (M) | [SEQ ID NO: 45] |
| 1486.56 | 1485.56 | 1485.66 | -0.10 | 495 – 507 | 0 | YAQGADSVEPMFR Oxidation (M) | [SEQ ID NO: 46] |
| 1513.71 | 1512.70 | 1512.80 | -0.10 | 112 – 125 | 1 | OKVELEVTLPGEGK | [SEQ ID NO: 47] |
| 1608.67 | 1607.66 | 1607.69 | -0.03 | 481 – 494 | 0 | DAGMPIQGQPCFCK | [SEQ ID NO: 48] |
| 1635.84 | 1634.83 | 1634.85 | -0.02 | 85 – 98 | 1 | TQIFGDRKFVFDGR | [SEQ ID NO: 49] |
| 1658.85 | 1657.85 | 1657.84 | 0.01 | 368 – 382 | 2 | AIARSAPDRQEEISK | [SEQ ID NO: 50] |
| 1663.85 | 1662.85 | 1662.91 | -0.06 | 698 – 711 | 1 | DYQPGITFIVVQKR | [SEQ ID NO: 51] |
| 1675.79 | 1674.78 | 1674.84 | -0.06 | 372 – 385 | 2 | SAPDRQEEISKLMR Oxidation (M) | [SEQ ID NO: 52] |
| 1696.77 | 1695.76 | 1695.84 | -0.08 | 323 – 336 | 0 | YPHLPCLQVGQEOK | [SEQ ID NO: 53] |
| 1743.75 | 1742.74 | 1742.77 | -0.03 | 181 – 197 | 0 | SFFTASEGCSHPLGGGR | [SEQ ID NO: 54] |
| 2511.07 | 2510.06 | 2510.12 | -0.05 | 816 – 838 | 1 | YELVDKEHDSAEGSHTSGQSNGR | [SEQ ID NO: 55] |

Fig. 13 B

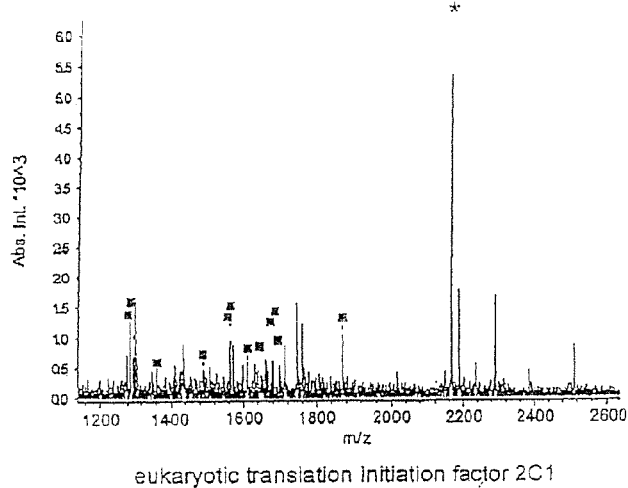

eukaryotic translation initiation factor 2C1

| Observed | Mr(expt) | Mr(calc) | Delta | Position | | Miss | Peptide | |
|---|---|---|---|---|---|---|---|---|
| 1283.66 | 1282.65 | 1282.74 | -0.09 | 410 – | 421 | 0 | VLPAPILQYGGR | [SEQ ID NO: 56] |
| 1294.65 | 1293.64 | 1293.67 | -0.03 | 794 – | 805 | 0 | SVSIPAPAYYAR | [SEQ ID NO: 57] |
| 1361.61 | 1360.60 | 1360.70 | -0.10 | 553 – | 564 | 0 | TSPQTLSNLCLK | [SEQ ID NO: 58] |
| 1486.56 | 1485.56 | 1485.66 | -0.10 | 492 – | 504 | 0 | YAQGADSVEPMTR Oxidation (M) | [SEQ ID NO: 59] |
| 1560.76 | 1559.75 | 1559.83 | -0.08 | 97 – | 110 | 0 | NIYTVTALPIGNER | [SEQ ID NO: 60] |
| 1561.76 | 1560.75 | 1560.78 | -0.02 | 111 – | 124 | 1 | VDFEVIIPGEGKDR | [SEQ ID NO: 61] |
| 1608.67 | 1607.66 | 1607.69 | -0.03 | 478 – | 491 | 0 | DAGMPIQGQPCFCK | [SEQ ID NO: 62] |
| 1640.71 | 1639.73 | 1639.82 | -0.08 | 240 – | 253 | 0 | NIDEQEKPLTDSQR | [SEQ ID NO: 63] |
| 1675.79 | 1674.78 | 1674.84 | -0.06 | 369 – | 382 | 2 | SAPDROEEISRLMK Oxidation (M) | [SEQ ID NO: 64] |
| 1679.86 | 1678.85 | 1678.90 | -0.05 | 695 – | 708 | 1 | DYQPGITYTVVQKR | [SEQ ID NO: 65] |
| 1696.77 | 1695.76 | 1695.84 | -0.08 | 320 – | 333 | 0 | YPRLPCLQVGQEQK | [SEQ ID NO: 66] |
| 1867.85 | 1866.85 | 1866.87 | -0.02 | 178 – | 194 | 0 | SFFSPPEGYYKPLGGSR | [SEQ ID NO: 67] |

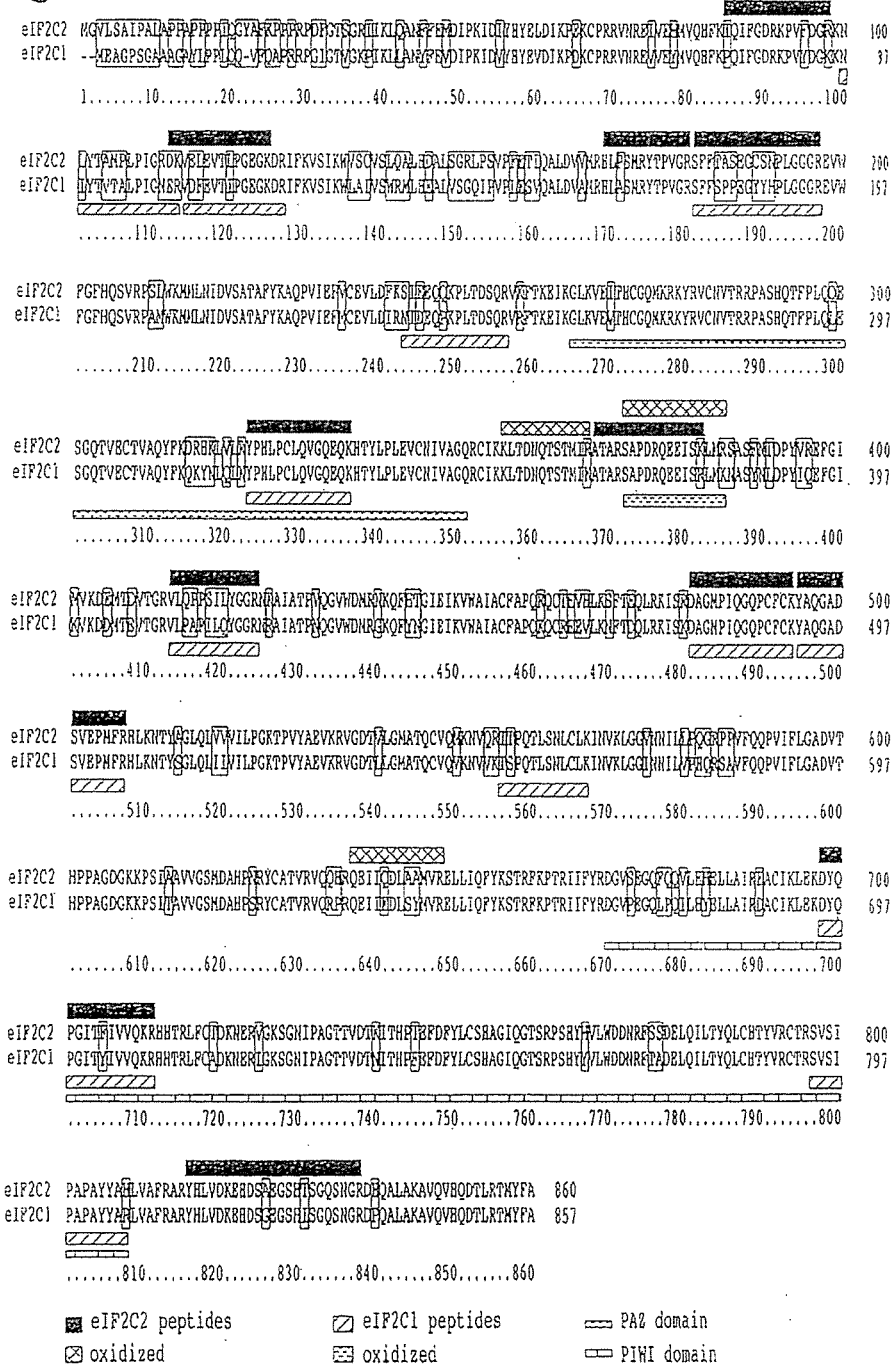

Fig. 14

>eIF2C1, predicted protein sequence
MEAGPSGAAAGAYLPPLQQVFQAPRRPGIGTVGKPIKLLANYFEVDIPKIDVYHYEVDIKPD
KCPRRVNREVVEYMVQHFKPQIFGDRKPVYDGKKNIYTVTALPIGNERVDFEVTIPGEGKDR
IFKVSIKWLAIVSWRMLHEALVSGQIPVPLESVQALDVAMRHLASMRYTPVGRSFFSPPEGY
YHPLGGGREVWFGFHQSVRPAMWKMMLNIDVSATAFYKAQPVIEFMCEVLDIRNIDEQPKPL
TDSQRVRFTKEIKGLKVEVTHCGQMKRKYRVCNVTRRPASHQTFPLQLESGQTVECTVAQYF
KQKYNLQLKYPHLPCLQVGQEQKHTYLPLEVCNIVAGQRCIKKLTDNQTSTMIKATARSAPD
RQEEISRLMKNASYNLDPYIQEFGIKVKDDMTEVTGRVLPAPILQYGGRNRAIATPNQGVWD
MRGKQFYNGIEIKVWAIACFAPQKQCREEVLKNFTDQLRKISKDAGMPIQGQPCFCKYAQGA
DSVEPMFRHLKNTYSGLQLIIVILPGKTPVYAEVKRVGDTLLGMATQCVQVKNVVKTSPQTL
SNLCLKINVKLGGINNILVPHQRSAVFQQPVIFLGADVTHPPAGDGKKPSITAVVGSMDAHP
SRYCATVRVQRPRQEIIEDLSYMVRELLIQFYKSTRFKPTRIIFYRDGVPEGQLPQILHYEL
LAIRDACIKLEKDYQPGITYIVVQKRHHTRLFCADKNERIGKSGNIPAGTTVDTNITHPFEF
DFYLCSHAGIQGTSRPSHYYVLWDDNRFTADELQILTYQLCHTYVRCTRSVSIPAPAYYARL
VAFRARYHLVDKEHDSGEGSHISGQSNGRDPQALAKAVQVHQDTLRTMYFA >eIF2C2, predicted protein sequence
MGVLSAIPALAPPAPPPPIQGYAFKPPPRPDFGTSGRTIKLQANFFEMDIPKIDIYHYELDI
KPEKCPRRVNREIVEHMVQHFKTQIFGDRKPVFDGRKNLYTAMPLPIGRDKVELEVTLPGEG
KDRIFKVSIKWVSCVSLQALHDALSGRLPSVPFETIQALDVVMRHLPSMRYTPVGRSFFTAS
EGCSNPLGGGREVWFGFHQSVRPSLWKMMLNIDVSATAFYKAQPVIEFVCEVLDFKSIEEQQ
KPLTDSQRVKFTKEIKGLKVEITHCGQMKRKYRVCNVTRRPASHQTFPLQQESGQTVECTVA
QYFKDRHKLVLRYPHLPCLQVGQEQKHTYLPLEVCNIVAGQRCIKKLTDNQTSTMIRATARS
APDRQEEISKLMRSASFNTDPYVREFGIMVKDEMTDVTGRVLQPPSILYGGRNKAIATPVQG
VWDMRNKQFHTGIEIKVWAIACFAPQRQCTEVHLKSFTEQLRKISRDAGMPIQGQPCFCKYA
QGADSVEPMFRHLKNTYAGLQLVVVILPGKTPVYAEVKRVGDTVLGMATQCVQMKNVQRTTP
QTLSNLCLKINVKLGGVNNILLPQGRPPVFQQPVIFLGADVTHPPAGDGKKPSIAAVVGSMD
AHPNRYCATVRVQQHRQEIIQDLAAMVRELLIQFYKSTRFKPTRIIFYRDGVSEGQFQQVLH
HELLAIREACIKLEKDYQPGITFIVVQKRHHTRLFCTDKNERVGKSGNIPAGTTVDTKITHP
TEFDFYLCSHAGIQGTSRPSHYHVLWDDNRFSSDELQILTYQLCHTYVRCTRSVSIPAPAYY
AHLVAFRARYHLVDKEHDSAEGSHTSGQSNGRDHQALAKAVQVHQDTLRTMYFA >eIF2C3, predicted protein sequence
SRSRVPVPGPGAAAAPCPAPASPRRHPSANIPEIKRYAAAAAAAAGPGAGGAGDRGEAAPAA
AMEALGPGPPASLFQPPRRPGLGTVGKPIRLLANHFQVQIPKIDVYHYDVDIKPEKRPRRVN
REVVDTMVRHFKMQIFGDRQPGYDGKRNMYTAHPLPIGRDRVDMEVTLPGEGKDQTFKVSVQ
WVSVVSLQLLLEALAGHLNEVPDDSVQALDVITRHLPSMRYTPVGRSFFSPPEGYYHPLGGG
REVWFGFHQSVRPAMWNMMLNIDVSATAFYRAQPIIEFMCEVLDIQNINEQTKPLTDSQRVK
FTKEIRGLKVEVTHCGQMKRKYRVCNVTRRPASHQTFPLQLENGQAMECTVAQYFKQKYSLQ
LKYPHLPCLQVGQEQKHTYLPLEVCNIVAGQRCIKKLTDNQTSTMIKATARSAPDRQEEISR
LVKSNSMVGGPDPYLKEFGIVVHNEMTELTGRVLPAPMLQYGGRNKTVATPNQGVWDMRGKQ
FYAGIEIKVWAVACFAPQKQCREDLLKSFTDQLRKISKDAGMPIQGQPCFCKYAQGADSVEP
MPKHLKMTYVGLQLIVVILPGKTPVYAEVKRVGDTLLGMATQCVQVKNVVKTSPQTLSNLCL
KINAKLGGINNVLVPHQRPSVFQQPVIFLGADVTHPPAGDGKKPSIAAVVGSMDGHPSRYCA
TVRVQTSRQEISQELLYSQEVIQDLTNMVRELLIQFYKSTRFKPTRIIYYRGGVSEGQMKQV
AWPELIAIRKACISLEEDYRPGITYIVVQKRHHTRLFCADKTERVGKSGNVPAGTTVDSTIT
HPSEFDFYLCSHAGIQGTSRPSHYQVLWDDNCFTADELQLLTYQLCHTYVRCTRSVSIPAPA
YYARLVAFRARYHLVDKDHDSAEGSHVSGQSNGRDPQALAKAVQIHHDTQHTMYFA

Fig. 14 (Con.)

```
>eIF2C4, predicted protein sequence
AGPAGAQPLLMVPRRPGYGTMGKPIKLLANCFQVEIPKIDVYLYEVDIKPDKCPRRVNREVV
DSMVQHFKVTIFGDRRPVYDGKRSLYTANPLPVATTGVDLDVTLPGEGGKDRPFKVSIKFVS
RVSWHLLHEVLTGRTLPEPLELDKPISTNPVHAVDVVLRHLPSMKYTPVGRSFFSAPEGYDH
PLGGGREVWFGFHQSVRPAMWKMMLNIDVSATAFYKAQPVIQFMCEVLDIHNIDEQPRPLTD
SHRVKFTKEIKGLKVEVTHCGTMRRKYRVCNVTRRPASHQTFPLQLENGQTVERTVAQYFRE
KYTLQLKYPHLPCLQVGQEQKHTYLPLEVCNIVAGQRCIKKLTDNQTSTMIKATARSAPDRQ
EEISRLVRSANYETDPFVQEFQFKVRDEMAHVTGRVLPAPMLQYGGRNRTVATPSHGVWDMR
GKQFHTGVEIKMWAIACFATQRQCREEILKGFTDQLRKISKDAGMPIQGQPCFCKYAQGADS
VEPMFRHLKNTYSGLQLIIVILPGKTPVYAEVKRVGDTLLGMATQCVQVKNVIKTSPQTLSN
LCLKINVKLGGINNILVPHQRPSVFQQPVIFLGADVTHPPAGDGKKPSIAAVVGSMDAHPSR
YCATVRVQRPRQEIIQDLASMVRELLIQFYKSTRFKPTRIIFYRDGVSEGQFRQVLYYELLA
IREACISLEKDYQPGITYIVVQKRHHTRLFCADRTERVGRSGNIPAGTTVDTDITHPYEFDF
YLCSHAGIQGTSRPSHYHVLWDDNCFTADELQLLTYQLCHTYVRCTRSVSIPAPAYYAHLVA
FRARYHLVDKEHDSAEGSHVSGQSNGRDPQALAKAVQIHQDTLRTMYFA >HILI, predicted protein sequence
ISSGDAGSTFMERGVKNKQDFMDLSICTREKLAHVRNCKTGSSGIPVKLVTNLFNLDFPQDW
QLYQYHVTYIPDLASRRLRIALLYSHSELSNKAKAFDGAILFLSQKLEEKVTELSSETQRGE
TIKMTITLKRELPSSSPVCIQVFNIIFRKILKKLSMYQIGRNFYNPSEPMEIPQHKLSLWPG
FAISVSYFERKLLFSADVSYKVLRNETVLEFMTALCQRTGLSCFTQTCEKQLIGLIVLTRYN
NRTYSIDDIDWSVKPTHTFQKRDGTEITYVDYYKQQYDITVSDLNQPMLVSLLKKKRNDNSE
AQLAHLIPELCFLTGLTDQATSDFQLMKAVAEKTRLSPSGRQQRLARLVDNIQRNTNARFEL
ETWGLHFGSQISLTGRIVPSEKILMQDHICQPVSAADWSKDIRTCKILNAQSLNTWLILCSD
RTEYVAESFLNCLRRVAGSMGFNVMCILPSNQKTYYDSIKKYLSSDCPVPSQCVLARTLNKQ
GMMMSIATKIAMQMTCKLGGELWAVEIPLKSLMVVGIDVCKDALSKDVMVVGCVASVNPRIT
RWFSRCILQRTMTDVADCLKVFMTGALNKWYKYNHDLPARIIVYRAGVGDGQLKTLIEYEVP
QLLSSVAESSSNTSSRLSVIVVRKKCMPRFFTEMNRTVQNPPLGTVVDSEATRNEWQYDFYL
ISQVACRGTVSPTYYNVIYDDNGLKPDHMQRLTFKLCHLYYNWPGIVSVPAPCQYAHKLTFL
VAQSIHKEPSLELANHLFYL >HIWI, predicted protein sequence
MTGRARARARGRARGQETAQLVGSTASQQPGYIQPRPQPPPAEGELFGRGRQRGTAGGTAKS
QGLQISAGFQELSLAERGGRRRDFHDLGVNTRQNLDHVKESKTGSSGIIVRLSTNHFRLTSR
PQWALYQYHIDYNPLMEARRLRSALLFQHEDLIGKCHAFDGTILFLPKRLQQKVTEVFSKTR
NGEDVRITITLTNELPPTSPTCLQFYNIIFRRLLKIMNLQQIGRNYYNPNDPIDIPSHRLVI
WPGFTTSILQYENSIMLCTDVSHKVLRSETVLDFMFNFYHQTEEHKFQEQVSKELIGLVVLT
KYNNKTYRVDDIDWDQNPKSTFKKADGSEVSFLEYYRKQYNQEITDLKQPVLVSQPKRRRGP
GGTLPGPAMLIPELCYLTGLTDKMRNDFNVMKDLAVHTRLTPEQRQREVGRLIDYIHKNDNV
QRELRDWGLSFDSNLLSFSGRILQTEKIHQGGKTFDYNPQFADWSKETRGAPLISVKPLDNW
LLIYTRRNYEAANSLIQNLFKVTPAMGMQMRKAIMIEVDDRTEAYLRVLQQKVTADTQIVVC
LLSSNRKDKYDAIKKYLCTDCPTPSQCVVARTLGKQQTVMAIATKIALQMNCKMGGELWRVD
IPLKLVMIVGIDCYHDMTAGRRSIAGFVASINEGMTRWFSRCIFQDRGQELVDGLKVCLQAA
LRAWNSCNEYMPSRIIVYRDGVGDGQLKTLVNYEVPQFLDCLKSIGRGYNPRLTVIVVKKRV
NTRFFAQSGGRLQNPLPGTVIDVEVTRPEWYDFFIVSQAVRSGSVSPTHYNVIYDNSGLKPD
HIQRLTYKLCHIYYNWPGVIRVPAPCQYAHKLAFLVGQSIHREPNLSLSNRLYYL
```

```
>eIF2C1, cDNA sequence of predicted ORF
ATGGAAGCGGGACCCTCGGGAGCAGCTGCGGGCGCTTACCTGCCCCCCCTGCAGCAGGTGTT
CCAGGCACCTCGCCGGCCTGGCATTGGCACTGTGGGGAAACCAATCAAGCTCCTGGCCAATT
ACTTTGAGGTGGACATCCCTAAGATCGACGTGTACCACTACGAGGTGGACATCAAGCCGGAT
AAGTGTCCCCGTAGAGTCAACCGGGAAGTGGTGGAATACATGGTCCAGCATTTCAAGCCTCA
GATCTTTGGTGATCGCAAGCCTGTGTATGATGGAAAGAAGAACATTTACACTGTCACAGCAC
TGCCCATTGGCAACGAACGGGTCGACTTTGAGGTGACAATCCCTGGGGAAGGGAAGGATCGA
ATCTTTAAGGTCTCCATCAAGTGGCTAGCCATTGTGAGCTGGCGAATGCTGCATGAGGCCCT
GGTCAGCGGCCAGATCCCTGTTCCCTTGGAGTCTGTGCAAGCCCTGGATGTGGCCATGAGGC
ACCTGGCATCCATGAGGTACACCCCTGTGGGCCGCTCCTTCTTCTCACCGCCTGAGGGCTAC
TACCACCCGCTGGGGGGTGGGCGCGAGGTCTGGTTCGGCTTTCACCAGTCTGTGCGCCCTGC
CATGTGGAAGATGATGCTCAACATTGATGTCTCAGCCACTGCCTTTTATAAGGCACAGCCAG
TGATTGAGTTCATGTGTGAGGTGCTGGACATCAGGAACATAGATGAGCAGCCCAAGCCCCTC
ACGGACTCTCAGCGCGTTCGCTTCACCAAGGAGATCAAGGGCCTGAAGGTGGAAGTCACCCA
CTGTGGACAGATGAAGAGGAAGTACCGCGTGTGTAATGTTACCCGTCGCCCTGCTAGCCATC
AGACATTCCCCTTACAGCTGGAGAGTGGACAGACTGTGGAGTGCACAGTGGCACAGTATTTC
AAGCAGAAATATAACCTTCAGCTCAAGTATCCCCATCTGCCCTGCCTACAAGTTGGCCAGGA
ACAAAAGCATACCTACCTTCCCCTAGAGGTCTGTAACATTGTGGCTGGGCAGCGCTGTATTA
AAAAGCTGACCGACAACCAGACCTCGACCATGATAAAGGCCACAGCTAGATCCGCTCCAGAC
AGACAGGAGGAGATCAGTCGCCTGATGAAGAATGCCAGCTACAACTTAGATCCCTACATCCA
GGAATTTGGGATCAAAGTGAAGGATGACATGACGGAGGTGACAGGGCGAGTGCTGCCGGCGC
CCATCTTGCAGTACGGCGGCCGGAACCGGGCCATTGCCACACCCAATCAGGGTGTCTGGGAC
ATGCGGGGGAAACAGTTCTACAATGGGATTGAGATCAAAGTCTGGGCCATCGCCTGCTTCGC
ACCCCAAAAACAGTGTCGAGAAGAGGTGCTCAAGAACTTCACAGACCAGCTGCGGAAGATTT
CCAAGGATGCGGGGATGCCTATCCAGGGTCAACCTTGTTTCTGCAAATATGCACAGGGGGCA
GACAGCGTGGAGCCTATGTTCCGGCATCTCAAGAACACCTACTCAGGGCTGCAGCTCATTAT
TGTCATCCTGCCAGGGAAGACGCCGGTGTATGCTGAGGTGAAACGTGTCGGAGATACACTCT
TGGGAATGGCTACGCAGTGTGTGCAGGTGAAGAACGTGGTCAAGACCTCACCTCAGACTCTG
TCCAACCTCTGCCTCAAGATCAATGTCAAACTTGGTGGCATTAACAACATCCTAGTCCCACA
CCAGCGCTCTGCCGTTTTTCAACAGCCAGTGATATTCCTGGGAGCAGATGTTACACACCCCC
CAGCAGGGGATGGGAAAAAACCTTCTATCACAGCAGTGGTAGGCAGTATGGATGCCCACCCC
AGCCGATACTGTGCTACTGTGCGGGTACAGCGACCACGGCAAGAGATCATTGAAGACTTGTC
CTACATGGTGCGTGAGCTCCTCATCCAATTCTACAAGTCCACCCGTTTCAAGCCTACCCGCA
TCATCTTCTACCGAGATGGGGTGCCTGAAGGCAGCTACCCCAGATACTCCACTATGAGCTA
CTGGCCATTCGTGATGCCTGCATCAAACTGGAAAAGGACTACCAGCCTGGGATCACTTATAT
TGTGGTGCAGAAACGCCATCACACACCCGCCTTTTCTGTGCTGACAAGAATGAGCGAATTGGGA
AGAGTGGTAACATCCCAGCTGGGACCACAGTGGACACCAACATCACCCACCCATTTGAGTTT
GACTTCTATCTGTGCAGCCACGCAGGCATCCAGGGCACCAGCCGACCATCCCATTACTATGT
TCTTTGGGATGACAACCGTTTCACAGCAGATGAGCTCCAGATCCTGACGTACCAGCTGTGCC
ACACTTACGTACGATGCACACGCTCTGTCTCTATCCCAGCACCTGCCTACTATGCCCGCCTG
GTGGCTTTCCGGGCACGATACCACCTGGTGGACAAGGAGCATGACAGTGGAGAGGGGAGCCA
CATATCGGGGCAGAGCAATGGGCGGGACCCCCAGGCCCTGGCCAAAGCCGTGCAGGTTCACC
AGGATACTCTGCGCACCATGTACTTCGCT
```

Fig. 16 (con.)

```
>eIF2C2, cDNA sequence of predicted ORF
ATGGGTGTTCTCTCTGCCATTCCCGCACTTGCACCTCCTGCGCCGCCGCCCCCCATCCAAGG
ATATGCCTTCAAGCCTCCACCTAGACCCGACTTTGGGACCTCCGGGAGAACAATCAAATTAC
AGGCCAATTTCTTCGAAATGGACATCCCCAAAATTGACATCTATCATTATGAATTGGATATC
AAGCCAGAGAAGTGCCCGAGGAGAGTTAACAGGGAAATCGTGGAACACATGGTCCAGCACTT
TAAAACACAGATCTTTGGGGATCGGAAGCCCGTGTTTGACGGCAGGAAGAATCTATACACAG
CCATGCCCCTTCCGATTGGGAGGGACAAGGTGGAGCTGGAGGTCACGCTGCCAGGAGAAGGC
AAGGATCGCATCTTCAAGGTGTCCATCAAGTGGGTGTCCTGCGTGAGCTTGCAGGCGTTACA
CGATGCACTTTCAGGGCGGCTGCCCAGCGTCCCTTTTGAGACGATCCAGGCCCTGGACGTGG
TCATGAGGCACTTGCCATCCATGAGGTACACCCCGTGGGCCGCTCCTTCTTCACCGCGTCC
GAAGGCTGCTCTAACCCTCTTGGCGGGGGCCGAGAAGTGTGGTTTGGCTTCCATCAGTCCGT
CCGGCCTTCTCTCTGGAAAATGATGCTGAATATTGATGTGTCAGCAACAGCGTTTTACAAGG
CACAGCCAGTAATCGAGTTTGTTTGTGAAGTTTTGGATTTTAAAAGTATTGAAGAACAACAA
AAACCTCTGACAGATTCCCAAAGGGTAAAGTTTACCAAAGAAATTAAAGGTCTAAAGGTGGA
GATAACGCACTGTGGGCAGATGAAGAGGAAGTACCGTGTCTGCAATGTGACCCGGCGGCCCG
CCAGTCACCAAACATTCCCGCTGCAGCAGGAGAGCGGGCAGACGGTGGAGTGCACGGTGGCC
CAGTATTTCAAGGACAGGCACAAGTTGGTTCTGCGCTACCCCCACCTCCCATGTTTACAAGT
CGGACAGGAGCAGAAACACACCTACCTTCCCCTGGAGGTCTGTAACATTGTGGCAGGACAAA
GATGTATTAAAAAATTAACGGACAATCAGACCTCAACCATGATCAGAGCAACTGCTAGGTCG
GCGCCCGATCGGCAAGAAGAGATTAGCAAATTGATGCGAAGTGCAAGTTTCAACACAGATCC
ATACGTCCGTGAATTTGGAATCATGGTCAAAGATGAGATGACAGACGTGACTGGGCGGGTGC
TGCAGCCGCCCTCCATCCTCTACGGGGGCAGGAATAAAGCTATTGCGACCCCTGTCCAGGGC
GTCTGGGACATGCGGAACAAGCAGTTCCACACGGGCATCGAGATCAAGGTGTGGGCCATTGC
GTGCTTCGCCCCCCAGCGCCAGTGCACGGAAGTCCATCTGAAGTCCTTCACAGAGCAGCTCA
GAAAGATCTCGAGAGACGCTGGCATGCCCATCCAGGGCCAGCCGTGCTTCTGCAAATACGCG
CAGGGGGCGGACAGCGTGGAGCCCATGTTCCGGCACCTGAAGAACACGTATGCGGGCCTGCA
GCTGGTGGTGGTCATCCTGCCCGGCAAGACGCCCGTGTACGCCGAGGTCAAGCGCGTGGGAG
ACACGGTGCTGGGGATGGCCACGCAGTGCGTGCAGATGAAGAACGTGCAGAGGACCACGCCA
CAGACCCTGTCCAACCTTTGCCTGAAGATCAACGTCAAGCTGGGAGGCGTGAACAACATCCT
GCTGCCCCAGGGCAGGCCGCCGGTGTTCCAGCAGCCCGTCATCTTTCTGGGAGCAGACGTCA
CTCACCCCCCGCCGGGGATGGGAAGAAGCCCTCCATTGCCGCCGTGGTGGGCAGCAGCATGGAC
GCCCACCCCAATCGCTACTGCGCCACCGTGCGCGTGCAGCAGCACCGGCAGGAGATCATACA
AGACCTGGCCGCCATGGTCCGCGAGCTCCTCATCCAGTTCTACAAGTCCACGCGCTTCAAGC
CCACCCGCATCATCTTCTACCGCGACGGTGTCTCTGAAGGCCAGTTCCAGCAGGTTCTCCAC
CACGAGTTGCTGGCCATCCGTGAGGCCTGTATCAAGCTAGAAAAAGACTACCAGCCCGGGAT
CACCTTCATCGTGGTGCAGAAGAGGCACCACACCCGGCTCTTCTGCACTGACAAGAACGAGC
GGGTTGGGAAAAGTGGAAACATTCCAGCAGGCACGACTGTGGACACGAAAATCACCCACCCC
ACCGAGTTCGACTTCTACCTGTGTAGTCACGCTGGCATCCAGGGGACAAGCAGGCCTTCGCA
CTATCACGTCCTCTGGGACGACAATCGTTTCTCCTCTGATGAGCTGCAGATCCTAACCTACC
AGCTGTGTCACACCTACGTGCGCTGCACACGCTCCGTGTCCATCCCAGCGCCAGCATACTAC
GCTCACCTGGTGGCCTTCCGGGCAGGTACCACCTGGTGGATAAGGAACATGACAGTGCTGA
AGGAAGCCATACCTCTGGGCAGAGTAACGGGCGAGACCACCAAGCACTGGCCAAGGCGGTCC
AGGTTCACCAAGACACTCTGCGCACCATGTACTTTGCT
```

Fig. 16 (con.)

```
>eIF2C3, cDNA sequence of predicted ORF
AGCCGGAGCCGGGTCCCTGTCCCCGGGCCGGGCGCCGCCGCCGCCCCCTGCCCAGCGCCCGC
GTCTCCGCGGCGCCACCCCAGCGCCAATATTCCGGAGATCAAGCGTTACGCGGCGGCGGCGG
CGGCGGCGGCGGGGCCCGGAGCGGGAGGCGCCGGGGACCGGGGCGAGGCGGCCCCCGCCGCC
GCCATGGAGGCGCTGGGACCCGGACCTCCGGCTAGCCTGTTTCAGCCACCTCGTCGTCCTGG
CCTTGGAACTGTTGGAAAACCAATTCGACTGTTAGCCAATCATTTTCAGGTTCAGATTCCTA
AAATAGATGTGTATCACTATGATGTGGATATTAAGCCTGAAAAACGGCCTCGTAGAGTCAAC
AGGGAGGTAGTAGATACAATGGTGCGGCACTTCAAGATGCAAATATTTGGTGATCGGCAGCC
TGGGTATGATGGCAAAAGAAACATGTACACAGCACATCCACTACCAATTGGACGGGATAGGG
TTGATATGGAGGTGACTCTTCCAGGCGAGGGTAAAGACCAAACATTTAAAGTGTCTGTTCAG
TGGGTGTCAGTTGTGAGCCTTCAGTTGCTTTTAGAAGCTTTGGCTGGGCACTTGAATGAAGT
CCCAGATGACTCAGTACAAGCACTTGATGTTATCACAAGCACCTTCCCTCCATGAGGTACA
CCCCAGTGGGCCGTTCCTTTTTCTCACCCCCGGAAGGTTACTACCACCCTCTGGGAGGGGGC
AGGGAGGTCTGGTTTGGTTTTCATCAGTCTGTGAGACCTGCCATGTGGAATATGATGCTCAA
CATTGATGTATCTGCAACTGCTTTCTACCGGGCTCAGCCTATCATTGAGTTCATGTGTGAGG
TTTTAGACATTCAGAACATCAATGAACAGACCAAACCTCTAACAGACTCCCAGCGTGTCAAA
TTTACCAAAGAAATCAGAGGTCTCAAAGTTGAGGTGACCCACTGTGGACAGATGAAACGAAA
ATACCGAGTTTGTAATGTGACTAGACGGCCAGCCAGTCATCAAACTTTTCCTTTGCAGCTAG
AAAACGGTCAAGCTATGGAATGTACAGTAGCTCAATATTTTAAGCAAAAGTATAGTCTGCAA
CTGAAATACCCCCATCTTCCCTGTCTCCAAGTGGGACAAGAACAAAAGCATACATACTTGCC
ACTCGAGGTCTGTAATATAGTGGCAGGACAGCGATGTATCAAGAAGCTCACAGACAATCAGA
CTTCCACAATGATCAAAGCTACAGCAAGATCTGCTCCTGACAGACAGGAAGAGATCAGTAGA
CTGGTGAAGAGCAACAGTATGGTGGGTGGACCTGATCCATACCTTAAAGAATTTGGTATTGT
TGTCCACAATGAAATGACAGAGCTCACAGGCAGGGTACTTCCAGCACCAATGCTGCAATATG
GAGGCCGGAATAAAACAGTAGCCACACCCAACCAGGGTGTCTGGGACATGCGAGGAAAGCAG
TTTTATGCTGGCATTGAAATTAAAGTTTGGGCAGTTGCTTGTTTTGCACCTCAGAAACAATG
TAGGGAAGATTTACTAAAGAGTTTCACTGACCAGCTGCGTAAAATCTCTAAGGATGCAGGAA
TGCCCATCCAGGGTCAGCCATGTTTCTGCAAGTATGCACAAGGTGCAGACAGTGTGGAGCCT
ATGTTTAAACATCTGAAATGACTTATGTGGGCCTACAGCTAATAGTGGTTATCCTGCCTGG
AAAGACACCAGTATATGCGGAGGTGAAACGTGTTGGAGATACCCTTCTAGGTATGGCCACAC
AGTGTGTCCAGGTAAAAATGTAGTGAAGACCTCACCTCAAACCCTTTCCAATCTTTGCCTG
AAGATAAATGCAAAACTTGGAGGAATTAACAATGTGCTTGTGCCTCATCAAAGGCCCTCGGT
GTTCCAGCAGCCTGTCATCTTCCTGGGAGCGGATGTCACACACCCCCAGCAGGGGATGGGA
AGAAACCTTCCATTGCTGCTGTGGTTGGCAGTATGGATGCCCACCCCAGCCGGTACTGTGCC
ACCGTTCGGGTGCAGACTTCCCGGCAGGAGATCTCCCAAGAGCTCCTCTACAGTCAAGAGGT
CATCCAGGACCTGACTAACATGGTTCGAGAGCTGCTGATTCAGTTCTACAAATCCACACGCT
TCAAACCCACTCGGATCATCTATTACCGTGGAGGGGTATCTGAGGGACAAATGAAACAGGTA
GCTTGGCCAGAACTAATAGCAATTCGAAAGGCATGTATTAGCTTGGAAGAAGATTACCGGCC
AGGAATAACTTATATTGTGGTGCAAAAAAGACATCACACACGACTCTTCTGTGCAGATAAAA
CAGAAAGGGTAGGGAAAAGTGGCAATGTACCAGCAGGCACTACAGTGGATAGTACCATCACA
CATCCATCTGAGTTTGACTTTTACCTCTGTAGTCATGCAGGAATTCAGGGAACCAGCCGTCC
CTCACATTACCAGGTCTTGTGGGATGACAACTGCTTCACTGCAGATGAACTCCAGCTACTGA
CTTACCAGCTGTGTCACACCTATGTGAGGTGCACTCGCTCAGTCTCTATTCCAGCCCCTGCA
TATTATGCCCGGCTTGTAGCATTTAGGGCAAGGTATCATCTGGTGGATAAAGATCATGACAG
TGCGGAAGGCAGTCATGTGTCAGGACAGAGCAACGGCCGGGATCCTCAGGCCTTGGCTAAGG
CTGTGCAAATCCACCATGATACCCAGCACACGATGTATTTTGCC
```

Fig. 16 (con.)

```
>eIF2C4, cDNA sequence of predicted ORF
GCAGGACCCGCTGGGGCCCAGCCCCTACTCATGGTGCCCAGAAGACCTGGCTATGGCACCAT
GGGCAAACCCATTAAACTGCTGGCTAACTGTTTTCAAGTTGAAATCCCAAAGATTGATGTCT
ACCTCTATGAGGTAGATATTAAACCAGACAAGTGTCCTAGGAGAGTGAACAGGGAGGTGGTT
GACTCAATGGTTCAGCATTTTAAAGTAACTATATTTGGAGACCGTAGACCAGTTTATGATGG
AAAAAGAAGTCTTTACACCGCCAATCCACTTCCTGTGGCAACTACAGGGGTAGATTTAGACG
TTACTTTACCTGGGGAAGGTGGAAAAGATCGACCTTTCAAGGTGTCAATCAAATTTGTCTCT
CGGGTGAGTTGGCACCTACTGCATGAAGTACTGACAGGACGGACCTTGCCTGAGCCACTGGA
ATTAGACAAGCCAATCAGCACTAACCCTGTCCATGCCGTTGATGTGGTGCTACGACATCTGC
CCTCCATGAAATACACACCTGTGGGGCGTTCATTTTTCTCCGCTCCAGAAGGATATGACCAC
CCTCTGGGAGGGGGCAGGGAAGTGTGGTTTGGATTCCATCAGTCTGTTCGGCCTGCCATGTG
GAAAATGATGCTTAATATCGATGTTTCTGCCACTGCCTTCTACAAAGCACAACCTGTAATTC
AGTTCATGTGTGAAGTTCTTGATATTCATAATATTGATGAGCAACCAAGACCTCTGACTGAT
TCTCATCGGGTAAAATTCACCAAAGAGATAAAAGGTTTGAAGGTTGAAGTGACTCATTGTGG
AACAATGAGACGGAAATACCGTGTTTGTAATGTAACAAGGAGGCCTGCCAGTCATCAAACCT
TTCCTTTACAGTTAGAAAACGGCCAAACTGTGGAGAGAACAGTAGCGCAGTATTTCAGAGAA
AAGTATACTCTTCAGCTGAAGTACCCGCACCTTCCCTGTCTGCAAGTCGGGCAGGAACAGAA
ACACACCTACCTGCCACTAGAAGTCTGTAATATTGTGGCAGGGCAACGATGTATCAAGAAGC
TAACAGACAATCAGACTTCCACTATGATCAAGGCAACAGCAAGATCTGCACCAGATAGACAA
GAGGAAATTAGCAGATTGGTAAGAAGTGCAAATTATGAAACAGATCCATTTGTTCAGGAGTT
TCAATTTAAAGTTCGGGATGAAATGGCTCATGTAACTGGACGCGTACTTCCAGCACCTATGC
TCCAGTATGCAGGACGGAATCGGACAGTAGCAACACCGAGCCATGGAGTATGGACATGCGA
GGGAAACAATTCCACACAGGAGTTGAAATCAAAATGTGGGCTATCGCTTGTTTTGCCACACA
GAGGCAGTGCAGAGAAGAAATATTGAAGGGTTTCACAGACCAGCTGCGTAAGATTTCTAAGG
ATGCAGGGATGCCCATCCAGGGCCAGCCATGCTTCTGCAAATATGCACAGGGGGCAGACAGC
GTAGAGCCCATGTTCCGGCATCTCAAGAACACATATTCTGCCTACAGCTTATTATCGTCAT
CCTGCCGGGGAAGACACCAGTGTATGCGGAAGTGAAACGTGTAGGAGACACACTTTTGGGTA
TGGCTACACAATGTGTTCAAGTCAAGAATGTAATAAAAACATCTCCTCAAACTCTGTCAAAC
TTGTGCCTAAAGATAAATGTTAAACTCGGAGGGATCAATAATATTCTTGTACCTCATCAAAG
ACCTTCTGTGTTCCAGCAACCAGTGATCTTTTTGGGAGCCGATGTCACTCATCCACCTGCTG
GTGATGGAAAGAAGCCTTCTATTGCTGCTGTTGTAGGTAGTATGGATGCACACCCAAGCAGA
TACTGTGCCACAGTAAGAGTTCAGAGACCCCGACAGGAGATCATCCAGGACTTGGCCTCCAT
GGTCCGGGAACTTCTTATTCAATTTTATAAGTCAACTCGGTTCAAGCCTACTCGTATCATCT
TTTATCGGGATGGTGTTTCAGAGGGGCAGTTTAGGCAGGTATTATATTATGAACTACTAGCA
ATTCGAAGGCCTGCATCAGTTTGGAGAAAGACTATCAACCTGGAATAACCTACATTGTAGT
TCAGAAGAGACATCACACTCGATTATTTTGTGCTGATAGGACAGAAAGGGTTGGAAGAAGTG
GCAATATCCCAGCTGGAACAACAGTTGATACAGACATTACACACCCATATGAGTTCGATTTT
TACCTCTGTAGCCATGCTGGAATACAGGGTACCAGTCGTCCTTCACACTATCATGTTTTATG
GGATGATAACTGCTTTACTGCAGATGAACTTCAGCTGCTAACTTACCAGCTCTGCCACACTT
ACGTACGCTGTACACGATCTGTTTCTATACCTGCACCAGCGTATTATGCTCACCTGGTAGCA
TTTAGAGCCAGATATCATCTTGTGGACAAAGAACATGACAGTGCTGAAGGAAGTCACGTTTC
AGGACAAAGCAATGGGCGAGATCCACAAGCTCTTGCCAAGGCTGTACAGATTCACCAAGATA
CCTTACGCACAATGTACTTCGCTTAA
```

Fig. 16 (con).

```
>HILI, cDNA sequence of predicted ORF
ATATCTTCTGGTGATGCTGGAAGTACCTTCATGGAAGAGGTGTGAAAAACAAACAGGACTT
TATGGATTTGAGTATCTGTACCAGAGAAAAATTGGCACATGTGAGAAATTGTAAAACAGGTT
CCAGTGGAATACCTGTGAAACTGGTTACAAACCTCTTTAACTTAGATTTTCCCCAAGACTGG
CAGCTATACCAGTACCATGTGACATATATTCCAGATTTAGCATCTAGAAGGCTGAGAATTGC
TTTACTTTATAGTCATAGTGAACTTTCCAACAAAGCAAAAGCATTCGACGGTGCCATCCTTT
TTCTGTCACAAAAGCTAGAAGAAAAGGTCACAGAGTTGTCAAGTGAAACTCAAAGAGGTGAG
ACTATAAAGATGACTATCACCCTGAAGAGGGAGCTGCCATCAAGTTCTCCCGTGTGCATCCA
GGTCTTCAATATCATCTTCAGAAAGATCCTCAAAAAGTTGTCCATGTACCAAATTGGACGGA
ACTTCTATAATCCTTCAGAGCCAATGGAAATTCCCCAGCACAAATTATCCCTTTGGCCTGGG
TTTGCCATTTCTGTGTCATATTTTGAAAGGAAGCTCCTGTTTAGTGCTGATGTGAGTTACAA
AGTCCTCCGGAATGAGACGGTTCTGGAATTCATGACTGCTCTCTGTCAAAGAACTGGCTTGT
CCTGTTTCACCCAGACGTGTGAGAAGCAGCTAATAGGGCTCATTGTCCTTACAAGATACAAT
AACAGAACCTACTCCATTGATGACATTGACTGGTCAGTGAAGCCCACACACACCTTTCAGAA
GCGGGATGGCACCGAGATCACCTATGTGGATTACTACAAGCAGCAGTATGATATTACTGTAT
CGGACCTGAATCAGCCCATGCTTGTTAGTCTGTTAAAGAAGAAGAGAAATGACAACAGTGAG
GCTCAGCTCGCCCACCTGATACCTGAGCTCTGCTTTCTAACAGGGCTGACTGACCAGGCAAC
ATCTGATTTCCAGCTGATGAAGGCTGTGGCTGAAAAGACACGTCTCAGTCCTTCAGGCCGGC
AGCAGCGCCTGGCCAGGCTTGTGGACAACATCCAGAGGAATACCAATGCTCGCTTTGAACTA
GAGACCTGGGGACTGCATTTTGGAAGCCAGATATCTCTGACTGGCCGGATTGTGCCTTCAGA
AAAAATATTAATGCAAGACCACATATGTCAACCTGTGTCTGCTGCTGACTGGTCCAAGGATA
TTCGAACTTGCAAGATTTTAAATGCACAGTCTTTGAATACCTGGTTGATTTTATGTAGCGAC
AGAACTGAATATGTTGCCGAGAGCTTTCTGAACTGCTTGAGAAGAGTTGCAGGTTCCATGGG
ATTTAATGTAATGTGCATTCTGCCTTCTAATCAGAAGACCTATTATGATTCCATTAAAAAAT
ATTTGAGCTCAGACTGCCCAGTCCCAAGCCAATGTGTGCTTGCTCGGACCTTGAATAAACAG
GGCATGATGATGAGTATCGCCACCAAGATCGCTATGCAGATGACTTGCAAGCTCGGAGGCGA
GCTGTGGGCTGTGGAAATACCTTTAAAGTCCCTGATGGTGGTCGGTATTGATGTCTGTAAAG
ATGCACTCAGCAAGGACGTGATGGTTGTTGGATGCGTGGCCAGTGTTAACCCCAGAATCACC
AGGTGGTTTTCCCGCTGTATCCTTCAGAGAACAATGACTGATGTTGCAGATTGCTTGAAAGT
TTTCATGACTGGAGCACTCAACAAATGGTACAAGTACAATCATGATTTGCCAGCACGGATAA
TTGTGTACCGTGCTGGTGTAGGGGATGGTCAGCTGAAAACACTTATTGAATATGAAGTCCCA
CAGCTGCTGAGCAGTGTGGCAGAATCCAGCTCAAATACCAGCTCAAGACTGTCGGTGATTGT
GGTCAGGAAGAAGTGCATGCCACGATTCTTTACCGAAATGAACCGCACTGTACAGAACCCCC
CACTTGGCACTGTTGTGGATTCAGAAGCAACACGTAACGAATGGCAGTATGACTTTTATCTG
ATCAGCCAGGTGGCCTGCCGGGGAACTGTTAGTCCTACCTACTATAATGTCATCTATGATGA
CAACGGCTTGAAGCCCGACCATATGCAGAGACTTACATTCAAATTGTGCCACCTGTACTACA
ACTGGCCGGGCATAGTCAGTGTCCCAGCACCATGTCAGTATGCTCACAAGCTGACCTTTCTG
GTGGCACAAAGCATTCATAAAGAACCCAGTCTGGAATTAGCCAACCATCTCTTCTACCTG
```

Fig. 16 (con.)

```
>HIWI, cDNA sequence of predicted ORF
ATGACTGGGAGAGCCCGAGCCAGAGCCAGAGGAAGGGCCCGCGGTCAGGAGACAGCGCAGCT
GGTGGGCTCCACTGCCAGTCAGCAACCTGGTTATATTCAGCCTAGGCCTCAGCCGCCACCAG
CAGAGGGGGAATTATTTGGCCGTGGACGGCAGAGAGGAACAGCAGGAGGAACAGCCAAGTCA
CAAGGACTCCAGATATCTGCTGGATTTCAGGAGTTATCGTTAGCAGAGAGAGGAGGTCGTCG
TAGAGATTTTCATGATCTTGGTGTGAATACAAGGCAGAACCTAGACCATGTTAAAGAATCAA
AAACAGGTTCTTCAGGCATTATAGTAAGGTTAAGCACTAACCATTTCCGGCTGACATCCCGT
CCCCAGTGGGCCTTATATCAGTATCACATTGACTATAACCCACTGATGGAAGCCAGAAGACT
CCGTTCAGCTCTTCTTTTTCAACACGAAGATCTAATTGGAAAGTGCCATGCTTTTGATGGAA
CGATATTATTTTTACCTAAAAGACTACAGCAAAAGGTTACTGAAGTTTTTAGTAAGACCCGG
AATGGAGAGGATGTGAGGATAACGATCACTTTAACAAATGAACTTCCACCTACATCACCAAC
TTGTTTGCAGTTCTATAATATTATTTTCAGGAGGCTTTTGAAAATCATGAATTTGCAACAAA
TTGGACGAAATTATTATAACCCAAATGACCCAATTGATATTCCAAGTCACAGGTTGGTGATT
TGGCCTGGCTTCACTACTTCCATCCTTCAGTATGAAAACAGCATCATGCTCTGCACTGACGT
TAGCCATAAAGTCCTTCGAAGTGAGACTGTTTTGGATTTCATGTTCAACTTTTATCATCAGA
CAGAAGAACATAAATTTCAAGAACAAGTTTCCAAAGAACTAATAGGTTTAGTTGTTCTTACC
AAGTATAACAATAAGACATACAGAGTGGATGATATTGACTGGGACCAGAATCCCAAGAGCAC
CTTTAAGAAAGCCGACGGCTCTGAAGTCAGCTTCTTAGAATACTACAGGAAGCAATACAACC
AAGAGATCACCGACTTGAAGCAGCCTGTCTTGGTCAGCCAGCCCAAGAGAAGGCGGGGCCCT
GGGGGGACACTGCCAGGGCCTGCCATGCTCATTCCTGAGCTCTGCTATCTTACAGGTCTAAC
TGATAAAATGCGTAATGATTTTAACGTGATGAAAGACTTAGCCGTTCATACAAGACTAACTC
CAGAGCAAAGGCAGCGTGAAGTGGGACGACTCATTGATTACATTCATAAAAACGATAATGTT
CAAAGGGAGCTTCGAGACTGGGGTTTGAGCTTTGATTCCAACTTACTGTCCTTCTCAGGAAG
AATTTTGCAAACAGAAAAGATTCACCAAGGTGGAAAAACATTTGATTACAATCCACAATTTG
CAGATTGGTCCAAAGAAACAAGAGGTGCACCATTAATTAGTGTTAAGCCACTAGATAACTGG
CTGTTGATCTATACGCGAAGAAATTATGAAGCAGCCAATTCATTGATACAAAATCTATTTAA
AGTTACACCAGCCATGGGCATGCAAATGAGAAAAGCAATAATGATTGAAGTGGATGACAGAA
CTGAAGCCTACTTAAGAGTCTTACAGCAAAAGGTCACAGCAGACACCCAGATAGTTGTCTGT
CTGTTGTCAAGTAATCGGAAGGACAAATACGATGCTATTAAAAAATACCTGTGTACAGATTG
CCCTACCCCAAGTCAGTGTGTGGTGGCCCGAACCTTAGGCAAACAGCAAACTGTCATGGCCA
TTGCTACAAAGATTGCCCTACAGATGAACTGCAAGATGGGAGGAGAGCTCTGGAGGGTGGAC
ATCCCCCTGAAGCTCGTGATGATCGTTGGCATCGATTGTTACCATGACATGACAGCTGGGCG
GAGGTCAATCGCAGGATTTGTTGCCAGCATCAATGAAGGGATGACCCGCTGGTTCTCACGCT
GCATATTTCAGGATAGAGGACAGGAGCTGGTAGATGGGCTCAAAGTCTGCCTGCAAGCGGCT
CTGAGGGCTTGGAATAGCTGCAATGAGTACATGCCCAGCCGGATCATCGTGTACCGCGATGG
CGTAGGAGACGGCCAGCTGAAAACACTGGTGAACTACGAAGTGCCACAGTTTTTGGATTGTC
TAAAATCCATTGGTAGAGGTTACAACCCTAGACTAACGGTAATTGTGGTGAAGAAAAGAGTG
AACACCAGATTTTTTGCTCAGTCTGGAGGAAGACTTCAGAATCCACTTCCTGGAACAGTTAT
TGATGTAGAGGTTACCAGACCAGAATGGTATGACTTTTTTATCGTGAGCCAGGCTGTGAGAA
GTGGTAGTGTTTCTCCCACACATTACAATGTCATCTATGACAACAGCGGCCTGAAGCCAGAC
CACATACAGCGCTTGACCTACAAGCTGTGCCACATCTATTACAACTGGCCAGGTGTCATTCG
TGTTCCTGCTCCTTGCCAGTACGCCCACAAGCTGGCTTTTCTTGTTGGCCAGAGTATTCACA
GAGAGCCAAATCTGTCACTGTCAAACCGCCTTTACTACCTC
```

* primers used in both reactions (semi-nested PCR)

RNA-INTERFERENCE BY SINGLE-STRANDED RNA MOLECULES

This application is a divisional of U.S. Ser. No. 14/337,710, filed Jul. 22, 2014, which is a continuation of U.S. Ser. No. 13/329,710 filed Dec. 19, 2011, which is a divisional of U.S. Ser. No. 10/520,470 filed Jan. 7, 2005, now U.S. Pat. No. 8,101,348 issued Jan. 24, 2012, which is a 35 U.S.C. 371 National Phase Entry Application from PCT/EP2003/007516, filed Jul. 10, 2003, which claims the benefit of European Patent Application Nos. 02015532.1 filed Jul. 10, 2002 and 02018906.4 filed Aug. 23, 2002, the disclosures of which are incorporated herein in their entirety by reference.

DESCRIPTION

The present invention relates to sequence and structural features of single-stranded (ss)RNA molecules required to mediate target-specific nucleic acid modifications by RNA-interference (RNAi), such as target mRNA degradation and/or DNA methylation.

Most eukaryotes possess a cellular defense system protecting their genomes against invading foreign genetic elements. Insertion of foreign elements is believed to be generally accompanied by formation of dsRNA that is interpreted by the cell as a signal for unwanted gene activity (e.g. 5 Ahlquist, Science 296 (2002), 1270-1273; Fire et al., Nature 391 (1998), 806-811). Dicer RNase III rapidly processes dsRNA to small dsRNA fragments of distinct size and structure (e.g. Bernstein et al., Nature 409 (2001), 363-366), the small interfering RNAs (siRNAs) (Elbashir et al., Genes & Dev. 15 (2001 b), 188-200), which direct the sequence-specific o degradation of the single-stranded mRNAs of the invading genes. siRNA duplexes have 2- to 3-nt 3' overhanging ends and contain 5' phosphate and free 3' hydroxyl termini WO 02/44321). The process of posttranscriptional dsRNA-dependent gene silencing is commonly referred to as RNA interference (RNAi), and in some instances is also linked to transcriptional silencing.

Experimental introduction of siRNA duplexes into mammalian cells is now widely used to disrupt the activity of cellular genes homologous in sequence to the introduced dsRNA. Used as a reverse genetic approach, siRNA-induced gene silencing accelerates linking of gene sequence to biological function. siRNA duplexes are short enough to bypass general dsRNA-induced unspecific effects in vertebrate animal and mammalian cells. siRNAs may also be expressed intracellularly from introduced expression plasmids or viral vectors providing an alternative to chemical RNA synthesis. Therefore, an understanding of how siRNAs act in mammalian systems is important for refining this gene silencing technology and for producing gene-specific therapeutic agents.

Biochemical studies have begun to unravel the mechanistic details of RNAi. The first cell-free systems were developed using *D. melanogaster* cell or embryo extracts, and were followed by the development of in vitro systems from *C. elegans* embryo and mouse embryonal carcinoma cells. While the *D. melanogaster* lysates support the steps of dsRNA processing and sequence-specific mRNA targeting, the latter two systems only recapitulate the first step.

RNAi in *D. melanogaster* extracts is initiated by ATP-dependent processing of long dsRNA to siRNAs by Dicer RNase III (e.g. Bernstein et al., (2001), supra). Thereafter, siRNA duplexes are assembled into a multi-component complex, which guides the sequence-specific recognition of the target mRNA and catalyzes its cleavage (e.g. Elbashir (2001 b), supra). This complex is referred to as RNA-induced silencing complex (RISC) (Hammond et al., Nature 404 (2000), 293-296). siRNAs in *D. melanogaster* are predominantly 21- and 22-nt, and when paired in a manner to contain a 2-nt 3' overhanging structure effectively enter RISC (Elbashir et al., EMBO J. 20 (2001 c), 6877-6888). Mammalian systems have siRNAs of similar size, and siRNAs of 21- and 22-nt also represent the most effective sizes for silencing genes expressed in mammalian cells (e.g. Elbashir et al., Nature 411 (2001 a), 494-498, Elbashir et al., Methods 26 (2002), 199-213).

RISC assembled on siRNA duplexes in *D. melanogaster* embryo lysate targets homologous sense as well as antisense single-stranded RNAs for degradation. The cleavage sites for sense and antisense target RNAs are located in the middle of the region spanned by the siRNA duplex. Importantly, the 5'-end, and not the 3'-end, of the guide siRNA sets the ruler for the position of the target RNA cleavage. Furthermore, a 5' phosphate is required at the target-complementary strand of a siRNA duplex for RISC activity, and ATP is used to maintain the 5' phosphates of the siRNAs (Nykanen et al., Cell 107 (2001), 309-321). Synthetic siRNA duplexes with free 5' hydroxyls and 2-nt 3' overhangs are so readily phosphorylated in *D. melanogaster* embryo lysate that the RNAi efficiencies of 5'-phosphorylated and non-phosphorylated siRNAs are not significantly different (Elbashir et al. (2001 c), supra).

Unwinding of the siRNA duplex must occur prior to target RNA recognition. Analysis of ATP requirements revealed that the formation of RISC on siRNA duplexes required ATP in lysates of *D. melanogaster*. Once formed, RISC cleaves the target RNA in the absence of ATP. The need for ATP probably reflects the unwinding step and/or other conformational rearrangements. However, it is currently unknown if the unwound strands of an siRNA duplex remain associated with RISC or whether RISC only contains a single-stranded siRNA.

A component associated with RISC was identified as Argonaute2 from *D. melanogaster* Schneider 2 (S2) cells (Hammond et al., Science 293 (2001 a), 1146-1150), and is a member of a large family of proteins. The family is referred to as Argonaute or PPD family and is characterized by the presence of a PAZ domain and a C-terminal Piwi domain, both of unknown function (Cerutti et al., Trends Biochem. Sci. (2000), 481-482); Schwarz and Zamore, Genes & Dev. 16 (2002), 1025-1031). The PAZ domain is also found in Dicer. Because Dicer and Argonaute2 interact in S2 cells, PAZ may function as a protein-protein interaction motif. Possibly, the interaction between Dicer and Argonaute2 facilitates siRNA incorporation into RISC. In *D. melanogaster*, the Argonaute family has five members, most of which were shown to be involved in gene silencing and development. The mammalian members of the Argonaute family are poorly characterized, and some of them have been implicated in translational control, microRNA processing and development. The biochemical function of Argonaute proteins remains to be established and the development of more biochemical systems is crucial.

Here we report on the analysis of human RISC in extracts prepared from HeLa cells. The reconstitution of RISC and the mRNA targeting step revealed that RISC is a ribonucleoprotein complex that is composed of a single-stranded siRNA. Once RISC is formed the incorporated siRNA can no longer exchange with free siRNAs. Surprisingly, RISC can be reconstituted in HeLa S100 extracts providing single-stranded siRNAs. Introducing 5' phosphorylated single-stranded antisense siRNAs into HeLa cells potently silences an endogenous gene with similar efficiency than duplex siRNA.

The object underlying the present invention is to provide novel agents capable of mediating target-specific RNAi.

The solution of this problem is provided by the use of a single-stranded RNA molecule for the manufacture of an agent for inhibiting the expression of said target transcript. Surprisingly, it was found that single-stranded RNA molecules are capable of inhibiting the expression of target transcripts by RNA-interference (RNAi).

The length of the single-stranded RNA molecules is preferably from 14-50 nt, wherein at least the 14 to 20 5'-most nucleotides are substantially complementary to the target RNA transcript. The RNA oligonucleotides may have a free 5' hydroxyl moiety, or a moiety which is 5' phosphorylated (by means of chemical synthesis or enzymatic reactions) or which is modified by 5'-monophosphate analogues.

The inhibition of target transcript expression may occur in vitro, e.g. in eucaryotic, particularly mammalian cell cultures or cell extracts. On the other hand, the inhibition may also occur in vivo i.e. in eucaryotic, particularly mammalian organisms including human beings.

Preferably, the single-stranded RNA molecule has a length from 15-29 nucleotides. The RNA-strand may have a 3 hydroxyl group. In some cases, however, it may be preferable to modify the 3' end to make it resistant against 3' to 5' exonucleases. Tolerated 3'-modifications are for example terminal 2'-deoxy nucleotides, 3' phosphate, 2',3'-cyclic phosphate, C3 (or C6, C7, C12) aminolinker, thiol linkers, carboxyl linkers, non-nucleotidic spacers (C3, C6, C9, C12, abasic, triethylene glycol, hexaethylene glycol), biotin, fluoresceine, etc.

The 5'-terminus comprises an OH group, a phosphate group or an analogue thereof. Preferred 5' phosphate modifications are 5'-monophosphate $<<(HO)_2(O)P—O-5')$, 5'-diphosphate $((HO)_2(O)P—O—P(HO)(O)—O-5')$, 5'-triphosphate$((HO)_2(O)P—O—(HO)(O)P—O—P(HO)(O)—O-5')$, 5'-guanosine cap (7-methylated or non-methylated) $(7m-G-O-5'-(HO)(O)P—O—(HO)(O)P—O—P(HO)(O)—O-5')$, 5'-adenosine cap (Appp), and any modified or unmodified nucleotide cap structure $(N—O-5'-(HO)(O)P—O—(HO)(O)P—O—P(HO)(O)—O-5')$, 5'-monothiophosphate (phosphorothioate; $(HO)_2(S)P—O-5')$, 5'-monodithiophosphate (phosphorodithioate; $(HO)(HS)(S)P—O-5')_f$, 5'-phosphorothiolate $((HO)_2(O)P—S-5')$; any additional combination of oxygen/sulfur replaced monophosphate, diphosphate and triphosphates (e.g. 5'-alpha-thiotriphosphate, 5'-gamma-thiotriphosphate, etc.), 5'-phosphoramidates $((HO)_2(O) P—NH-5\backslash (HO) (NH_2) (O) P—O-5')$, 5'-alkylphosphonates (R=alkyl=methyl, ethyl, isopropyl, propyl, etc., e.g. $RP(OH)(O)—O-5'-$, $(OH)_2(O)P-5'—CH_2—$), 5'-alkyletherphosphonates (R=alkylether=methoxymethyl ($MeOCH_2—$), ethoxymethyl, etc., e.g. $RP(OH)(O)—O-5'-$).

The sequence of the RNA molecule of the present invention has to have a sufficient identity to a nucleic acid target molecule in order to mediate target-specific RNAi. Thus the single-stranded RNA molecule of the present invention is substantially complementary to the target transcript.

The target RNA cleavage reaction guided by the single-stranded RNA molecules of the present invention is highly sequence-specific. However, no all positions of the RNA molecule contribute equally to target recognition. Mismatches, particularly at the 3'-terminus of the single-stranded RNA molecule, more particularly the residues 3' to the first 20 nt of the single-stranded RNA molecule are tolerated. Especially preferred are single-stranded RNA molecules having at the 5'-terminus at least 15 and preferably at least 20 nucleotides which are completely complementary to a predetermined target transcript or have at only mismatch and optionally up to 35 nucleotides at the 3'-terminus which may contain 1 or several, e.g. 2, 3 or more mismatches.

In order to enhance the stability of the single-stranded RNA molecules, the 3'-ends may be stabilized against degradation, e.g. they may be selected such that they consist of purine nucleotides, particularly adenosine or guanosine nucleotides. Alternatively or additionally, 3'nucleotides may be substituted by modified nucleotide analogues, including backbone modifications of ribose and/or phosphate residues.

In an especially preferred embodiment of the present invention the RNA molecule may contain at least one modified nucleotide analogue. The nucleotide analogues may be located at positions where the target-specific activity, e.g. the RNAi mediating activity is not substantially affected, e.g. in a region at the 5'-end and/or the 3'-end of the RNA molecule. Particularly, the 3'-terminus may be stabilized by incorporating modified nucleotide analogues, such as non-nucleotidic chemical derivatives such as C3 (or C6, C7, C12) aminolinker, thiol linkers, carboxyl linkers, non-nucleotidic spacers (C3, C6, C9, C12, abasic, triethylene glycol, hexaethylene glycol), biotin, fluoresceine, etc. A further modification, by which the nuclease resistance of the RNA molecule may be increased, is by covalent coupling of inverted nucleotides, e.g. 2'-deoxyribonucleotides or ribonucleotides to the 3'-end of the RNA molecule. A preferred RNA molecule structure comprises: 5'-single-stranded siRNA-3'-O—P(O)(OH)—O-3'-N, wherein N is a nucleotide, e.g. a 2'-deoxyribonucleotide or ribonucleotide, typically an inverted thymidine residue, or an inverted oligonucleotide structure, e.g. containing up to 5 nucleotides.

Preferred nucleotide analogues are selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; 5-methyl-cytidine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. In preferred sugar-modified ribonucleotides the 2' OH-group is replaced by a group selected from H, OR, R, halo, SH, SR, $NH_2$, NHR, $NR_2$ or CN, wherein R is $C_r.C_6$ alkyl, alkenyl, alkynyl or methoxyethoxy, and halo is F, Cl, Br or I. In preferred backbone-modified ribonucleotides the phosphoester group connecting to adjacent ribonucleotides is replaced by a modified group, e.g. a phosphorothioate, phosphorodithioate, N3'-O5'- and/or N5'-O3' phosphoramidate group. It should be noted that the above modifications may be combined. For example, complementary or non-complementary nucleotides at the 3'-terminus, particularly after at least 15, more particularly after at least 20 5'-terminal nucleotides may be modified without significant loss of activity.

The single-stranded RNA molecule of the invention may be prepared by chemical synthesis. Methods of synthesizing RNA molecules are known in the art.

The single-stranded RNAs can also be prepared by enzymatic transcription from synthetic DNA templates or from DNA plasmids isolated from recombinant bacteria and subsequent 5'-terminal modification. Typically, phage RNA polymerases are used such as T7, T3 or SP6 RNA polymerase.

A further aspect of the present invention relates to a method of mediating RNA interference in a cell or an organism comprising the steps:

(a) contacting the cell or organism with the single-stranded RNA molecule of the invention under conditions wherein target-specific nucleic acid modifications may occur and (b) mediating a target-specific nucleic acid modification effected by the single-stranded RNA towards a target nucleic acid having a sequence portion substantially complementary to the single-stranded RNA.

Preferably the contacting step (a) comprises introducing the single-stranded RNA molecule into a target cell, e.g. an isolated target cell, e.g. in cell culture, a unicellular microorganism or a target cell or a plurality of target cells within a multicellular organism. More preferably, the introducing step comprises a carrier-mediated delivery, e.g. by liposomal carriers and/or by injection. Further suitable delivery systems include Oligofectamine (Invitrogen) and Transit-TKO siRNA Transfection reagent (Mirus)

The method of the invention may be used for determining the function of a gene in a cell or an organism or even for modulating the function of a gene in a cell or an organism, being capable of mediating RNA interference.

The cell is preferably a eukaryotic cell or a cell line, e.g. a plant cell or an animal cell, such as a mammalian cell, e.g. an embryonic cell, a pluripotent stem cell, a tumor cell, e.g. a teratocarcinoma cell or a virus-infected cell. The organism is preferably a eukaryotic organism, e.g. a plant or an animal, such as a mammal, particularly a human.

The target gene to which the RNA molecule of the invention is directed may be associated with a pathological condition. For example, the gene may be a pathogen-associated gene, e.g. a viral gene, a tumor-associated gene or an autoimmune disease-associated gene. The target gene may also be a heterologous gene expressed in a recombinant cell or a genetically altered organism. By determining or modulating, particularly, inhibiting the function of such a gene valuable information and therapeutic benefits in the agricultural field or in the medicine or veterinary medicine field may be obtained.

The ssRNA is usually administered as a pharmaceutical composition. The administration may be carried out by known methods, wherein a nucleic acid is introduced into a desired target cell in vitro or in vivo. Commonly used gene transfer techniques include calcium phosphate, DEAE-dextran, electroporation and microinjection and viral methods (Graham, F. L. and van der Eb, A. J. (1973) Virol. 52, 456; McCutchan, J. H. and Pagano, J. S. (1968), J. Natl. Cancer Inst. 41, 351; Chu, G. et al (1987), Nucl. Acids Res. 15, 1311; Fraley, R. et al. (1980), J. Biol. Chem. 255, 10431; Capec-chi, M. R. (1980), Cell 22, 479). A recent addition to this arsenal of techniques for the introduction of nucleic acids into cells is the use of cationic liposomes (Feigner, P. L. et al. (1987), Proc. Natl. Acad. Sci USA 84, 7413). Commercially available cationic lipid formulations are e.g. Tfx 50 (Promega) or Lipofectamin2000 (Life Technologies). A further preferred method for the introduction of RNA into a target organism, particularly into a mouse, is the high-pressure tail vein injection (Lewis, D. L. et al. (2002), Nat.Genet.29, 29; McCaffrey, A. P. et al. (2002), Nature 418, 38-39).

Herein, a buffered solution comprising the single-stranded RNA (e.g. about 2 ml) is injected into the tail vein of the mouse within 10 s.

Thus, the invention also relates to a pharmaceutical composition containing as an active agent at least one single-stranded RNA molecule as described above and a pharmaceutical carrier. The composition may be used for diagnostic and for therapeutic applications in human medicine or in veterinary medicine.

For diagnostic or therapeutic applications, the composition may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes. A further preferred administration method is injection.

A further preferred application of the RNAi method is a functional analysis of eukaryotic cells, or eukaryotic non-human organisms, preferably mammalian cells or organisms and most preferably human cells, e.g. cell lines such as HeLa or 293 or rodents, e.g. rats and mice. By transfection with suitable single-stranded RNA molecules which are homologous to a prede-termined target gene or DNA molecules encoding a suitable single-stranded RNA molecule a specific knockout phenotype can be obtained in a target cell, e.g. in cell culture or in a target organism. The presence of short single-stranded RNA molecules does not result in an interferon response from the host cell or host organism.

In an especially preferred embodiment, the RNA molecule is administered associated with biodegradable polymers, e.g. polypeptides, poly(d,l-lactic-co-glycolic acid) (PLGA), polylysine or polylysine conjugates, e.g. polylysine-graft-imidazole acetic acid, or poly(beta-amino ester) or microparticles, such as microspheres, nanoparticles or nanospheres. More preferably the RNA molecule is covalently coupled to the polymer or microparticle, wherein the covalent coupling particularly is effected via the 3'-terminus of the RNA molecule.

Further, the invention relates to a pharmaceutical composition for inhibiting the expression of a target transcript by RNAi comprising as an active agent a single-stranded RNA molecule having a length from 14-50, preferably 15-29 nucleotides wherein at least the 14-20 5'most nucleotides are substantially complementary to said target transcript.

Furthermore, the invention relates to a method for the prevention or treatment of a disease associated with over-expression of at least one target gene comprising administering a subject in need thereof a single-stranded RNA molecule having a length from 14-50, preferably 15-29 nucleotides wherein at least the 14-20 5'most nucleotides are substantially complementary to a target transcript in an amount which is therapeutically effective for RNAi.

Still, a further subject matter of the invention is a eukaryotic cell or a eukaryotic non-human organism exhibiting a target gene-specific knockout phenotype comprising an at least partially deficient expression of at least one endogenous target gene wherein said cell or organism is transfected with at least one single-stranded RNA molecule capable of inhibiting the expression of at least one endogenous target gene. It should be noted that the present invention allows the simultaneous delivery of several anti-sense RNAs of different sequences, which are either cognate to a different or the same target gene.

Gene-specific knockout phenotypes of cells or non-human organisms, particularly of human cells or non-human mammals may be used in analytic procedures, e.g. in the functional and/or phenotypical analysis of complex physiological processes such as analysis of gene expression profiles and/or proteomes. For example, one may prepare the knock-out phenotypes of human genes in cultured cells which are assumed to be regulators of alternative splicing processes. Among these genes are particularly the members of the SR splicing factor family, e.g. ASF/SF2, SC35, SRp20, SRp40 or SRp55. Further, the effect of SR proteins on the mRNA profiles of predetermined alternatively spliced genes such as CD44 may be analysed. Preferably the analysis is carried out by high-throughput methods using oligonucleotide based chips.

Using RNAi based knockout technologies, the expression of an endoge-neous target gene may be inhibited in a target cell or a target organism. The endogeneous gene may be complemented by an exogeneous target nucleic acid coding for the target protein or a variant or mutated form of the target protein, e.g. a gene or a cDNA, which may optionally be fused to a further nucleic acid sequence encoding a detectable peptide or poly-peptide, e.g. an affinity tag, particularly a multiple affinity tag. Variants or mutated forms of the target gene differ from the endogeneous target gene in that they encode a gene product which differs from the endogeneous gene product on the amino acid level by substitutions, insertions and/or deletions of single or multiple amino acids. The variants or mutated forms may have the same biological activity as the endogeneous target gene. On the other hand, the variant or mutated target gene may also have a biological activity, which differs from the biological activity of the endogeneous target gene, e.g. a partially deleted activity, a completely deleted activity, an enhanced activity etc.

The complementation may be accomplished by coexpressing the polypeptide encoded by the exogeneous nucleic acid, e.g. a fusion protein com-prising the target protein and the affinity tag and the double stranded RNA molecule for knocking out the endogeneous gene in the target cell. This coexpression may be accomplished by using a suitable expression vector expressing both the polypeptide encoded by the exogeneous nucleic acid, e.g. the tag-modified target protein and the single-stranded RNA molecule or alternatively by using a combination of expression vectors. Proteins and protein complexes which are synthesized de novo in the target cell will contain the exogeneous gene product, e.g. the modified fusion protein. In order to avoid suppression of the exogeneous gene product expression by the RNAi molecule, the nucleotide sequence encoding the exogeneous nucleic acid may be altered on the DNA level (with or without causing mutations on the amino acid level) in the part of the sequence which is homologous to the single-stranded RNA molecule. Alternatively, the endogeneous target gene may be complemented by corresponding nucleotide sequences from other species, e.g. from mouse.

Preferred applications for the cell or organism of the invention is the analysis of gene expression profiles and/or proteomes. In an especially preferred embodiment an analysis of a variant or mutant form of one or several target proteins is carried out, wherein said variant or mutant forms are reintroduced into the cell or organism by an exogeneous target nucleic acid as described above. The combination of knockout of an endogeneous gene and rescue by using mutated, e.g. partially deleted exogeneous target has advantages compared to the use of a knockout cell. Further, this method is particularly suitable for identifying functional domains of the target protein. In a further preferred embodiment a comparison, e.g. of gene expression profiles and/or proteomes and/or phenotypic characteristics of at least two cells or organisms is carried out. These organisms are selected from:

(i) a control cell or control organism without target gene inhibition, (ii) a cell or organism with target gene inhibition and (iii) a cell or organism with target gene inhibition plus target gene complementation by an exogeneous target nucleic acid.

The method and cell of the invention may also be used in a procedure for identifying and/or characterizing pharmacological agents, e.g. identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein comprising:

(a) a eukaryotic cell or a eukaryotic non-human organism capable of expressing at least one endogeneous target gene coding for said target protein, (b) at least one single-stranded RNA molecule capable of inhibiting the expression of said at least one endogeneous target gene by RNAi and (c) a test substance or a collection of test substances wherein pharma-cological properties of said test substance or said collection are to be identified and/or characterized.

Further, the system as described above preferably comprises:

(d) at least one exogeneous target nucleic acid coding for the target protein or a variant or mutated form of the target protein wherein said exogeneous target nucleic acid differs from the endogeneous target gene on the nucleic acid level such that the expression of the exogeneous target nucleic acid is substantially less inhibited by the single-stranded RNA molecule than the expression of the endoge-neous target gene.

Furthermore, the RNA knockout complementation method may be used for preparative purposes, e.g. for the affinity purification of proteins or protein complexes from eukaryotic cells, particularly mammalian cells and more particularly human cells. In this embodiment of the invention, the exogeneous target nucleic acid preferably codes for a target protein which is fused to an affinity tag.

The preparative method may be employed for the purification of high molecular weight protein complexes which preferably have a mass of >150 kD and more preferably of >500 kD and which optionally may contain nucleic acids such as RNA. Specific examples are the heterotrimeric protein complex consisting of the 20 kD, 60 kD and 90 kD proteins of the U4/U6 snRNP particle, the splicing factor SF3b from the 17S U2 snRNP consisting of 5 proteins having molecular weights of 14, 49, 120, 145 and 155 kD and the 25S U4/U6/U5 tri-snRNP particle containing the U4, U5 and U6 snRNA molecules and about 30 proteins, which has a molecular weight of about 1.7 MD.

This method is suitable for functional proteome analysis in mammalian cells, particularly human cells.

Finally, the invention relates to a purified and isolated mammalian, particularly human RNA-induced silencing complex (RISC) having an apparent molecular weight of less than about 150-160 kDa, e.g. about 120 to 150-160 kDa. The RISC comprises polypeptide and optionally nucleic acid components, particularly single-stranded RNA molecules as described above. The RISC may be used as a target for diagnosis and/or therapy, as a diagnostic and/or therapeutic agent itself, as a molecular-biological reagent or as component in a screening procedure for the identification and/or characterization of pharmaceutical agents.

Polypeptide components of RISC preferably comprise members of the Argonaute family of proteins, and contain eIF2C1 and/or eIF2C2, and possibly at least one other expressed eIF2C family member, particularly selected from eIF2C3, eIF2C4, HILI and HIWI.

Expression or overexpression of one or several proteins present in RISC in suitable host cells, e.g. eukaryotic cells, particularly mammalian cells, is useful to assist an RNAi response. These proteins may also be expressed or overexpressed in transgenic animals, e.g. vertebrates, particularly mammals, to produce animals particularly sensitive to injected single-stranded or double-stranded siRNAs. Further, the genes encoding the proteins may be administered for therapeutic purposes, e.g. by viral or non-viral gene delivery vectors.

It is also conceivable to administer a siRNA/eIF2C1 or 2 complex directly by the assistance of protein transfection reagents (e.g. Amphoteric Protein Transfection Reagents, ProVectin protein (Imgenex), or similar products) rather than RNA/DNA transfection. This may have technical advantages over siRNA transfection that are limited to nucleic acid transfection.

Alternatively to the application of siRNAs as synthetic double-stranded or single-stranded siRNAs, it is conceivable to also administer an antisense siRNA precursor molecule in the form of a hairpin stem-loop structure comprising 19 to 29 base pairs in the stem with or without 5' or 3' overhanging ends on one side of the duplex and a nucleotide or non-nucleotide loop on the other end. Preferably, the hairpin structure has a 3' overhang of from 1-5 nucleotides. Further, the precursor may contain modified nucleotides as described above, particularly in the loop and/or in the 3' portion, particularly in the overhang. The siRNA or precursors of siRNAs may also be introduced by viral vectors or RNA expression systems into a RISC compound, e.g. eIF2C1 and/or 2 overexpressing organism or cell line. The siRNA precursors may also be generated by direct expression within an organism or cell line. This may be achieved by transformation with a suitable expression vector carrying a nucleic acid template operatively linked to an expression control sequence to express the siRNA precursor.

Further, the present invention is explained in more detail in the following figures and examples.

BRIEF DESCRIPTION OF THE DRAWINGS

FIG. 1(A) Representation of the 177-nt $^{32}$P-cap-labeled target RNA with the targeting siRNA duplex. Target RNA cleavage site and the length of the expected cleavage products is also shown. The fat black line positioned under the antisense siRNA is used in the following figures as symbol to indicate the region of the target RNA, which is complementary to the antisense siRNA sequence. FIG. 1(B) Comparison of the siRNA mediated target RNA cleavage using the previously established D. melanogaster embryo in vitro system and HeLa cell S100 cytoplasmic extract. 10 nM cap-labeled target RNA was incubated with 100 nM siRNA as described in materials. Reaction products were resolved on a 6% sequencing gel. Position markers were generated by partial RNase T1 digestion (T1) and partial alkaline hydrolysis (OH) of the cap-labeled target RNA. The arrow indicates the 5' cleavage product, the 3' fragment is unlabeled and therefore invisible.

FIG. 2(A) Illustration of the possible 5' and 3' aminolinker modifications of the sense and antisense strands of a siRNA duplex. L5 represents a 6-carbon chain aminolinker connected via a 5'-phosphodiester linkage, L3 represents a 7-carbon aminolinker connected via a phosphodiester bond to the terminal 3' phosphate, s, sense; as, antisense. FIG. 2(B) Target RNA cleavage testing various combinations of 5' and 3' aminolinker-modified siRNA duplexes. NC (negative control) shows an incubation reaction of the target RNA in the absence of siRNA duplex. T1, RNase T1 ladder; OH, partial alkaline hydrolysis ladder.

FIG. 3(A) Sequence of the radiolabeled siRNA duplex. The labeled nucleotide was joined to synthetic 20-nt antisense siRNA by T4 RNA ligation of $^{32}$pCp. The various combinations of 5' and 3' hydroxyl/phosphate were prepared as described in materials. X and Y indicate 5' and 3' modifications of the antisense siRNA. FIG. 3(B) Fate of the antisense siRNA during incubation of the modified siRNA duplexes in HeLa S100 extract in the presence of non-radiolabeled target RNA. The different phosphorylated forms of the antisense siRNA were distinguished based on their gel mobility. Identical results were obtained when using 5' phosphorylated sense siRNA or when leaving out the target RNA during incubation. Ligation products are only observed when 3' phosphates were present on the labeled antisense siRNA.

FIG. 5A, FIG. B, FIG. C. Partial purification of human RISC.

FIG. 5(A) Graphical representation of the structure of the biotinylated siRNA duplex used for affinity purification of siRNA-associated factors. L3 indicates a C7-aminolinker that was conjugated to a photo-cleavable biotin N-hydroxysuccinimidyl ester; UV indicates photocleavage of the UV-sensitive linkage to release affinity selected complexes under native conditions. FIG. 5 (C) Glycerol gradient (5%-20%) sedimentation of siRNPs recovered by UV treatment/elution from the streptavidin affinity column. For legend, see (B). When monitoring the precise size of target RNA cleavage fragments using internally $^{32}$P-UTP-labeled, capped mRNA, the sum is equal to the full-length transcript, thus indicating that target RNA is indeed only cleaved once in the middle of the region spanned by the siRNA.

siRNPs were subjected to affinity selection after incubation using siRNA duplexes with one or both strands biotinylated. The eluate recovered after UV treatment or the unbound fraction after streptavidin affinity selection (flow-through) was assayed for target RNA degradation. If the antisense strand was biotinylated, all sense target RNA-cleaving RISC was bound to the streptavidin beads, while sense siRNA biotinylation resulted in RISC activity of the flow-through. The cleavage reaction in the flow-through fraction was less efficient than in the UV eluate, because affinity-selected RISC was more concentrated.

FIG. 7A and FIG. 7B. Single-stranded antisense siRNAs reconstitute RISC in HeLa S100 extracts.

Analysis of RISC reconstitution using single-stranded or duplex siRNAs comparing HeLa S100 extracts FIG. 7(A) and the previously described *D. melanogaster* embryo lysate FIG. 7(B). Different concentrations of single-stranded siRNAs (s, sense; as, antisense) and duplex siRNA (ds) were tested for specific targeting of cap-labeled substrate RNA. 100 nM concentrations of the antisense siRNA reconstituted RISC in HeLa S100 extract, although at reduced levels in comparison to the duplex siRNA. Reconstitution with single-stranded siRNAs was almost undetectable in *D. melanogaster* lysate, presumably because of the higher nuclease activity in this lysate causing rapid degradation of uncapped single-stranded RNAs.

FIG. 8A and FIG. 8B. Single-stranded antisense siRNAs mediate gene silencing in HeLa cells.

FIG. 8(A) Silencing of nuclear envelope protein lamin A/C. Fluorescence staining of cells transfected with lam in A/C-specific siRNAs and GL2 lucif erase (control) siRNAs. Top row, staining with lamin A/C specific antibody; middle row, Hoechst staining of nuclear chromatin; bottom row, phase contrast images of fixed cells. FIG. 8(B) Quantification of lamin A/C knockdown after Western blot analysis. The blot was stripped after lamin A/C probing and reprobed with vimentin antibody. Quantification was performed using a Lumi-Imager (Roche) and LumiAnalyst software to quantitate the ECL signals (Amersham Biosciences), differences in gel loading were corrected relative to non-targeted vimentin protein levels. The levels of lamin A/C protein were normalized to the non-specific GL2 siRNA duplex.

Figure 9:
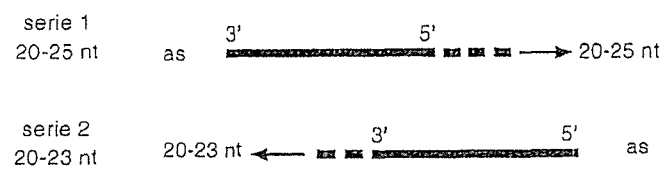
Figure 9:
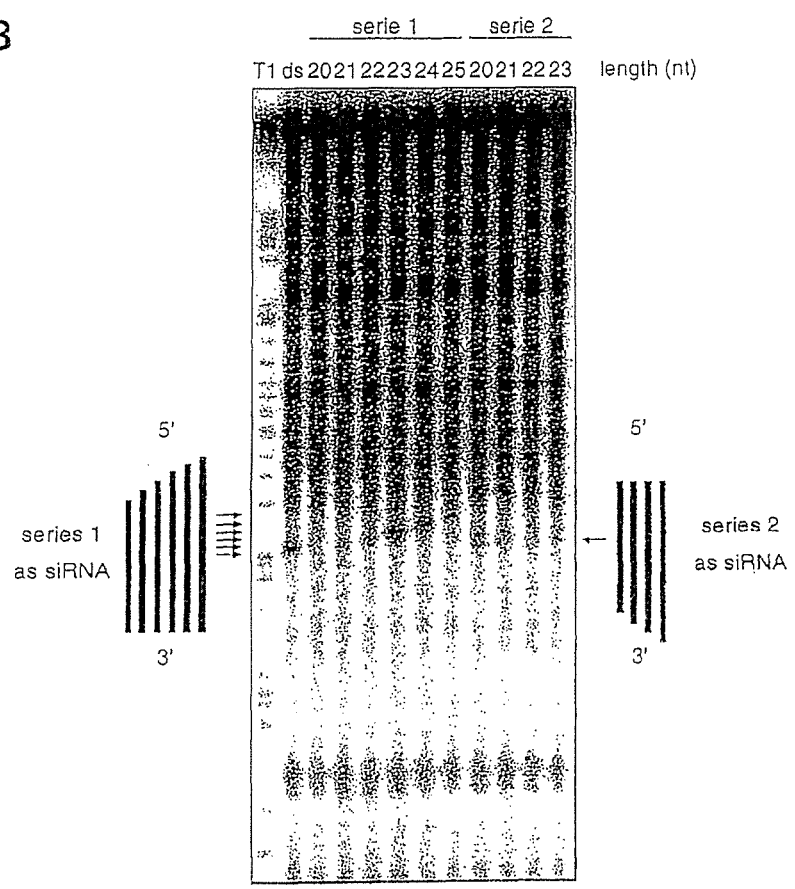

FIG. 9A and FIG. 9B. Antisense siRNAs of different length direct target RNA cleavage in HeLa S100 extracts.

FIG. 9(A) Graphical representation of the experiment. Antisense siRNAs were extended towards the 5' side (series 1, 20 to 25-nt) or the 3'side (series 2, 20 to 23-nt).

FIG. 9(B) Target RNA cleavage using the antisense siRNAs described in FIG. 9(A). HeLa S100 extract was incubated with 10 nM cap-labeled target RNA and 100 nM antisense siRNAs at 30° C. for 2.5 h. Reaction products were resolved on a 6% sequencing gel. Position markers were generated by partial RNase T1 digestion (T1) and partial alkaline hydrolysis (OH) of the cap-labeled target RNA. Arrows indicate the position of the 5'cleavage products generated by the different antisense siRNAs. The fat black lines on the left (series 1) and the right (series 2) indicate the region of the target RNA, which is complementary to the antisense siRNA sequences.

Figure 10:
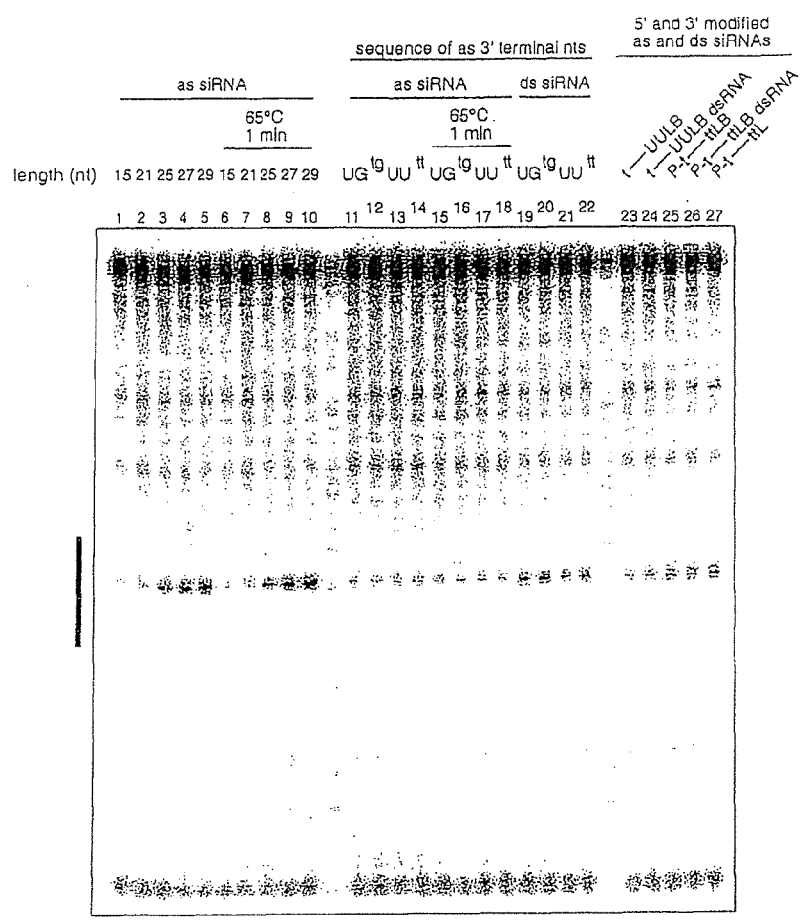

FIG. 10. Length dependence of antisense siRNAs and effect of terminal modifications for targeting RNA cleavage in HeLa S100 extracts.

HeLa S100 extract was incubated with 10 nM cap-labeled target RNA and 100 nM antisense siRNAs at 30° C. for 2.5 h. Reaction products were resolved on a 6% sequencing gel. Position markers were generated by partial RNase T1 digestion (T1) of the cap-labeled target RNA. The fat black line on the left indicates the region of the target RNA, which is complementary to the 21-nt antisense siRNA sequence. The siRNA sequences used in each experiment are listed below (sense and antisense siRNAs are listed together, they were pre-annealed to form duplex siRNAs). p, phosphate; t, 2'-deoxythymidine, c, 2'-deoxycytidine, g, 2'-deoxycytidine, g, 2'-deoxyguanosine; L, aminolinker, B, photocleavable biotin; A,C,G,U, ribonucleotides.

| Lane | Sense siRNA (5'-3') | Antisense siRNA (5'-3') |
|---|---|---|
| 1 |  | pUCGAAGUAUUCCG CG |
| 2 |  | pUCGAAGUAUUCCG CGUACGUG |
| 3 |  | pUCGAAGUAUUCCG CGUACGUGAUGU |
| 4 |  | pUCGAAGUAUUCCG CGUACGUGAUGUUC |
| 5 |  | pUCGAAGUAUUCCG CGUACGUGAUGUUC AC |
| 6 |  | pUCGAAGUAUUCCG CG |
| 7 |  | pUCGAAGUAUUCCG CGUACGUG |
| 8 |  | pUCGAAGUAUUCCG CGUACGUGAUGU |
| 9 |  | pUCGAAGUAUUCCG CGUACGUGAUGUUC |
| 10 |  | pUCGAAGUAUUCCG CGUACGUGAUGUUC AC |
| 11 |  | pUCGAAGUAUUCCG CGUACGUG |
| 12 |  | pUCGAAGUAUUCCG CGUACGtg |
| 13 |  | pUCGAAGUAUUCCG CGUACGUU |
| 14 |  | pUCGAAGUAUUCCG CGUACGtt |
| 15 |  | pUCGAAGUAUUCCG CGUACGUG |
| 16 |  | pUCGAAGUAUUCCG CGUACGtg |
| 17 |  | pUCGAAGUAUUCCG CGUACGUU |
| 18 |  | pUCGAAGUAUUCCG CGUACGtt |
| 19 | CGUACGCGGAAUACUUCG AAA | pUCGAAGUAUUCCG CGUACGUG |
| 20 | CGUACGCGGAAUACUUCG AAA | pUCGAAGUAUUCCG CGUACGtg |
| 21 | CGUACGCGGAAUACUUCG AAA | pUCGAAGUAUUCCG CGUACGUU |

-continued

| Lane | Sense siRNA (5'-3') | Antisense siRNA (5'-3') |
|---|---|---|
| 22 | CGUACGCGGAAUACUUCG AAA | pUCGAAGUAUUCCG CGUACGtt |
| 23 |  | tCGAAGUAUUCCGC GUACGUULB |
| 24 | cGUACGCGGAAUACUUCG AUULB | tCGAAGUAUUCCGC GUACGUULB |
| 25 |  | ptCGAAGUAUUCCGC GUACGttLB |
| 26 | cGUACGCGGAAUACUUCG AttLB | ptCGAAGUAUUCCGC GUACGttLB |
| 27 |  | ptCGAAGUAUUCCGC GUACGttL |

Figure 11:
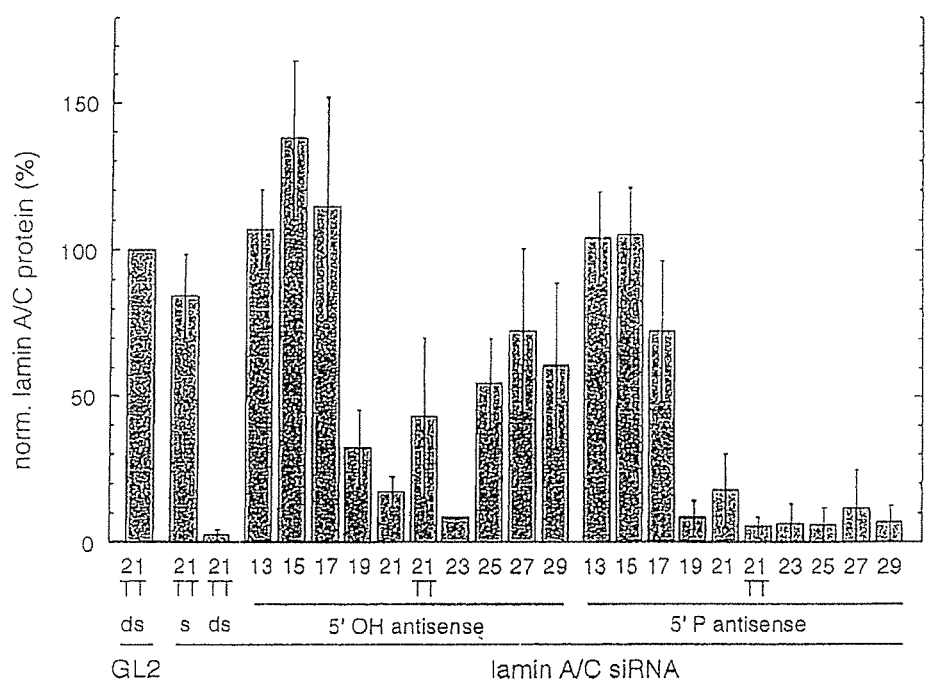

FIG. 11: Single-stranded antisense siRNAs mediate gene silencing in HeLa cells. Quantification of lamin A/C knockdown after Western blot analysis. The blot was stripped after lamin A/C probing and reprobed with vimentin antibody. Quantification was performed using a Lumi-Imager (Roche) and LumiAnalyst software to quantitate the ECL signals (Amersham Biosciences), differences in gel loading were corrected relative to non-targeted vimentin protein levels. The levels of lamin A/C protein were normalized to the non-specific GL2 siRNA duplex.

Figure 12:
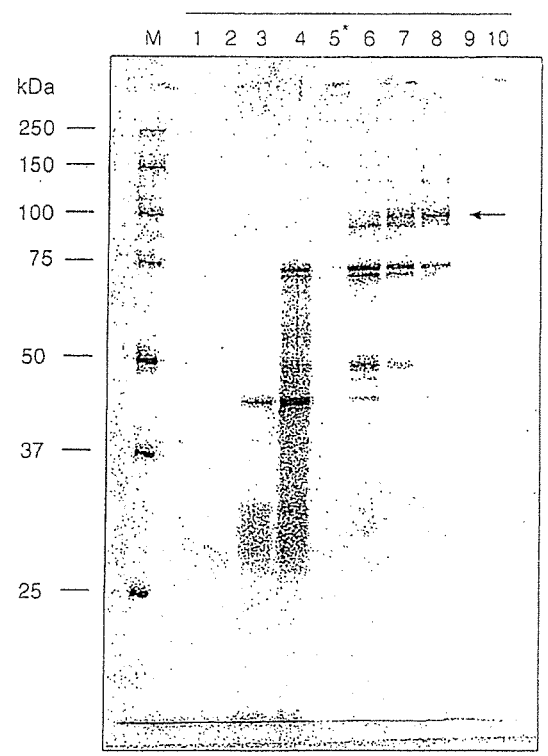

FIG. 12 A and FIG. B. Protein composition of affinity purified RISC.

Figure 12B:
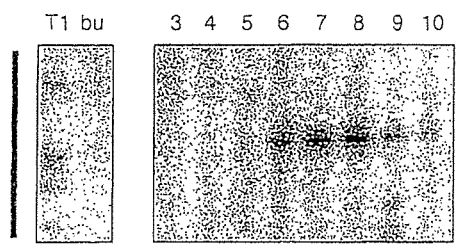

FIG. 12(A) Silver-stained SDS-PAGE gel of affinity-selected ribonucleoprotein complexes after glycerol gradient (5%-20%) sedimentation. The arrow indicates the band containing eIF2C1 and eIF2C2. Molecular size markers are indicated on the left. The asterisk indicates a fraction for which the protein pellet was lost after precipitation. FIG. 12(B) Target RNA cleavage assay of the collected fractions. RISC activity peaked in fraction 7 and 8; bu, buffer.

FIG. 13A, FIG. 13B and FIG. 13C. Mass spectrometric characterization of eIF2C1 and eIF2C2. The 100 kDa band was analysed by mass spectrometry. Mass spectrum indicating the peptide peaks corresponding to eIF2C2 FIG. 13(A) and eIF2C1 FIG. 13(B). FIG. 13(C) Alignment of eIF2C2 (SEQ ID NO:69)and eIF2C1 (SEQ ID NO:68) amino-acid sequences indicating the position of the identified peptides. Sequence differences are indicated by yellow boxes.

FIG. 14. Predicted amino-acid sequences of the six human Argonaute protein family members, eIF2C1 (SEQ ID NO:68), eIF2C2 (SEQ ID NO:69), eIF2C3 (SEQ ID NO: 70), eIF2C4 (SEQ ID NO:71), HILI (SEQ ID NO:72), and HIWI (SEQ ID NO:73).

Figure 15:
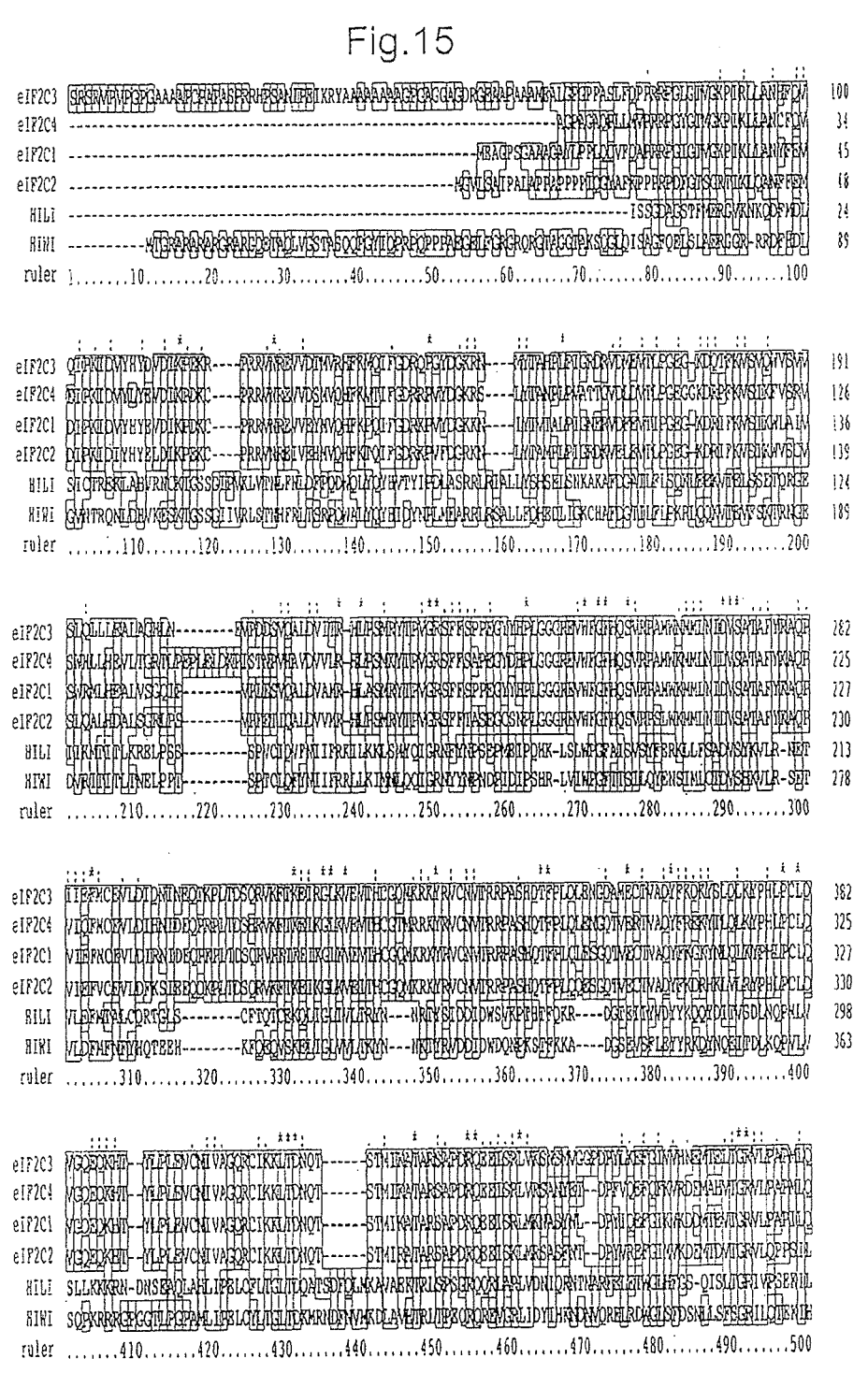
Figure 15:
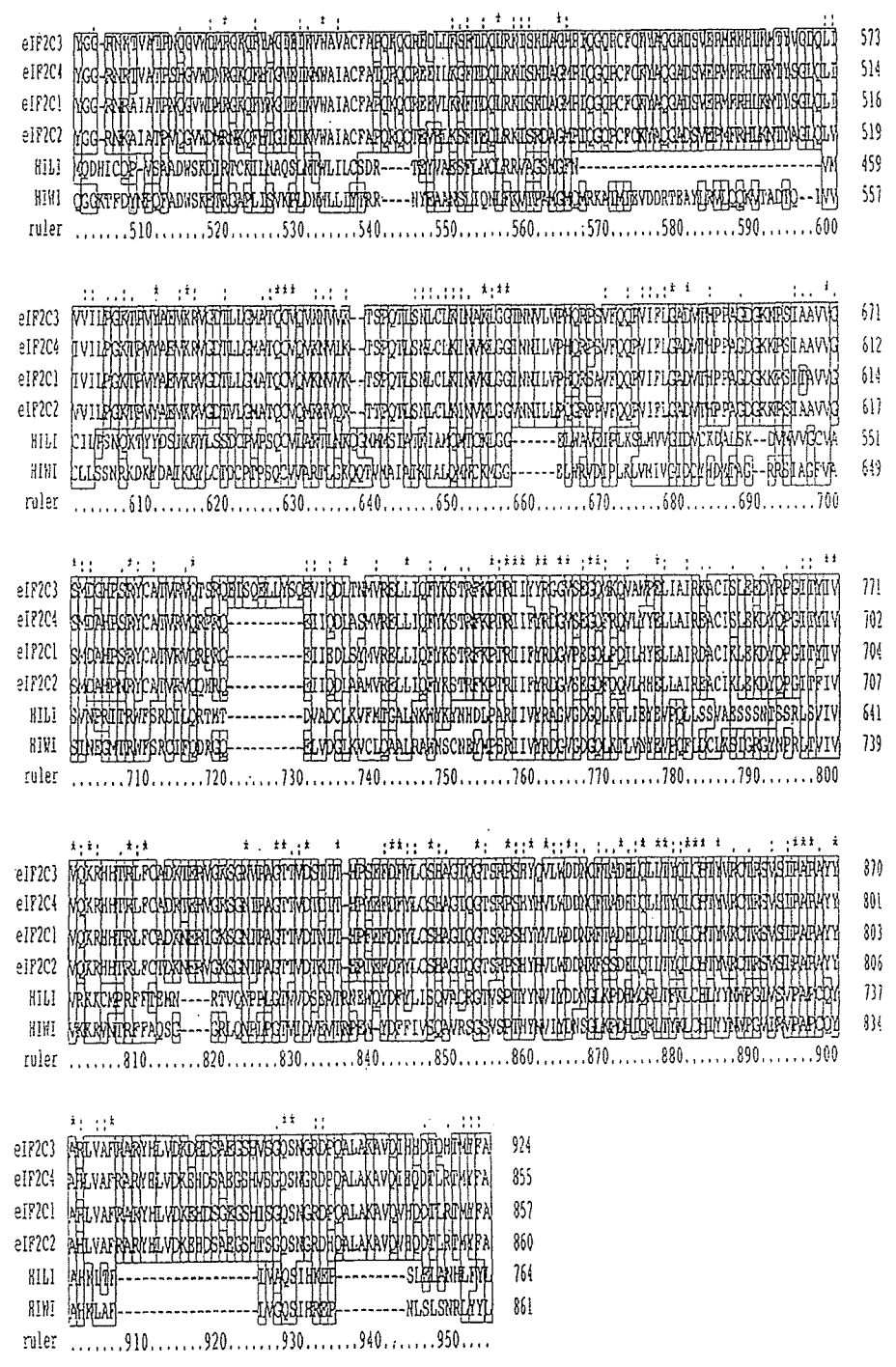

FIG. 15. Alignment of the sequences of the six human Argonaute protein family members. [eIF2C1; SEQ ID NO: 68; eIF2C2; SEQ ID NO: 69; eIF2C3: SEQ ID NO: 70; eIF2C4: SEQ ID NO: 71; HILI: SEQ ID NO: 72: HIWI: SEQ ID NO: 73].

FIG. 16. Predicted cDNA sequences of the six human Argonaute protein family members [eIF2C1; SEQ ID NO: 74; eIF2C2: SEQ ID NO: 75; eIF2C3: SEQ ID NO: 76; eIF2C4: SEQ ID NO: 77; HILI: SEQ ID NO: 78: HIWI: SEQ ID NO: 79.

FIG. 17A and FIG. 17B. All members of the Argonaute family but HIWI are expressed in o HeLa cells.

RT-PCR analysis on polyA RNA from HeLa cells. FIG. 17(A) Primers (forward and reverse) used for nested and semi-nested PCR amplification of the different Argonautes and expected length of the FOR products. FIG. 17(B) Agarose gel electrophoresis of the obtained PCR products, confirming the expected 5 length. Left lanes, 100 bp DNA ladder.

EXAMPLE

1. Material and Methods
1.1 siRNA Synthesis and Biotin Conjugation siRNAs were chemically synthesized using RNA phosphoramidites (Proligo, Hamburg, Germany) and deprotected and gel-purified as described previously. 5' aminolinkers were introduced by coupling MMT-C6-aminolinker phosphoramidite (Proligo, Hamburg), 3' C7-aminolinkers were introduced by assembling the oligoribonucleotide chain on 3'-aminomodifier (TFA) C7 lcaa control pore glass support (Chemgenes, Mass., USA). The sequences for GL2 luciferase siRNAs were as described (Elbashir et al., 2001 a, supra). If 5'-phosphates were to be introduced, 50 to 100 nmoles of synthetic siRNAs were treated with T4 polynucleotide kinase (300 µl reaction, 2.5 mM ATP, 70 mM Tris-HCl, pH 7.6, 10 mM $MgCl_2$, 5 mM DTT, 30 U T4 PNK, New England Biolabs, 45 min, 37° C.) followed by ethanol precipitation.

3' Terminal $^{32}$pCp labeling (FIG. 3) was performed in a 30 µl reaction (17 µM siRNA, 0.5 µM $^{32}$pCp (110 TBq/mmol), 15% DMSO, 20 U T4 RNA ligase, NEB, and 1×NEB-supplied reaction buffer) for 1.5 h at 37° C., and gel-purified. One half of the pCp-labeled RNA was dephosphorylated (25 µl reaction, 500 U alkaline phosphatase, Roche, and Roche-supplied buffer, 30 min, 50° C.), followed by phenol/chloroform extraction and ethanol precipitation. Half of this reaction was 5' phosphorylated (20 µl reaction, 2 units T4 polynucleotide kinase, NEB, 10 mM ATP, NEB-supplied buffer, 60 min, 37° C.). A quarter of the initial pCp-labeled siRNA was also 5' phosphorylated (10 µl reaction, 10 units 3' phosphatase-free T4 polynucleotide kinase, Roche, 10 mM ATP, Roche-supplied buffer, 3 min, 37° C.).

For conjugation to biotin, 20 to 65 nmoles of fully deprotected aminolinker-modified siRNA were dissolved in 100 µl of 100 mM sodium borate buffer (pH 8.5) and mixed with a solution of 1 mg of EZ-Link NHS-PC-LC-Biotin (Pierce, Ill., USA) in 100 µl of anhydrous dimethylformamide. The solution was incubated for 17 h at 25° C. in the dark. Subsequently, siRNAs were precipitated by the addition of 60 µl 2 M sodium acetate (pH 6.0) and 1 ml ethanol. The RNA pellet was collected by centrifugation and biotin-conjugated siRNA was separated from non-reacted siRNA on a preparative denaturing 18% acrylamide gel (40 cm length) in the dark. The RNA bands were visualized by 254 nm UV shadowing and minimized exposure time. The bands were excised, and the RNA was eluted overnight in 0.3 M NaCl at 4° C. and recovered by ethanol precipitation. siRNA duplexes were formed as previously described (Elbashir et al., Methods 26 (2002), 199-213).

1.2 Preparation of S100 Extracts from HeLa Ceils

Cytoplasm from HeLa cells adapted to grow at high density was prepared following the Dignam protocol for isolation of HeLa cell nuclei (Dignam et al., Nucleic Acids Res. 11 (1983), 1475-1489). The cytoplasmic fraction was supplemented with KCl, $MgCl_2$ and glycerol to final concentrations of 100 mM, 2 mM and 10%, respectively. At this stage, the extracts can be o stored frozen at −70° C. after quick-freezing in liquid nitrogen without loss of activity.

S100 extracts were prepared by ultracentrifugation at 31 0.500 rpm for 60 minutes at 4° C. using a Sorvall T-865 rotor. The protein concentration of HeLa S100 extract varied between 4 to 5 mg/ml as determined by Bradford assay.

1.3 Affinity Purification of RISC with 3' Biotinylated siRNA Duplexes

For affinity purification of siRNA-associated protein complexes from HeLa S100 extracts, 10 nM of a 3' double-biotinylated siRNA duplex were incubated in 0.2 mM ATP, 0.04 mM GTP, 10 U/ml RNasin, 6 µg/ml o creatine kinase, and 5 mM creatine phosphate in 60% S100 extract at 30° C. for 30 to 60 min and gentle rotation. Thereafter, 1 ml slurry of Immobilized Neutravidin Biotin Binding Protein (Pierce, Ill., USA) was added per 50 ml of reaction solution and the incubation was continued for another 60 to 120 min at 30° C. with gentle rotation. The Neutravidin beads were then collected at 2000 rpm for 2 minutes at 4° C. in a Heraeus Megafuge 1.0 R centrifuge using a swinging bucket rotor type 2704. Effective capturing of RISC components after affinity selection was confirmed by assaying the supernatant for residual RISC activity with and without supplementing fresh siRNA duplexes. The collected Neutravidin beads were washed with 10 volumes of buffer A relative to the bead volume (30 mM HEPES, pH 7.4, 100 mM KCl, 2 mM $MgCl_2$, 0.5 mM DTT, 10% glycerol) followed by washing with 5 volumes of buffer B (same as buffer A with only 3% glycerol content). The beads were transferred to a 0.8×4 cm Poly-Prep chromatography column (BioRad; CA, USA) by resuspending in 3 volumes of buffer B at 4° C., followed by 10 volumes of washing with buffer B. Washing of the beads was continued by 10 volumes of buffer B increased to 300 mM KCl. The column was then reequilibrated with regular buffer B. To recover native siRNA-associated complexes, the column was irradiated in the cold room by placing it at a 2 cm distance surrounded by four 312 nm UV lamps (UV-B tube, 8 W, Herolab, Germany) for 30 minutes. To recover the photocleaved siRNP solution, the column was placed into a 50 ml Falcon tube and centrifuged at 2000 rpm for 1 minute at 4° C. using again the 2704 rotor. For full recovery of siRNPs, the beads were once again resuspended in buffer B followed by a second round of UV treatment for 15 minutes. Both eluates were pooled and assayed for target RNA degradation.

1.4 Target RNA Cleavage Assays

Cap-labeled target RNA of 177 nt was generated as described (Elbashir et al., EMBO J. 20 (2001 c), 6877-6888) except that his-tagged guanylyl transferase was expressed in E. coli from a plasmid generously provided by J. Wilusz and purified to homogeneity. If not otherwise indicated, 5' phosphorylated siRNA or siRNA duplex was pre-incubated in supplemented HeLa S100 extract at 30° C. for 15 min prior to addition of cap-labeled target RNA. After addition of all components, final concentrations were 100 nM siRNA, 10 nM target RNA, 1 mM ATP, 0.2 mM GTP, 10 U/ml RNasin, 30 µg/ml creatine kinase, 25 mM creatine phosphate, 50% S100 extract. Incubation was continued for 2.5 h. siRNA-mediated target RNA cleavage in D. melanogaster embryo lysate was performed as described (Zamore et al., Cell 101 (2000), 25-33). Affinity-purified RISC in buffer B was assayed for target RNA cleavage without preincubation nor addition of extra siRNA (10 nM target RNA, 1 mM ATP, 0.2 mM GTP, 10 U/ml RNasin, 30 µg/ml creatine kinase, 25 mM creatine phosphate, 50% RISC in buffer B). Cleavage reactions were stopped by the addition of 8 vols of proteinase K buffer (200 mM Tris-HCl pH 7.5, 25 mM EDTA, 300 mM NaCl, 2% w/v SDS). Proteinase K, dissolved in 50 mM Tris-HCl pH 8.0, 5 mM $CaCl_2$, 50% glycerol, was added to a final concentration of 0.6 mg/ml and processed as described (Zamore et al. (2000), supra). Samples were separated on 6% sequencing gels.

1.5 Analytical Gel Filtration

UV-eluates in buffer B were fractionated by gel filtration using a Superdex 200 PC 3.2/30 column (Amersham Biosciences) equilibrated with buffer A on a SMART system (Amersham Biosciences). Fractionation was performed by using a flow rate of 40 µl/minute and collecting 100 µl fractions. Fractions were assayed for specific target RNA cleavage. Size calibration was performed using molecular size markers thyroglobulin (669 kDa), ferritin (440 kDa), catalase (232 kDa), aldolase (158 kDa) and BSA (66 kDa) (Amersham Biosciences).

1.6 Glycerol Gradient Sedimentation

UV-eluates were layered on top of 4 ml linear 5% to 20% (w/w) glycerol gradient adjusted to 30 mM HEPES, pH 7.4, 100 mM KCl, 2 mM $MgCl_2$, 0.5 mM DTT. Centrifugation was performed at 35000 rpm for 14.5 h at 4° C. using a Sorvall SW 60 rotor. Twenty fractions of 0.2 ml volume were removed sequentially from the top and 15 µl aliquots were used to assay for target RNA cleavage.

Results 2.1 A Human Biochemical System for siRNA Functional Analysis

Figure 1:
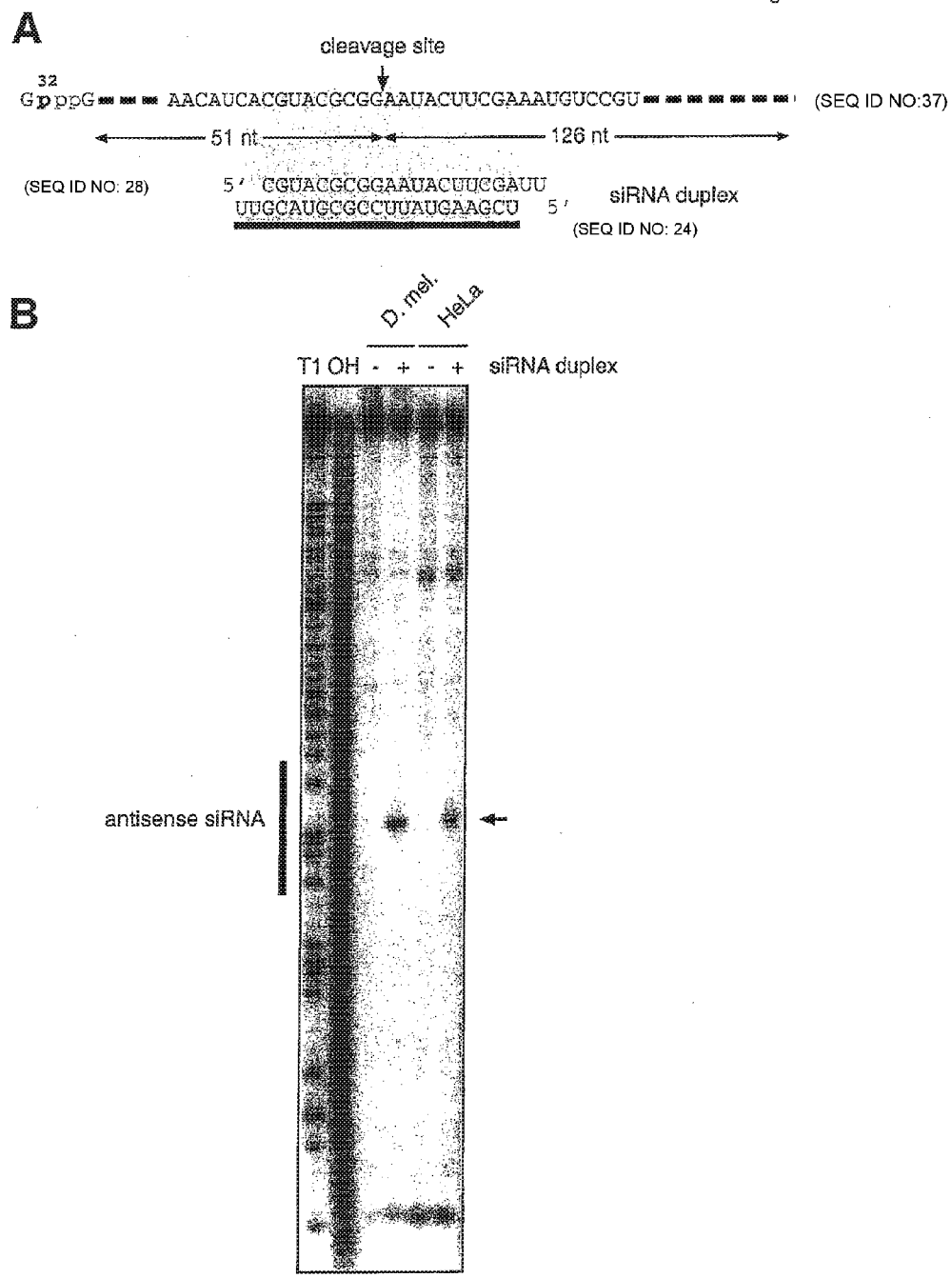
FIG. 1A and FIG. 1B. HeLa cytoplasmic S100 extracts show siRNA-dependent target RNA cleavage.

We were interested in assaying siRNA-mediated target RNA degradation in human cell extracts, because siRNAs are powerful reagents to knockdown gene expression in human cells but the action of siRNAs in human cells was uncertain. To investigate whether siRNAs guide target RNA degradation in human cells with a similar mechanism to the one observed in D. melanogaster (e.g. Elbashir et al. (2001 b), supra), we prepared substrates for targeted mRNA degradation as described previously (Elbashir et al. (2001 c), supra). A $5'$-$^{32}P$-cap-labeled, 177-nt RNA transcript, derived 5 from a segment of the firefly luciferase gene, was incubated in HeLa cell S100 or D. melanogaster embryo extracts with a 21-nt siRNA duplex in the presence of an ATP regeneration system (FIG. 1 A, B). siRNA cleavage assays were performed at 25° C. in D. melanogaster lysate and at 30° C. in HeLa S100 extracts for 2.5 h. After deproteinization using proteinase K, the reaction products were separated on a 6% sequencing gel.

Similar to the previous observation in D. melanogaster lysate, we observed the appearance of a cleavage product in HeLa S100 extract at exactly the same position, thus indicating that the siRNA duplex guides target RNA is cleavage in the human system with the same specificity and mechanism. The cleavage reaction appeared less efficient when compared to the D. melanogaster system, but this could be explained by the 5-fold lower total protein concentration of HeLa S100 extracts (25 mg/ml vs. 5 mg/ml). Similar to D. melanogaster lysates, siRNA duplexes without 5' phosphate were rapidly 5' phosphorylated in HeLa S100 extracts (see below) and the ability to cleave the target RNA was independent of the presence of a 5' phosphate on the synthetic siRNA duplexes.

Comparative analysis of the efficiency of siRNA duplexes of different length in D. melanogaster lysate and in transfected mammalian cells indicated that the differences in silencing efficiencies between 20- to 25-nt siRNA duplexes were less pronounced in mammalian cells than in D. melanogaster (Elbashir et al. (2002), supra). Duplexes of 24- and 25-nt siRNAs were inactive in D. melanogaster lysate, whereas the same 30 duplexes were quite effective for silencing when introduced by transfection into HeLa cells. We therefore asked whether siRNA duplexes of 20- to 25-nt are able to reconstitute RISC also with approximately equal efficiency. Indeed, we observed no large differences in our biochemical assay, and the position of target RNA cleavage was as predicted according to the cleavage guiding rules established in *D. melanogaster* lysate (data not shown). Our biochemical results therefore support the in vivo observations.

2.2 5' Modification of the Guide siRNA Inhibits RISC Activity

Figure 2:
FIG. 2A and FIG. 2B. Chemical modification of the 5' end of the antisense but not the sense siRNAs prevents sense target RNA cleavage in HeLa S100 extracts.
Figure 2:
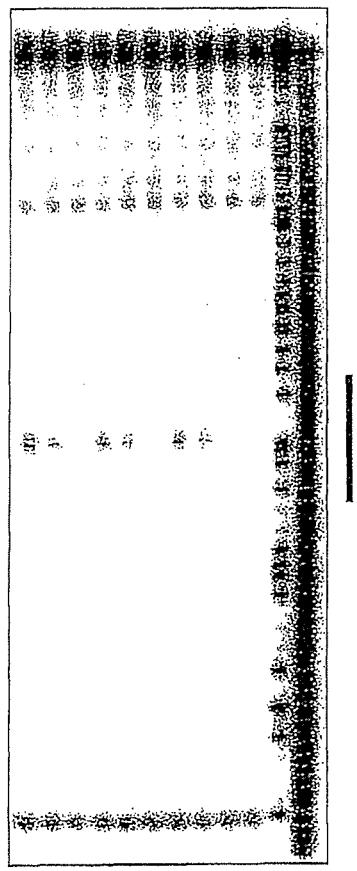

Modification of siRNAs at their termini is important for developing siRNA-based affinity purification schemes or for conjugating reporter tags o for biophysical measurements. The most common method for introducing reactive side chains into nucleic acids is by chemical synthesis using aminolinker derivatives (Eckstein (1991), Oligonucleotides and analogues, 2nd Ed., Oxford UK, Oxford University Press). After complete deprotection of the oligonucleotide, the primary amine is typically reacted with the 5 N-hydroxysuccinimidyl ester of the desired compound. We have introduced 5' and 3' aminolinkers with six and seven methylene groups as spacers, respectively. The linker-modified siRNA duplexes were tested for mediating target RNA degradation in HeLa S100 extract (FIG. 2A, B). Modification of the 5'-end of the antisense guide siRNA abolished target RNA cleavage, 0 while modification of neither the sense 5'-end nor of both 3'-ends showed any inhibitory effect. In an identical experiment using *D. melanogaster* embryo lysate, we observed a similar pattern of RISC activity although the duplex carrying the 5' aminolinker-modified antisense siRNA showed some residual activity (data not shown). Presumably, introduction of additional 5 atoms or the change in terminal phosphate electric charge at the 5'-end of the antisense siRNA interfered with its ability to function as guide RNA. The critical function of the guide siRNAs 5' end was previously documented (Elbashir et al. (2001 c), supra).

The ability to modify siRNAs at their 3'-end suggests that siRNAs do not play a major role for priming dsRNA synthesis and do not act as primers for degenerative PCR. The fate of a siRNA in HeLa S100 extracts was followed directly by incubation of an internally $^{32}$ pCp-radiolabeled siRNA duplexes. The radiolabeled antisense siRNA strand was also prepared with different 5' and 3' phosphate modifications (FIG. 3A). All described combinations of siRNA duplexes were fully competent for RISC-dependent target RNA degradation (data not shown). As previously observed for *D. melanogaster* lysates (Nykanen et al. (2001), supra), rapid 5' phosphorylation of siRNA duplexes with free 5' hydroxyl termini was apparent. To our surprise, we noted that a small fraction of the 3' phosphorylated antisense siRNA could be ligated to the opposing 5' hydroxyl of the sense siRNA producing a lower mobility band. The interstrand ligation was confirmed by changing the length of the unlabeled sense siRNA, which resulted in the expected mobility changes of the ligation product (data not shown). RNA ligase activity was previously observed in HeLa S100 extracts and it is mediated by two enzymatic activities (e.g. Vicente and Filipowicz, Eur. J. Biochem., 176 (1988), 431-439). The 3' terminal phosphate is first converted to a 2',3'-cyclic phosphate requiring ATP and 3' terminal phosphate cyclase. Thereafter, the opposing 5' hydroxyl is ligated to the cyclic phosphate end by an as yet uncharacterized RNA ligase. We chemically synthesized the predicted 5' phosphorylated, 42-nt ligation product and found that it is unable to mediate target RNA cleavage, presumably because it can not form activated RISC. The majority of the 3' phosphorylated duplexes siRNA was gradually dephosphorylated at its 3' end and emerged chemically similar to naturally generated siRNA. Together, these observations indicate that the cell has a mechanism to preserve the integrity of siRNAs. We were unable to detect a proposed siRNA-primed polymerization product (FIG. 3B), suggesting that siRNAs do not function as primers for template-dependent dsRNA synthesis in our system. However, we acknowledge that a proposed RNA-dependent polymerase activity may have been inactivated during preparation of our extracts.

2.3 siRNAs Incorporated into RISC do not Compete with a Pool of Free siRNAs

Figure 4:
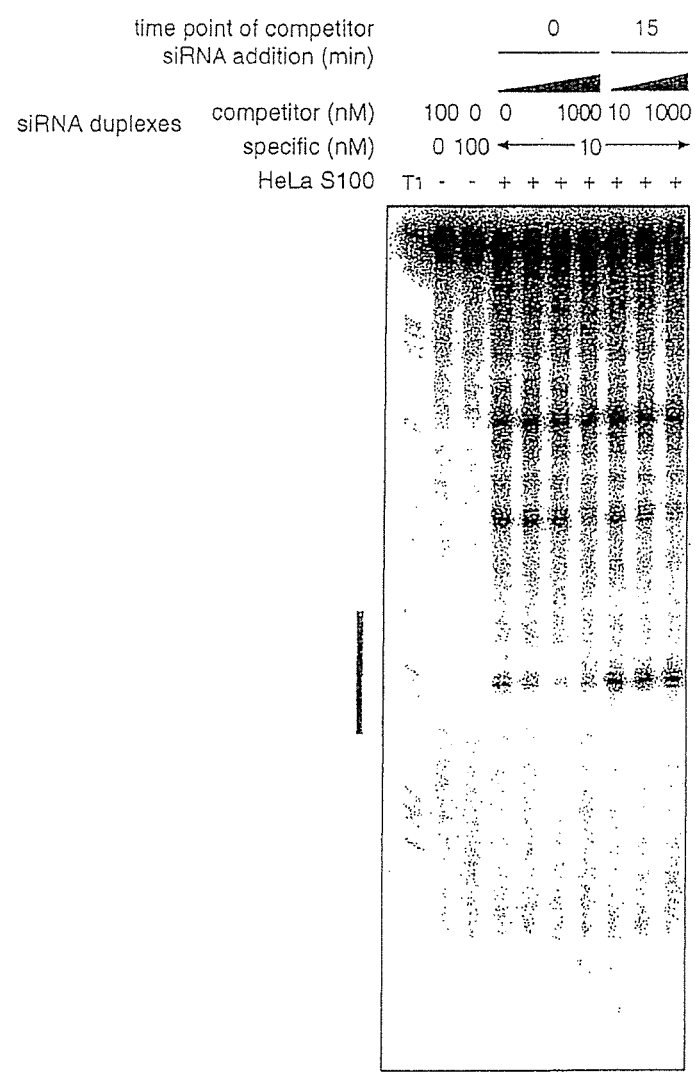
FIG. 4. RISC is a stable complex that does not rapidly exchange bound siRNA. Increasing concentrations of non-specific siRNA compete with target-specific RISC formation when added simultaneously to HeLa S100 extracts (lanes 4 to 7). However, when the unspecific siRNA duplex is added 15 min after pre-incubation with the specific siRNA duplex, no more competition was observed (3 lanes to the right). T1, RNase T1 ladder.

In order to analyze RISC assembly and stability, we tested whether target-unspecific siRNA duplexes were able to compete with target-specific siRNA duplexes. When specific and non-specific siRNA duplexes were co-incubated in HeLa S100 extracts, increasing concentrations of unspecific siRNA duplex competed with the formation of target-specific RISC (FIG. 4, left lanes). However, when target-specific siRNAs were pre-incubated in HeLa S100 extract for 15 min in the absence of competitor siRNA duplex, the assembled siRNA in the target-specific RISC could no longer be competed with the target-unspecific siRNA duplex (FIG. 4, right lanes). This result suggests that RISC is formed during the first 15 minutes of incubation and that siRNAs were irreversibly associated with the protein components of RISC during the 2.5 h time window of the experiment.

2.4 Purification of Human RISC

Figure 5:
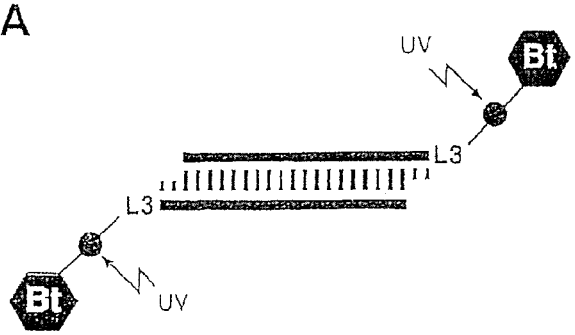
FIG. 5 (B) Superdex-200 gel filtration analysis of siRNA-protein complexes (siRNPs) recovered by UV treatment/elution (UV elu) from the streptavidin affinity column. Fractions were assayed for their ability to sequence-specifically cleave the cap-labeled target RNA. The number of the collected fractions and the relative positions of the aldolase (158 kDa) and BSA (66 kDa) size markers are indicated.
Figure 5:
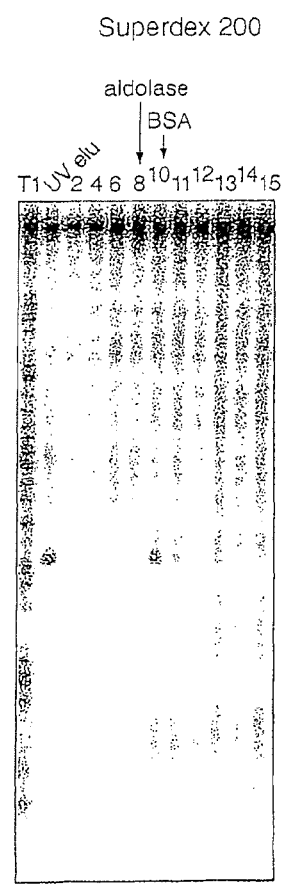
Figure 5:
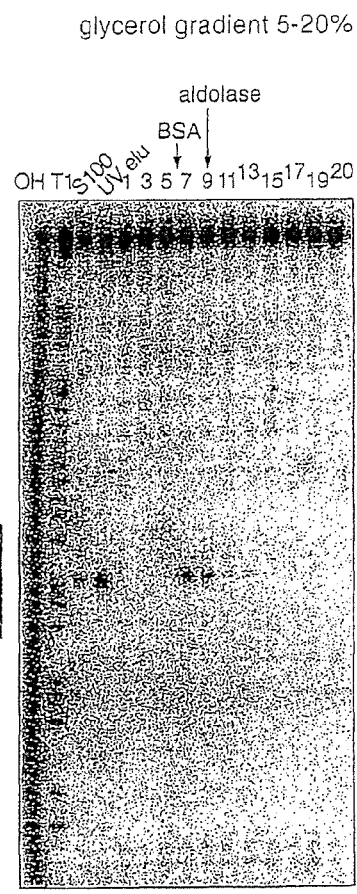
Figure 6:
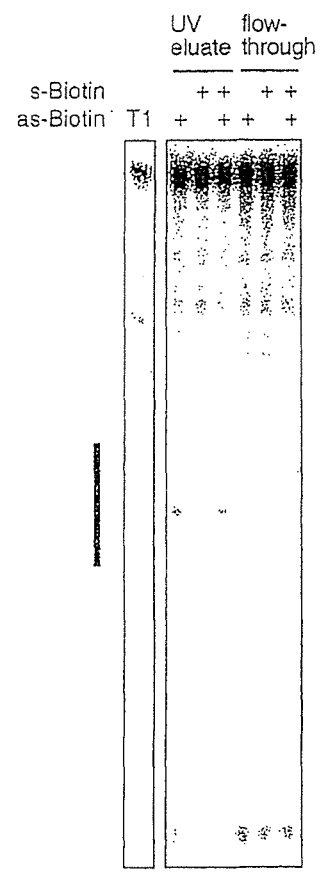
FIG. 6. RISC contains a single-stranded siRNA.

After having the 3' termini of siRNAs defined as the most suitable position for chemical modification, a photo-cleavable biotin derivative was conjugated to the 3' aminolinker-modified siRNAs. A photo-cleavable biotin derivative was selected because of the advantage of recovering RISC under non-denaturing conditions after capturing complexes on streptavidin-coated affinity supports. 3' Conjugation of biotin to the sense, antisense or to both of the strands did not affect target RNA cleavage when compared to non-biotinylated siRNAs (data not shown). siRNA duplexes with biotin residues on both 3' ends were therefore used for affinity purification (FIG. 5A). The double biotinylated siRNA duplex was incubated in HeLa S100 extracts in the presence of ATP, GTP, creatine phosphate, and creatine kinase for ATP regeneration. Thereafter, streptavidin-conjugated agarose beads were added to capture the biotinylated siRNA ribonucleoprotein complexes (siRNPs) including RISC. After extensive washing of the collected beads, the siRNPs were released by UV irradiation at 31 2 nm. The eluate cleaved target RNA sequence-specifically, thus indicating that RISC was recovered in its native state from the resin (FIG. 5B, C, lane UV elu). The flow-through from the affinity selection showed no detectable RISC activity indicating complete binding of RISC by the beads (FIG. 6). The affinity eluate was further analyzed by applying it onto a Superdex 200 gel filtration column (FIG. 5B) as well as a 5%-20% glycerol gradient ultra-centrifugation (FIG. 5C). Individual fractions were collected and assayed for target RNA cleavage without the addition of any further siRNA. RISC activity appeared between the molecular size markers aldolase (158 kDa) and BSA (66 kDa) after gel filtration or glycerol gradient centrifugation (FIG. 5B, C). The molecular size of human RISC is therefore estimated to be between 90 and 160 kDa, significantly smaller than the complex previously analyzed in *D. melanogaster* lysates (Hammond et al. (2000), supra; Nykanen et al. (2001), supra). The small size of RISC suggests that Dicer (210 kDa) is not contained in RISC and that the formation of RISC from synthetic siRNAs may occur independently of Dicer. While these results do not rule out a role for Dicer during assembly of RISC, they emphasize the absence of Dicer in RISC.

2.5 RISC Contains a Single siRNA Strand and can be Reconstituted Using Single-Stranded siRNAs Two models are currently discussed concerning the siRNA strand composition of RISC. The first model suggests that both strands of the initially added siRNA duplex are physically present in RISC, but in an unwound conformation. The second model proposes that RISC carries only a single siRNA strand, implying loss of one of the siRNA strands during assembly. The latter model has been favored based on the analogy to miRNA precursor processing, where only one 21-nt strand accumulated from a dsRNA hairpin precursor. The molecular basis for the asymmetry of the miRNA precursor processing reaction is not yet understood. Because siRNAs have symmetric 2-nt 3'-overhangs it is assumed that siRNA duplexes enter RISC with equal probability for both orientations, thus giving rise to distinct sense and antisense targeting RISCs.

To address the constitution of siRNAs in RISC, we affinity selected the assembled complexes with siRNA duplexes that were biotinylated at only one of the two constituting strands or both (FIG. 6). If both strands were present together in RISC, the cleavage activity should be affinity selected on Neutravidin independently of the position of the biotin residue. In contrast, we observed target RNA cleavage from UV eluates after streptavidin selection only for siRNA duplexes with biotin conjugated to the antisense" strand, but not the sense strand (FIG. 6). RISC activity, assembled on siRNA duplexes with only the sense siRNA biotinylated, remained in the flow-through. These data suggest that RISC contains only a single-stranded RNA molecule.

To assess whether single-stranded siRNAs may be able to reconstitute RISC, single-stranded 5' phosphorylated siRNAs as well as the siRNA duplex were incubated at concentrations between 1 to 100 nM with cap-labeled target RNA in HeLa S100 extract (FIG. 7A). At 100 nM single-stranded antisense siRNA, we detected RISC-specific target RNA cleavage, thus confirming that single-stranded siRNAs are present in RISC. At lower concentrations of single-stranded siRNAs, RISC formation remained undetectable while duplex siRNAs were effectively forming RISC even at 1 nM concentration. Therefore, a specific pathway exists which converts double-stranded siRNA into single-stranded siRNA containing RISC. Using *D. melanogaster* embryo lysate, we were unable to detect RISC activity from anti-sense siRNA (FIG. 7B), presumably because of the high load of single-strand specific ribonucleases (Elbashir et al. (2001 b), supra). Furthermore, 5' phosphorylated 20- to 25-nt antisense siRNAs were able to mediate RISC-specific target RNA degradation in HeLa S100 extract producing the same target RNA cleavage sites as duplex siRNAs of this length (data not shown).

Figure 8:
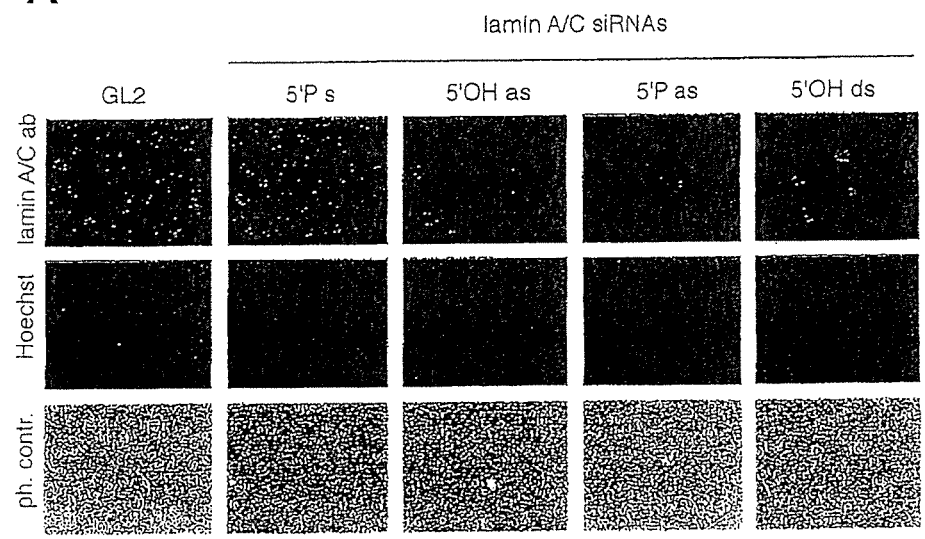
Figure 8:
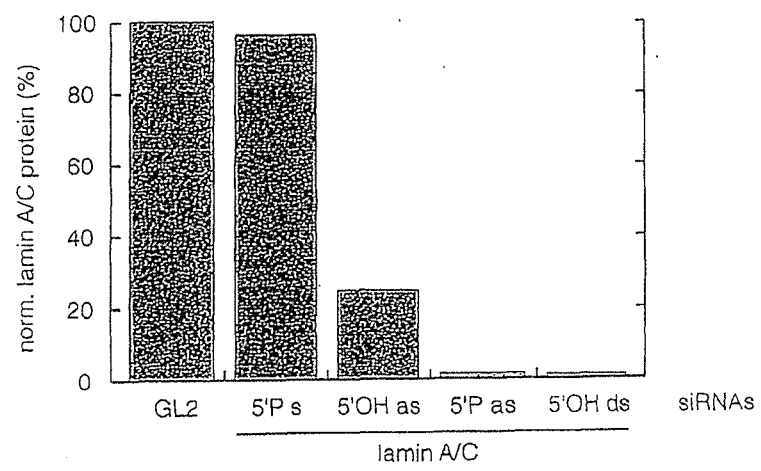

Finally, we tested single-stranded and duplex siRNAs for targeting of an 5 endogenous gene in HeLa cells following our standard protocol previously established for silencing of lamin A/C. 200 nM concentrations of single-stranded siRNAs with and without 5' phosphate and 100 nM concentrations of duplex siRNAs were transfected into HeLa cells. Lamin A/C levels were monitored 48 h later using immunofluorescence (FIG. 8A) and quantitative luminescence-based Western blot analysis (FIG. 8B). Non-phosphorylated antisense siRNA caused a substantial knockdown of lamin A/C to about 25% of its normal level while 5' phosphoryled siRNAs reduced the lamin A/C content to less than 5%, similar to the reduction observed with the lamin A/C 5' phosphorylated (data not shown) or 5 non-phosphorylated duplex siRNA (FIG. 8). Sense siRNA and GL2 unspecific siRNA did not affect lamin A/C levels. The levels of non-targeted vimentin protein were monitored and used for normalizing of the loading of the lanes of the lamin A/C Western blots.

Gene silencing was also observed with phosphorylated as well as non-phosphorylated antisense siRNAs ranging in size between 19 to 29 nt. The phosphorylated antisense siRNAs were consistently better performing than the non-phosphorylated antisense, and their silencing efficiencies were comparable to that of the conventional duplex siRNA (FIG. 11). 5

2.6 Protein Composition of RISC

In order to identify the protein components of the RNA-induced silencing complex (RISC) in HeLa S100 extract, the specific affinity selection previously outlined was used. UV eluates were fractionated on a 5-20% o glycerol gradient, fractions were recovered from the gradient and analysed for protein composition and target RNA endonucleolytic activity.

Two proteins of approximately 100 kDa were identified by mass spectrometry in the peak fraction of the endonucleolytic activity (FIG. 12, fractions 7 and 8), corresponding to eIF2C1 and eIF2C2/GERp95 (FIGS. 13A and B). These proteins are 82% similar and are both members of the Argonaute family (FIG. 13C). The first evidence that Argonaute proteins are part of RISC was provided by classical biochemical fractionation studies using dsRNA-transfected *D. melanogaster* S2 cells (Hammond et al., 2001, supra). The closest relative to *D. melanogaster* Argonaute2, *D. melanogaster* Argonautel, was recently shown to be required for RNAi (Williams and Rubin, PNAS USA 99 (2002), 6889-6894).

Mass spectrometry analysis also revealed the presence of three peptides belonging exclusively to the HILI member of the Argonaute family of proteins. The sequences of those peptides are: NKQDFMDLSICTR, corresponding to positions 17-29 of the protein; TEYVAESFLNCLRR, corresponding to positions 436-449 of the protein, and; YNHDLPARIIVYR, corresponding to positions 591-603 of the protein. This finding suggests that the protein HILI may also be part of RISC.

In human, the Argonaute family is composed of 6 members, eIF2C1, eIF2C2, eIF2C3, eIF2C4, HILI and HIWI (FIG. 14). The alignment of the six predicted amino-acid sequences show a high conservation, in particular between the eIF2C members, and HILI and HIWI (FIG. 15). Predicted cDNA sequences encoding the Argonaute proteins are also shown (FIG. 16).

Figure 17:
Figure 17:

The expression of the human Argonaute proteins was also investigated in HeLa cells by RT-PCR analysis using total and poly (A) selected RNA. All members of the family but HIWI were detected (FIG. 17).

3. Discussion

Figure 3:
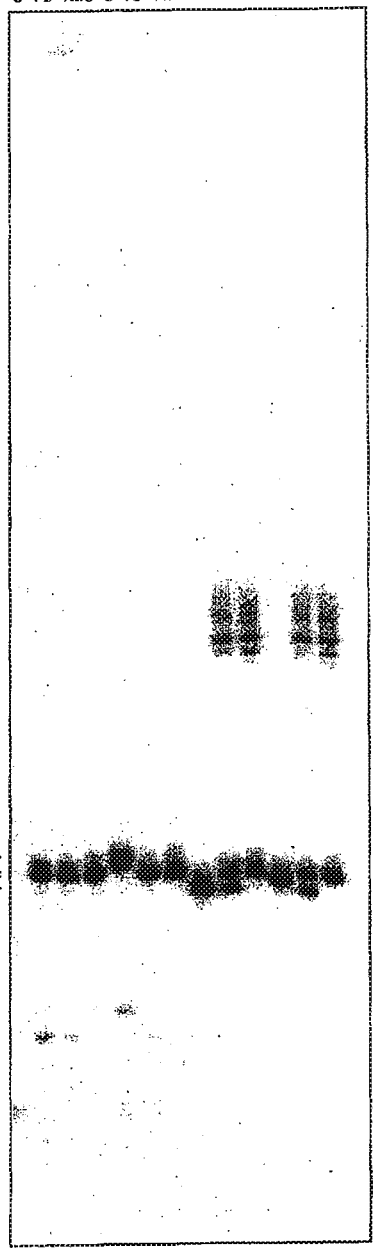
FIG. 3A and FIG. 3B. siRNA containing 3'-terminal phosphates are subjected to ligation as well as dephosphorylation reactions.

The development of a human biochemical system for analysis of the mechanism of RNAi is important given the recent success of siRNA duplexes for silencing genes expressed in human cultured cells and the potential for becoming a sequence-specific therapeutic agent. Biochemical systems are useful for defining the individual steps of the RNAi process and for evaluating the constitution and molecular requirements of the participating macromolecular complexes. For the analysis of RNAi, several systems were developed, with the *D. melanogaster* systems being the most comprehensive as they enable to reconstitute dsRNA processing as well as the mRNA targeting. For mammalian systems, reconstitution of the mRNA targeting reaction has not yet been accomplished. Here, we describe the development and application of a biochemical system prepared from the cytoplasmic fraction of human HeLa cells, which is able to reconstitute the human mRNA-targeting RNA-induced silencing complex (RISC). Formation of RISC was accomplished using either 5' phosphorylated or non-phosphorylated siRNA duplexes; as well as single-stranded antisense siRNAs; non-phosphorylated siRNA duplexes and presumably also single-stranded antisense siRNAs are rapidly 5' phosphorylated in HeLa cell extracts (FIG. 3).

Biochemical Characterization of siRNA Function

Reconstitution of RISC activity was only observed using cytoplasmic HeLa extracts. HeLa nuclear extracts assayed under the same conditions did not support siRNA-specific target RNA cleavage, thus suggesting that RISC components are located predominantly in the cytoplasm (data not shown).

Modifications of the 5' and 3' termini of siRNAs were tested in order to assess the importance of the siRNA termini for the targeting step. It was found that the 5' end modification of the guide siRNA was more inhibitory for target RNA cleavage than 3' end modification. Introduction of the 3' biotin affinity tag into the target-complementary guide siRNA enabled us to affinity select sense-RNA-targeting RISC, whereas 3' biotinylation of the sense siRNA strand resulted in RISC activity in the flowthrough. Furthermore, the single RNA strand composition of RISC was confirmed by reconstituting the sequence-specific endonuclease complex using 5'-phosphorylated single-stranded guide siRNA. The reconstitution of RISC from single-stranded siRNA was however less effective and required 10- to 100-fold higher concentrations compared to duplex siRNA. Reconstitution of RISC from single-stranded siRNA was undetectable using D. melanogaster embryo lysate, which is most likely explained by the high content of 5' to 3' exonucleases in embryo lysate.

The size of RISC in HeLa lysate was determined by gel filtration as well as glycerol gradient ultracentrifugation after streptavidin affinity purification with 3' biotinylated siRNA duplexes. Sizes for RISC in D. melanogaster systems have been reported within a range of less than 230 to 500 kDa, however size determinations were conducted without having affinity purified RISC. Our affinity-purified RISC sediments in a narrow range between the size makers of 66 and 158 kDa. The differences to the reported sizes for RISC are not species-specific as we observed a similar size for RISC in D. melanogaster S2 cell cytoplasmic extracts after affinity purification (data not shown). It has previously been proposed that siRNAs act as primers for target RNA-templated dsRNA synthesis (Lipardi et al., Cell 107 (2001), 297-307) although homologs for such RNA-dependent RNA polymerases known to participate in gene silencing in other systems are not identified in D. melanogaster or mammalian genomes. Analysis of the fate of siRNA duplexes in the HeLa cell system did not provide evidence for such a siRNA-primed activity (FIG. 3), but indicates that the predominant pathway for siRNA-mediated gene silencing is sequence-specific endonucleolytic target RNA degradation.

Single-Stranded 5' Phosphorylated Antisense siRNAs as Triggers of Mammalian Gene Silencing It was previously noted that introduction of sense and antisense RNAs of several hundred nucleotides in length into C. elegans was able to sequence-specifically silence homologous genes (Guo and Kemphues, Cell 81 (1995), 611-620). Later, it was suggested that the sense and antisense RNA preparation were contaminated with a small amount of dsRNA, which was responsible for the silencing effect and is a much more potent inducer of gene silencing (Fire et al. (1998), supra). It is however conceivable that antisense RNA directly contributed to initiation of silencing. Indeed, most recently it was shown that antisense RNAs between 22 and 40 nt, but not sense RNAs were able to activate gene silencing in C. elegans (Tijsterman et al., Science 295 (2002), 694-697). The authors, however, favored the hypothesis of siRNA-primed dsRNA synthesis.

We have shown that modification of the 3' ends of antisense siRNA did not interfere with reconstitution of RISC in the human system. Together, these observations suggest that the driving forces for gene silencing in C. elegans may be predominantly dsRNA synthesis followed by Dicer cleavage, while in human and possibly also in D. melanogaster RISC-specific target mRNA degradation predominates.

Targeting of endogenously expressed lamin A/C by transfection of duplex siRNA into HeLa cells was the first reported example of siRNA-induced gene silencing. Lamin A/C protein was drastically reduced by a lamin A/C-specific siRNA duplex within two days post transfection, while unspecific siRNA duplexes showed no effect. At the time, transfection of non-phosphorylated sense or antisense siRNA did not reveal a substantial effect on lamin A/C levels, although more recently a minor reduction upon antisense siRNA transfection was noticed when similar concentrations of antisense siRNA were delivered as described in this study. However, the effect was not interpreted as RISC-specific effect. Assaying 5'-phosphorylated antisense siRNAs revealed a substantial increase in lamin A/C silencing. Probably, 5' phosphorylated siRNAs are more stable or enter RISC more rapidly. Alternatively, the 5' end of transfected single-stranded siRNA may be less rapidly phosphorylated in the cell in comparison to duplex siRNAs.

Finally, it should be noted that HeLa cells are generally poor in nucleases and represent one of the preferred mammalian systems for studying RNA-processing or transcription reactions in vivo and in vitro. However, it can be expected that 5' phosphorylated single-stranded antisense siRNAs are suitable to knockdown gene expression in other cell types or tissues with a different content of nucleases, since chemical strategies to improve nuclease resistance of single stranded RNA are available. The general silencing ability of various cell types may also depend on the relative levels of siRNA/miRNA-free eIF2C1 and eIF2C2 proteins capable of associating with exogenously delivered siRNAs.

In summary, single-stranded 5'-phosphorylated antisense siRNAs of 19- to 29-nt in size broaden the use of RNA molecules for gene silencing because they can enter the mammalian RNAi pathway in vitro as well as in vivo through reconstitution of RISC. Human eIF2C1 and/or eIF2C2 seem to play a critical role in this process. Considering the feasibility of modulating the stability and uptake properties of single-stranded RNAs, 5'-phosphorylated single-stranded antisense siRNAs may further expand the utility of RNAi-based gene silencing technology as tool for functional genomics as well as therapeutic applications.

Argonaute proteins are a distinct class of proteins, containing a PAZ and Piwi domain (Cerutti et al., 2000, supra) and have been implicated in many processes previously linked to post-transcriptional silencing, however only limited biochemical information is available.

Human eIF2C is the ortholog of rat GERp95, which was identified as a component of the Golgi complex or the endoplasmic reticulum and copurified with intracellular membranes (Cikaluk et al., Mol. Biol. Cell 10 (1999), 3357-3722). More recently, HeLa cell eIF2C2 was shown to be associated with microRNAs and components of the SMN complex, a regulator of ribonucleoprotein assembly, suggesting that eIF2C2 plays a role in miRNA precursor processing or miRNA function (Mourelatos et al., Genes & Dev.16 (2002), 720-728). A more provocative hypothesis is that miRNAs are also in a RISC-like complex, which could potentially mediate target RNA degradation, if only perfectly matched miRNA target mRNAs existed. Sequence analysis using cloned human and mouse, however, did not reveal the presence of such perfectly complementary sequences in the genomes (Lagos-Quintana et al., Science 294 (2001), 853-858). Therefore, miRNPs may only function as translational regulators of partially mismatched target mRNAs, probably by recruiting additional factors that prevent dissociation from mismatched target mRNAs.

Human eIF2C1 has not been linked to gene silencing previously, but it is more than 80% similar in sequence to eIF2C2 (Koesters et al., Genomics 61 (1999), 210-218). This similarity may indicate functional redundancy, but it is also conceivable that functional RISC may contain eIF2C1 and eIF2C2 heterodimers. The predicted molecular weight of this heterodimeric complex would be slightly larger than the observed size of 90-160 kDa, but because size fractionation is based on globular shape, we can not disregard this possibility at this time.

Due to the high conservation between the members of the Argonaute family, it is possible that peptides that derive from regions 100% conserved in the 6 predicted proteins, may belong to members others than eIF2C1 and eIF2C2. In this respect, three peptides were identified with masses corresponding to HILI, meaning that this protein might be also a component of RISC.

To precisely assess the protein composition of RISC, reconstitution of the siRNA-mediated target RNA cleavage must be achieved by using recombinant proteins which may be obtained by cloning and expression in suitable bacterial or eukaryotic systems. We expect that the biochemical characterization or the siRNA-mediated target RNA degradation process will have immediate applications, such as the development of cell lines or transgenic animals overexpressing RISC components. The efficiency in targeting endogenous genes in those lines or organisms will be enhanced. Furthermore, a reconstituted in vitro system for RNAi will allow the design of more potent and specific siRNA to achieve gene silencing.

The invention claimed is:

1. Purified human RISC, wherein said RISC is a ribonucleoprotein complex containing a single stranded RNA component, and wherein said RNA component comprises at least one modified nucleotide analogue which is selected from sugar backbone and nucleobase-modified ribonucleotides and combinations thereof, wherein said RNA component is a single-stranded RNA molecule wherein the single-stranded RNA molecule has a length from 19-29 nucleotides, and wherein said RISC has a molecular weight of less than about 160 kDa.

2. The RISC of claim 1 comprising at least one member of the Argonaute family of proteins.

3. The RISC of claim 2 wherein said at least one member of the Argonaute family of proteins is eIF2C1 and/or eIFC2.

4. The RISC of claim 3, further comprising at least one of eIFC3, eIFC4, HILI or HIWI.

5. The RISC of claim 1, wherein at least the 14-20 5' most nucleotides are substantially complementary to a target transcript.

6. The RISC of claim 1, wherein said RNA molecule has a free 5' hydroxyl moiety or a moiety selected from phosphate groups or analogues thereof.

7. The RISC of claim 6, wherein said RNA molecule has a 5'-moiety selected from the group consisting of 5'-monophosphate ((HO)$_2$(O)P—O-5'), 5'-diphosphate ((HO)$_2$(O)P—O—P(HO)(O)—O-5'), 5'-triphosphate ((HO)$_2$(O)P—O—(HO)(O)P—O—P(HO)(O)—O-5'), 5'-guanosine cap (7-methylated or non-methylated) (7m-G-O-5'-(HO)(O)P—O—(HO)(O)P—O—P(HO)(O)—O-5'), 5'-adenosine cap (Appp), and any modified or unmodified nucleotide cap structure (N—O-5'-(HO)(O)P—O—(HO)(O)P—O—P(HO)(O)—O -5'), 5'-monothiophosphate (phosphorothioate; (HO)$_2$(S)P—O-5'), 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates, 5'-phosphoramidates ((HO)$_2$(O)P—NH-5', (HO)(NH$_2$)(O)P—O-5'), 5'-alkylphosphonates, and 5'-alkyletherphosphonates.

8. The RISC of claim 1, wherein said RNA molecule is completely complementary to said target transcript or completely complementary to said target transcript with the exception of nucleotides that extend beyond position 20 counted from the 5' terminus.

9. The RISC of claim 1, wherein said covalent coupling is via the 3'-terminus of the RNA molecule.

10. A host cell or non-human host organism capable of overexpressing the RISC according to claim 1.

11. A method of enhancing RNAi in a cell or an organism comprising causing said cell or organism to overexpress at least one component of RISC according to claim 1.

12. A composition comprising the RISC according to claim 1 in combination with a pharmaceutical carrier.

13. The RISC according to claim 7, wherein said sulfur replaced monophosphate, diphosphate or triphosphate is 5'-alpha-thiotriphosphate or 5'-gamma-thiotriphosphate, said 5'-alkylphosphonate is RP(OH)(O)—O-5'- or (OH)2(O)P-5'-CH$_2$—), and said 5'-alkyletherphosphonate is RP(OH)(O)—O-5'-.

14. The RISC according to claim 1, wherein the 3' end of said RNA component is stabilized against degradation.

15. The RISC according to claim 14, wherein the 3' end of said RNA component is stabilized against degradation by incorporating non-nucleotide chemical derivatives selected from the group consisting of aminolinkers, thiol linkers, carboxyl linkers, and non-nucleotidic spacers.

16. The RISC according to claim 1, wherein the 3' end of said RNA component is modified with biotin or fluoresceine.

* * * * *

SEQUENCE LISTING

```
<160> NUMBER OF SEQ ID NOS: 115

<210> SEQ ID NO 1
<211> LENGTH: 15
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 1
ucgaaguauu ccgcg                                                    15

<210> SEQ ID NO 2
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 2
ucgaaguauu ccgcguacgu g                                             21

<210> SEQ ID NO 3
<211> LENGTH: 25
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 3
ucgaaguauu ccgcguacgu gaugu                                         25

<210> SEQ ID NO 4
<211> LENGTH: 27
<212> TYPE: RNA
```

```
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 4
ucgaaguauu ccgcguacgu gauguuc                                    27

<210> SEQ ID NO 5
<211> LENGTH: 29
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 5
ucgaaguauu ccgcguacgu gauguucac                                  29

<210> SEQ ID NO 6
<211> LENGTH: 15
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 6
ucgaaguauu ccgcg                                                 15

<210> SEQ ID NO 7
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 7
ucgaaguauu ccgcguacgu g                                          21

<210> SEQ ID NO 8
<211> LENGTH: 25
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 8
ucgaaguauu ccgcguacgu gaugu                                      25

<210> SEQ ID NO 9
<211> LENGTH: 27
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 9
ucgaaguauu ccgcguacgu gauguuc                                    27
```

```
<210> SEQ ID NO 10
<211> LENGTH: 29
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 10
ucgaaguauu ccgcguacgu gauguucac                                          29

<210> SEQ ID NO 11
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 11
ucgaaguauu ccgcguacgu g                                                  21

<210> SEQ ID NO 12
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (20)..(20)
<223> OTHER INFORMATION: n = 2'-deoxythymidine
<220> FEATURE:
<221> NAME/KEY: misc_feature
<222> LOCATION: (21)..(21)
<223> OTHER INFORMATION: n = 2'-deoxyguanosine

<400> SEQUENCE: 12
ucgaaguauu ccgcguacgn n                                                  21

<210> SEQ ID NO 13
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 13
ucgaaguauu ccgcguacgu u                                                  21

<210> SEQ ID NO 14
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
```

```
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (20)..(21)
<223> OTHER INFORMATION: n = 2'-deoxythymidine

<400> SEQUENCE: 14
ucgaaguauu ccgcguacgn n                                          21

<210> SEQ ID NO 15
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 15
ucgaaguauu ccgcguacgu g                                          21

<210> SEQ ID NO 16
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100 cells
      antisense siRNA (5'-3')
<220> FEATURE:
<221> NAME/KEY: misc_feature
<222> LOCATION: (20)..(20)
<223> OTHER INFORMATION: n = 2'-deoxythymidine
<220> FEATURE:
<221> NAME/KEY: misc_feature
<222> LOCATION: (21)..(21)
<223> OTHER INFORMATION: n = 2'-deoxyguanosine

<400> SEQUENCE: 16
ucgaaguauu ccgcguacgn n                                          21

<210> SEQ ID NO 17
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 17
ucgaaguauu ccgcguacgu u                                          21

<210> SEQ ID NO 18
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
```

```
<220> FEATURE:
<221> NAME/KEY: misc_feature
<222> LOCATION: (20)..(21)
<223> OTHER INFORMATION: n = 2'-deoxythymidine

<400> SEQUENCE: 18
ucgaaguauu ccgcguacgn n                                              21

<210> SEQ ID NO 19
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      sense siRNA (5'-3')

<400> SEQUENCE: 19
cguacgcgga auacuucgaa a                                              21

<210> SEQ ID NO 20
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 20
ucgaaguauu ccgcguacgu g                                              21

<210> SEQ ID NO 21
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      sense siRNA (5'-3')

<400> SEQUENCE: 21
cguacgcgga auacuucgaa a                                              21

<210> SEQ ID NO 22
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (20)..(20)
<223> OTHER INFORMATION: n = 2'-deoxythymidine
<220> FEATURE:
<221> NAME/KEY: misc_feature
<222> LOCATION: (21)..(21)
<223> OTHER INFORMATION: n = 2'-deoxyguanosine

<400> SEQUENCE: 22
ucgaaguauu ccgcguacgn n                                              21

<210> SEQ ID NO 23
```

```
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      sense siRNA (5'-3')

<400> SEQUENCE: 23
cguacgcgga auacuucgaa a                                              21

<210> SEQ ID NO 24
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      antisense siRNA (5'-3')

<400> SEQUENCE: 24
ucgaaguauu ccgcguacgu u                                              21

<210> SEQ ID NO 25
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      sense siRNA (5'-3')

<400> SEQUENCE: 25
cguacgcgga auacuucgaa a                                              21

<210> SEQ ID NO 26
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (20)..(21)
<223> OTHER INFORMATION: n = 2'-deoxythymidine

<400> SEQUENCE: 26
ucgaaguauu ccgcguacgn n                                              21

<210> SEQ ID NO 27
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (1)..(1)
<223> OTHER INFORMATION: n = 2'-deoxythymidine
```

```
<400> SEQUENCE: 27
ncgaaguauu ccgcguacgu u                                              21

<210> SEQ ID NO 28
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      sense siRNA (5'-3')
<220> FEATURE:
<221> NAME/KEY: misc_feature
<222> LOCATION: (1)..(1)
<223> OTHER INFORMATION: n = 2'-deoxycytidine

<400> SEQUENCE: 28
nguacgcgga auacuucgau u                                              21

<210> SEQ ID NO 29
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (1)..(1)
<223> OTHER INFORMATION: n = 2'-deoxythymidine

<400> SEQUENCE: 29
ncgaaguauu ccgcguacgu u                                              21

<210> SEQ ID NO 30
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100 cells
      antisense siRNA (5'-3')
<220> FEATURE:
<221> NAME/KEY: misc_feature
<222> LOCATION: (1)..(21)
<223> OTHER INFORMATION: n = 2'-deoxythymidine

<400> SEQUENCE: 30
ncgaaguauu ccgcguacgn n                                              21

<210> SEQ ID NO 31
<211> LENGTH: 21
<212> TYPE: DNA
<213> ORGANISM: Homo sapiens
<220> FEATURE:
<221> NAME/KEY: misc_feature
<222> LOCATION: (1)..(21)
```

```
<223> OTHER INFORMATION: RNA/DNA hybrid
<220> FEATURE:
<221> NAME/KEY: misc_feature
<223> OTHER INFORMATION: HeLa S100
      sense siRNA (5'-3')
<220> FEATURE:
<221> NAME/KEY: misc_feature
<222> LOCATION: (1)..(1)
<223> OTHER INFORMATION: n = 2'-deoxycytidine
<220> FEATURE:
<221> NAME/KEY: misc_feature
<222> LOCATION: (20)..(21)
<223> OTHER INFORMATION: n = 2'-deoxythymidine

<400> SEQUENCE: 31
nguacgcgga auacuucgan n                                              21

<210> SEQ ID NO 32
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (1)..(21)
<223> OTHER INFORMATION: n = 2'-deoxythymidine

<400> SEQUENCE: 32
ncgaaguauu ccgcguacgn n                                              21

<210> SEQ ID NO 33
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: RNA/DNA hybrid
<220> FEATURE:
<221> NAME/KEY: misc_feature
<223> OTHER INFORMATION: HeLa S100
      antisense siRNA (5'-3')
<220> FEATURE:
<221> NAME/KEY: misc_feature
<222> LOCATION: (1)..(21)
<223> OTHER INFORMATION: n = 2'-deoxythymidine

<400> SEQUENCE: 33
ncgaaguauu ccgcguacgn n                                              21

<210> SEQ ID NO 34
<211> LENGTH: 13
<212> TYPE: PRT
<213> ORGANISM: Homo sapiens
<220> FEATURE:
<221> NAME/KEY: MISC_FEATURE
<223> OTHER INFORMATION: peptide fragment of HILI, corresponding to
      position 17-29 of the protein

<400> SEQUENCE: 34

Asn Lys Gln Asp Phe Met Asp Leu Ser Ile Cys Thr Arg
1               5                   10

<210> SEQ ID NO 35
```

```
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of HILI, corresponding to
      position 436-449 of the protein

<400> SEQUENCE: 35

Thr Glu Tyr Val Ala Glu Ser Phe Leu Asn Cys Leu Arg Arg
1               5                   10

<210> SEQ ID NO 36
<211> LENGTH: 13
<212> TYPE: PRT
<213> ORGANISM: Homo sapiens
<220> FEATURE:
<221> NAME/KEY: MISC_FEATURE
<223> OTHER INFORMATION: peptide fragment of HILI, corresponding to
      position 591-603 of the protein

<400> SEQUENCE: 36

Tyr Asn His Asp Leu Pro Ala Arg Ile Ile Val Tyr Arg
1               5                   10

<210> SEQ ID NO 37
<211> LENGTH: 35
<212> TYPE: RNA
<213> ORGANISM: Homo sapiens
<220> FEATURE:
<221> NAME/KEY: misc_feature
<223> OTHER INFORMATION: HeLa S100
      target RNA

<400> SEQUENCE: 37
aacaucacgu acgcggaaua cuucgaaaug uccgu                                  35

<210> SEQ ID NO 38
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      strand of siRNA duplex

<400> SEQUENCE: 38
cguacgcgga auacuucgau u                                                 21

<210> SEQ ID NO 39
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      strand of siRNA duplex

<400> SEQUENCE: 39
ucgaaguauu ccgcguacgu u                                                 21

<210> SEQ ID NO 40
<211> LENGTH: 21
<212> TYPE: RNA
<213> ORGANISM: Homo sapiens
<220> FEATURE:
<221> NAME/KEY: misc_feature
<223> OTHER INFORMATION: HeLa S100
      strand of siRNA duplex
```

```
<400> SEQUENCE: 40
cguacgcgga auacuucgaa a                                              21

<210> SEQ ID NO 41
<211> LENGTH: 20
<212> TYPE: RNA
<213> ORGANISM: Homo sapiens
<220> FEATURE:
<221> NAME/KEY: misc_feature
<223> OTHER INFORMATION: HeLa S100
      strand of siRNA duplex

<400> SEQUENCE: 41
ucgaaguauu ccgcguacgu                                                20

<210> SEQ ID NO 42
<211> LENGTH: 12
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 42

Val Leu Gln Pro Pro Ser Ile Leu Tyr Gly Gly Arg
1               5                   10

<210> SEQ ID NO 43
<211> LENGTH: 12
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 43

Gln Glu Ile Ile Gln Asp Leu Ala Ala Met Val Arg
1               5                   10

<210> SEQ ID NO 44
<211> LENGTH: 12
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 44

His Leu Pro Ser Met Arg Tyr Thr Pro Val Gly Arg
1               5                   10

<210> SEQ ID NO 45
<211> LENGTH: 12
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 45

Lys Leu Thr Asp Asn Gln Thr Ser Thr Met Ile Arg
1               5                   10
```

```
<210> SEQ ID NO 46
<211> LENGTH: 13
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 46

Tyr Ala Gln Gly Ala Asp Ser Val Glu Pro Met Phe Arg
1               5                   10

<210> SEQ ID NO 47
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 47

Asp Lys Val Glu Leu Glu Val Thr Leu Pro Gly Glu Gly Lys
1               5                   10

<210> SEQ ID NO 48
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 48

Asp Ala Gly Met Pro Ile Gln Gly Gln Pro Cys Phe Cys Lys
1               5                   10

<210> SEQ ID NO 49
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 49

Thr Gln Ile Phe Gly Asp Arg Lys Pro Val Phe Asp Gly Arg
1               5                   10

<210> SEQ ID NO 50
<211> LENGTH: 15
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 50

Ala Thr Ala Arg Ser Ala Pro Asp Arg Gln Glu Glu Ile Ser Lys
1               5                   10                  15

<210> SEQ ID NO 51
<211> LENGTH: 14
<212> TYPE: PRT
```

```
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 51

Asp Tyr Gln Pro Gly Ile Thr Phe Ile Val Val Gln Lys Arg
1               5                   10

<210> SEQ ID NO 52
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 52

Ser Ala Pro Asp Arg Gln Glu Glu Ile Ser Lys Leu Met Arg
1               5                   10

<210> SEQ ID NO 53
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 53

Tyr Pro His Leu Pro Cys Leu Gln Val Gly Gln Glu Gln Lys
1               5                   10

<210> SEQ ID NO 54
<211> LENGTH: 17
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 54

Ser Phe Phe Thr Ala Ser Glu Gly Cys Ser Asn Pro Leu Gly Gly Gly
1               5                   10                  15

Arg

<210> SEQ ID NO 55
<211> LENGTH: 23
<212> TYPE: PRT
<213> ORGANISM: Homo sapiens
<220> FEATURE:
<221> NAME/KEY: MISC_FEATURE
<223> OTHER INFORMATION: peptide fragment of eIF2C2, obtained by mass
      spectrometry

<400> SEQUENCE: 55

Tyr His Leu Val Asp Lys Glu His Asp Ser Ala Glu Gly Ser His Thr
1               5                   10                  15

Ser Gly Gln Ser Asn Gly Arg
            20

<210> SEQ ID NO 56
<211> LENGTH: 12
```

```
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 56

Val Leu Pro Ala Pro Ile Leu Gln Tyr Gly Gly Arg
1               5                   10

<210> SEQ ID NO 57
<211> LENGTH: 12
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 57

Ser Val Ser Ile Pro Ala Pro Ala Tyr Tyr Ala Arg
1               5                   10

<210> SEQ ID NO 58
<211> LENGTH: 12
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 58

Thr Ser Pro Gln Thr Leu Ser Asn Leu Cys Leu Lys
1               5                   10

<210> SEQ ID NO 59
<211> LENGTH: 13
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 59

Tyr Ala Gln Gly Ala Asp Ser Val Glu Pro Met Phe Arg
1               5                   10

<210> SEQ ID NO 60
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 60

Asn Ile Tyr Thr Val Thr Ala Leu Pro Ile Gly Asn Glu Arg
1               5                   10

<210> SEQ ID NO 61
<211> LENGTH: 14
<212> TYPE: PRT
<213> ORGANISM: Homo sapiens
<220> FEATURE:
<221> NAME/KEY: MISC_FEATURE
```

```
<223> OTHER INFORMATION: peptide fragment of eIF2C1, obtained by mass
      spectrometry

<400> SEQUENCE: 61

Val Asp Phe Glu Val Thr Ile Pro Gly Glu Gly Lys Asp Arg
1               5                   10

<210> SEQ ID NO 62
<211> LENGTH: 14
<212> TYPE: PRT
<213> ORGANISM: Homo sapiens
<220> FEATURE:
<221> NAME/KEY: MISC_FEATURE
<223> OTHER INFORMATION: HeLa S100 cells
      peptide fragment of eIF2C1 obtained by mass spectrometry

<400> SEQUENCE: 62

Asp Ala Gly Met Pro Ile Gln Gly Gln Pro Cys Phe Cys Lys
1               5                   10

<210> SEQ ID NO 63
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 63

Asn Ile Asp Glu Gln Pro Lys Pro Leu Thr Asp Ser Gln Arg
1               5                   10

<210> SEQ ID NO 64
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 64

Ser Ala Pro Asp Arg Gln Glu Glu Ile Ser Arg Leu Met Lys
1               5                   10

<210> SEQ ID NO 65
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 65

Asp Tyr Gln Pro Gly Ile Thr Tyr Ile Val Val Gln Lys Arg
1               5                   10

<210> SEQ ID NO 66
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 66
```

Tyr Pro His Leu Pro Cys Leu Gln Val Gly Gln Glu Gln Lys
1               5                  10

<210> SEQ ID NO 67
<211> LENGTH: 17
<212> TYPE: PRT
<213> ORGANISM: Homo sapiens
<220> FEATURE:
<221> NAME/KEY: MISC_FEATURE
<223> OTHER INFORMATION: peptide fragment of eIF2C1, obtained by mass
      spectrometry

<400> SEQUENCE: 67

Ser Phe Phe Ser Pro Pro Glu Gly Tyr Tyr His Pro Leu Gly Gly Gly
1               5                  10                  15

Arg

<210> SEQ ID NO 68
<211> LENGTH: 857
<212> TYPE: PRT
<213> ORGANISM: Homo sapiens
<220> FEATURE:
<221> NAME/KEY: MISC_FEATURE
<223> OTHER INFORMATION: eIF2C1, predicted protein sequence

<400> SEQUENCE: 68

Met Glu Ala Gly Pro Ser Gly Ala Ala Gly Ala Tyr Leu Pro Pro
1               5                  10                  15

Leu Gln Gln Val Phe Gln Ala Pro Arg Arg Pro Gly Ile Gly Thr Val
                20                  25                  30

Gly Lys Pro Ile Lys Leu Leu Ala Asn Tyr Phe Glu Val Asp Ile Pro
            35                  40                  45

Lys Ile Asp Val Tyr His Tyr Glu Val Asp Ile Lys Pro Asp Lys Cys
        50                  55                  60

Pro Arg Arg Val Asn Arg Glu Val Val Glu Tyr Met Val Gln His Phe
65                  70                  75                  80

Lys Pro Gln Ile Phe Gly Asp Arg Lys Pro Val Tyr Asp Gly Lys Lys
                85                  90                  95

Asn Ile Tyr Thr Val Thr Ala Leu Pro Ile Gly Asn Glu Arg Val Asp
            100                 105                 110

Phe Glu Val Thr Ile Pro Gly Glu Gly Lys Asp Arg Ile Phe Lys Val
        115                 120                 125

Ser Ile Lys Trp Leu Ala Ile Val Ser Trp Arg Met Leu His Glu Ala
    130                 135                 140

Leu Val Ser Gly Gln Ile Pro Val Pro Leu Glu Ser Val Gln Ala Leu
145                 150                 155                 160

Asp Val Ala Met Arg His Leu Ala Ser Met Arg Tyr Thr Pro Val Gly
                165                 170                 175

Arg Ser Phe Phe Ser Pro Pro Glu Gly Tyr Tyr His Pro Leu Gly Gly
            180                 185                 190

Gly Arg Glu Val Trp Phe Gly Phe His Gln Ser Val Arg Pro Ala Met
        195                 200                 205

Trp Lys Met Met Leu Asn Ile Asp Val Ser Ala Thr Ala Phe Tyr Lys
    210                 215                 220

Ala Gln Pro Val Ile Glu Phe Met Cys Glu Val Leu Asp Ile Arg Asn
225                 230                 235                 240

Ile Asp Glu Gln Pro Lys Pro Leu Thr Asp Ser Gln Arg Val Arg Phe
                245                 250                 255

-continued

Thr Lys Glu Ile Lys Gly Leu Lys Val Glu Val Thr His Cys Gly Gln
                260                 265                 270

Met Lys Arg Lys Tyr Arg Val Cys Asn Val Thr Arg Pro Ala Ser
            275                 280                 285

His Gln Thr Phe Pro Leu Gln Leu Glu Ser Gly Gln Thr Val Glu Cys
        290                 295                 300

Thr Val Ala Gln Tyr Phe Lys Gln Lys Tyr Asn Leu Gln Leu Lys Tyr
305                 310                 315                 320

Pro His Leu Pro Cys Leu Gln Val Gly Gln Glu Gln Lys His Thr Tyr
                325                 330                 335

Leu Pro Leu Glu Val Cys Asn Ile Val Ala Gly Gln Arg Cys Ile Lys
                340                 345                 350

Lys Leu Thr Asp Asn Gln Thr Ser Thr Met Ile Lys Ala Thr Ala Arg
            355                 360                 365

Ser Ala Pro Asp Arg Gln Glu Glu Ile Ser Arg Leu Met Lys Asn Ala
370                 375                 380

Ser Tyr Asn Leu Asp Pro Tyr Ile Gln Glu Phe Gly Ile Lys Val Lys
385                 390                 395                 400

Asp Asp Met Thr Glu Val Thr Gly Arg Val Leu Pro Ala Pro Ile Leu
                405                 410                 415

Gln Tyr Gly Gly Arg Asn Arg Ala Ile Ala Thr Pro Asn Gln Gly Val
            420                 425                 430

Trp Asp Met Arg Gly Lys Gln Phe Tyr Asn Gly Ile Glu Ile Lys Val
            435                 440                 445

Trp Ala Ile Ala Cys Phe Ala Pro Gln Lys Gln Cys Arg Glu Glu Val
        450                 455                 460

Leu Lys Asn Phe Thr Asp Gln Leu Arg Lys Ile Ser Lys Asp Ala Gly
465                 470                 475                 480

Met Pro Ile Gln Gly Gln Pro Cys Phe Cys Lys Tyr Ala Gln Gly Ala
                485                 490                 495

Asp Ser Val Glu Pro Met Phe Arg His Leu Lys Asn Thr Tyr Ser Gly
            500                 505                 510

Leu Gln Leu Ile Ile Val Ile Leu Pro Gly Lys Thr Pro Val Tyr Ala
        515                 520                 525

Glu Val Lys Arg Val Gly Asp Thr Leu Leu Gly Met Ala Thr Gln Cys
530                 535                 540

Val Gln Val Lys Asn Val Val Lys Thr Ser Pro Gln Thr Leu Ser Asn
545                 550                 555                 560

Leu Cys Leu Lys Ile Asn Val Lys Leu Gly Ile Asn Asn Ile Leu
                565                 570                 575

Val Pro His Gln Arg Ser Ala Val Phe Gln Gln Pro Val Ile Phe Leu
            580                 585                 590

Gly Ala Asp Val Thr His Pro Pro Ala Gly Asp Gly Lys Lys Pro Ser
        595                 600                 605

Ile Thr Ala Val Val Gly Ser Met Asp Ala His Pro Ser Arg Tyr Cys
        610                 615                 620

Ala Thr Val Arg Val Gln Arg Pro Arg Gln Glu Ile Ile Glu Asp Leu
625                 630                 635                 640

Ser Tyr Met Val Arg Glu Leu Leu Ile Gln Phe Tyr Lys Ser Thr Arg
                645                 650                 655

Phe Lys Pro Thr Arg Ile Ile Phe Tyr Arg Asp Gly Val Pro Glu Gly
            660                 665                 670

-continued

```
Gln Leu Pro Gln Ile Leu His Tyr Glu Leu Ala Ile Arg Asp Ala
            675                 680                 685

Cys Ile Lys Leu Glu Lys Asp Tyr Gln Pro Gly Ile Thr Tyr Ile Val
690                 695                 700

Val Gln Lys Arg His His Thr Arg Leu Phe Cys Ala Asp Lys Asn Glu
705                 710                 715                 720

Arg Ile Gly Lys Ser Gly Asn Ile Pro Ala Gly Thr Thr Val Asp Thr
                725                 730                 735

Asn Ile Thr His Pro Phe Glu Phe Phe Tyr Leu Cys Ser His Ala
                740                 745                 750

Gly Ile Gln Gly Thr Ser Arg Pro Ser His Tyr Tyr Val Leu Trp Asp
            755                 760                 765

Asp Asn Arg Phe Thr Ala Asp Glu Leu Gln Ile Leu Thr Tyr Gln Leu
770                 775                 780

Cys His Thr Tyr Val Arg Cys Thr Arg Ser Val Ser Ile Pro Ala Pro
785                 790                 795                 800

Ala Tyr Tyr Ala Arg Leu Val Ala Phe Arg Ala Arg Tyr His Leu Val
                805                 810                 815

Asp Lys Glu His Asp Ser Gly Glu Gly Ser His Ile Ser Gly Gln Ser
                820                 825                 830

Asn Gly Arg Asp Pro Gln Ala Leu Ala Lys Ala Val Gln Val His Gln
            835                 840                 845

Asp Thr Leu Arg Thr Met Tyr Phe Ala
        850                 855

<210> SEQ ID NO 69
<211> LENGTH: 860
<212> TYPE: PRT
<213> ORGANISM: Homo sapiens
<220> FEATURE:
<221> NAME/KEY: MISC_FEATURE
<223> OTHER INFORMATION: eIF2C2, predicted protein sequence

<400> SEQUENCE: 69

Met Gly Val Leu Ser Ala Ile Pro Ala Leu Ala Pro Pro Ala Pro Pro
1               5                   10                  15

Pro Pro Ile Gln Gly Tyr Ala Phe Lys Pro Pro Arg Pro Asp Phe
                20                  25                  30

Gly Thr Ser Gly Arg Thr Ile Lys Leu Gln Ala Asn Phe Phe Glu Met
            35                  40                  45

Asp Ile Pro Lys Ile Asp Ile Tyr His Tyr Glu Leu Asp Ile Lys Pro
50                  55                  60

Glu Lys Cys Pro Arg Arg Val Asn Arg Glu Ile Val Glu His Met Val
65                  70                  75                  80

Gln His Phe Lys Thr Gln Ile Phe Gly Asp Arg Lys Pro Val Phe Asp
                85                  90                  95

Gly Arg Lys Asn Leu Tyr Thr Ala Met Pro Leu Pro Ile Gly Arg Asp
            100                 105                 110

Lys Val Glu Leu Glu Val Thr Leu Pro Gly Glu Gly Lys Asp Arg Ile
        115                 120                 125

Phe Lys Val Ser Ile Lys Trp Val Ser Cys Val Ser Leu Gln Ala Leu
    130                 135                 140

His Asp Ala Leu Ser Gly Arg Leu Pro Ser Val Pro Phe Glu Thr Ile
145                 150                 155                 160

Gln Ala Leu Asp Val Val Met Arg His Leu Pro Ser Met Arg Tyr Thr
                165                 170                 175
```

```
Pro Val Gly Arg Ser Phe Phe Thr Ala Ser Glu Gly Cys Ser Asn Pro
            180                 185                 190

Leu Gly Gly Gly Arg Glu Val Trp Phe Gly Phe His Gln Ser Val Arg
        195                 200                 205

Pro Ser Leu Trp Lys Met Met Leu Asn Ile Asp Val Ser Ala Thr Ala
210                 215                 220

Phe Tyr Lys Ala Gln Pro Val Ile Glu Phe Val Cys Glu Val Leu Asp
225                 230                 235                 240

Phe Lys Ser Ile Glu Glu Gln Lys Pro Leu Thr Asp Ser Gln Arg
            245                 250                 255

Val Lys Phe Thr Lys Glu Ile Lys Gly Leu Lys Val Glu Ile Thr His
            260                 265                 270

Cys Gly Gln Met Lys Arg Lys Tyr Arg Val Cys Asn Val Thr Arg Arg
            275                 280                 285

Pro Ala Ser His Gln Thr Phe Pro Leu Gln Gln Glu Ser Gly Gln Thr
            290                 295                 300

Val Glu Cys Thr Val Ala Gln Tyr Phe Lys Asp Arg His Lys Leu Val
305                 310                 315                 320

Leu Arg Tyr Pro His Leu Pro Cys Leu Gln Val Gly Gln Glu Gln Lys
                325                 330                 335

His Thr Tyr Leu Pro Leu Glu Val Cys Asn Ile Val Ala Gly Gln Arg
                340                 345                 350

Cys Ile Lys Lys Leu Thr Asp Asn Gln Thr Ser Thr Met Ile Arg Ala
            355                 360                 365

Thr Ala Arg Ser Ala Pro Asp Arg Gln Glu Glu Ile Ser Lys Leu Met
            370                 375                 380

Arg Ser Ala Ser Phe Asn Thr Asp Pro Tyr Val Arg Glu Phe Gly Ile
385                 390                 395                 400

Met Val Lys Asp Glu Met Thr Asp Val Thr Gly Arg Val Leu Gln Pro
                405                 410                 415

Pro Ser Ile Leu Tyr Gly Gly Arg Asn Lys Ala Ile Ala Thr Pro Val
            420                 425                 430

Gln Gly Val Trp Asp Met Arg Asn Lys Gln Phe His Thr Gly Ile Glu
            435                 440                 445

Ile Lys Val Trp Ala Ile Ala Cys Phe Ala Pro Gln Arg Gln Cys Thr
            450                 455                 460

Glu Val His Leu Lys Ser Phe Thr Glu Gln Leu Arg Lys Ile Ser Arg
465                 470                 475                 480

Asp Ala Gly Met Pro Ile Gln Gly Gln Pro Cys Phe Cys Lys Tyr Ala
                485                 490                 495

Gln Gly Ala Asp Ser Val Glu Pro Met Phe Arg His Leu Lys Asn Thr
            500                 505                 510

Tyr Ala Gly Leu Gln Leu Val Val Ile Leu Pro Gly Lys Thr Pro
            515                 520                 525

Val Tyr Ala Glu Val Lys Arg Val Gly Asp Thr Val Leu Gly Met Ala
            530                 535                 540

Thr Gln Cys Val Gln Met Lys Asn Val Gln Arg Thr Thr Pro Gln Thr
545                 550                 555                 560

Leu Ser Asn Leu Cys Leu Lys Ile Asn Val Lys Leu Gly Gly Val Asn
                565                 570                 575

Asn Ile Leu Leu Pro Gln Gly Arg Pro Pro Val Phe Gln Gln Pro Val
            580                 585                 590
```

Ile Phe Leu Gly Ala Asp Val Thr His Pro Ala Gly Asp Gly Lys
            595                 600                 605

Lys Pro Ser Ile Ala Ala Val Gly Ser Met Asp Ala His Pro Asn
        610                 615                 620

Arg Tyr Cys Ala Thr Val Arg Val Gln Gln His Arg Gln Glu Ile Ile
625                 630                 635                 640

Gln Asp Leu Ala Ala Met Val Arg Glu Leu Leu Ile Gln Phe Tyr Lys
                645                 650                 655

Ser Thr Arg Phe Lys Pro Thr Arg Ile Ile Phe Tyr Arg Asp Gly Val
            660                 665                 670

Ser Glu Gly Gln Phe Gln Gln Val Leu His His Glu Leu Leu Ala Ile
        675                 680                 685

Arg Glu Ala Cys Ile Lys Leu Glu Lys Asp Tyr Gln Pro Gly Ile Thr
    690                 695                 700

Phe Ile Val Val Gln Lys Arg His His Thr Arg Leu Phe Cys Thr Asp
705                 710                 715                 720

Lys Asn Glu Arg Val Gly Lys Ser Gly Asn Ile Pro Ala Gly Thr Thr
                725                 730                 735

Val Asp Thr Lys Ile Thr His Pro Thr Glu Phe Asp Phe Tyr Leu Cys
            740                 745                 750

Ser His Ala Gly Ile Gln Gly Thr Ser Arg Pro Ser His Tyr His Val
        755                 760                 765

Leu Trp Asp Asp Asn Arg Phe Ser Ser Asp Glu Leu Gln Ile Leu Thr
    770                 775                 780

Tyr Gln Leu Cys His Thr Tyr Val Arg Cys Thr Arg Ser Val Ser Ile
785                 790                 795                 800

Pro Ala Pro Ala Tyr Tyr Ala His Leu Val Ala Phe Arg Ala Arg Tyr
                805                 810                 815

His Leu Val Asp Lys Glu His Asp Ser Ala Glu Gly Ser His Thr Ser
            820                 825                 830

Gly Gln Ser Asn Gly Arg Asp His Gln Ala Leu Ala Lys Ala Val Gln
        835                 840                 845

Val His Gln Asp Thr Leu Arg Thr Met Tyr Phe Ala
    850                 855                 860

<210> SEQ ID NO 70
<211> LENGTH: 924
<212> TYPE: PRT
<213> ORGANISM: Homo sapiens
<220> FEATURE:
<221> NAME/KEY: MISC_FEATURE
<223> OTHER INFORMATION: eIF2C3, predicted protein sequence

<400> SEQUENCE: 70

Ser Arg Ser Arg Val Pro Val Pro Gly Pro Gly Ala Ala Ala Ala Pro
1               5                   10                  15

Cys Pro Ala Pro Ala Ser Pro Arg Arg His Pro Ser Ala Asn Ile Pro
                20                  25                  30

Glu Ile Lys Arg Tyr Ala Ala Ala Ala Ala Ala Ala Gly Pro Gly
            35                  40                  45

Ala Gly Gly Ala Gly Asp Arg Gly Glu Ala Ala Pro Ala Ala Ala Met
        50                  55                  60

Glu Ala Leu Gly Pro Gly Pro Pro Ala Ser Leu Phe Gln Pro Pro Arg
65                  70                  75                  80

Arg Pro Gly Leu Gly Thr Val Gly Lys Pro Ile Arg Leu Leu Ala Asn
                85                  90                  95

```
His Phe Gln Val Gln Ile Pro Lys Ile Asp Val Tyr His Tyr Asp Val
                100                 105                 110

Asp Ile Lys Pro Glu Lys Arg Pro Arg Arg Val Asn Arg Glu Val Val
            115                 120                 125

Asp Thr Met Val Arg His Phe Lys Met Gln Ile Phe Gly Asp Arg Gln
        130                 135                 140

Pro Gly Tyr Asp Gly Lys Arg Asn Met Tyr Thr Ala His Pro Leu Pro
145                 150                 155                 160

Ile Gly Arg Asp Arg Val Asp Met Glu Val Thr Leu Pro Gly Glu Gly
                165                 170                 175

Lys Asp Gln Thr Phe Lys Val Ser Val Gln Trp Val Ser Val Val Ser
            180                 185                 190

Leu Gln Leu Leu Leu Glu Ala Leu Ala Gly His Leu Asn Glu Val Pro
        195                 200                 205

Asp Asp Ser Val Gln Ala Leu Asp Val Ile Thr Arg His Leu Pro Ser
210                 215                 220

Met Arg Tyr Thr Pro Val Gly Arg Ser Phe Phe Ser Pro Pro Glu Gly
225                 230                 235                 240

Tyr Tyr His Pro Leu Gly Gly Gly Arg Glu Val Trp Phe Gly Phe His
                245                 250                 255

Gln Ser Val Arg Pro Ala Met Trp Asn Met Met Leu Asn Ile Asp Val
            260                 265                 270

Ser Ala Thr Ala Phe Tyr Arg Ala Gln Pro Ile Ile Glu Phe Met Cys
        275                 280                 285

Glu Val Leu Asp Ile Gln Asn Ile Asn Glu Gln Thr Lys Pro Leu Thr
        290                 295                 300

Asp Ser Gln Arg Val Lys Phe Thr Lys Glu Ile Arg Gly Leu Lys Val
305                 310                 315                 320

Glu Val Thr His Cys Gly Gln Met Lys Arg Lys Tyr Arg Val Cys Asn
                325                 330                 335

Val Thr Arg Arg Pro Ala Ser His Gln Thr Phe Pro Leu Gln Leu Glu
            340                 345                 350

Asn Gly Gln Ala Met Glu Cys Thr Val Ala Gln Tyr Phe Lys Gln Lys
        355                 360                 365

Tyr Ser Leu Gln Leu Lys Tyr Pro His Leu Pro Cys Leu Gln Val Gly
370                 375                 380

Gln Glu Gln Lys His Thr Tyr Leu Pro Leu Glu Val Cys Asn Ile Val
385                 390                 395                 400

Ala Gly Gln Arg Cys Ile Lys Lys Leu Thr Asp Asn Gln Thr Ser Thr
                405                 410                 415

Met Ile Lys Ala Thr Ala Arg Ser Ala Pro Asp Arg Gln Glu Glu Ile
            420                 425                 430

Ser Arg Leu Val Lys Ser Asn Ser Met Val Gly Gly Pro Asp Pro Tyr
        435                 440                 445

Leu Lys Glu Phe Gly Ile Val Val His Asn Glu Met Thr Glu Leu Thr
        450                 455                 460

Gly Arg Val Leu Pro Ala Pro Met Leu Gln Tyr Gly Gly Arg Asn Lys
465                 470                 475                 480

Thr Val Ala Thr Pro Asn Gln Gly Val Trp Asp Met Arg Gly Lys Gln
                485                 490                 495

Phe Tyr Ala Gly Ile Glu Ile Lys Val Trp Ala Val Ala Cys Phe Ala
            500                 505                 510
```

```
Pro Gln Lys Gln Cys Arg Glu Asp Leu Leu Lys Ser Phe Thr Asp Gln
            515                 520                 525

Leu Arg Lys Ile Ser Lys Asp Ala Gly Met Pro Ile Gln Gly Gln Pro
530                 535                 540

Cys Phe Cys Lys Tyr Ala Gln Gly Ala Asp Ser Val Glu Pro Met Phe
545                 550                 555                 560

Lys His Leu Lys Met Thr Tyr Val Gly Leu Gln Leu Ile Val Val Ile
                565                 570                 575

Leu Pro Gly Lys Thr Pro Val Tyr Ala Glu Val Lys Arg Val Gly Asp
            580                 585                 590

Thr Leu Leu Gly Met Ala Thr Gln Cys Val Gln Val Lys Asn Val Val
        595                 600                 605

Lys Thr Ser Pro Gln Thr Leu Ser Asn Leu Cys Leu Lys Ile Asn Ala
    610                 615                 620

Lys Leu Gly Gly Ile Asn Asn Val Leu Val Pro His Gln Arg Pro Ser
625                 630                 635                 640

Val Phe Gln Gln Pro Val Ile Phe Leu Gly Ala Asp Val Thr His Pro
                645                 650                 655

Pro Ala Gly Asp Gly Lys Lys Pro Ser Ile Ala Ala Val Val Gly Ser
            660                 665                 670

Met Asp Gly His Pro Ser Arg Tyr Cys Ala Thr Val Arg Val Gln Thr
        675                 680                 685

Ser Arg Gln Glu Ile Ser Gln Glu Leu Leu Tyr Ser Gln Glu Val Ile
    690                 695                 700

Gln Asp Leu Thr Asn Met Val Arg Glu Leu Leu Ile Gln Phe Tyr Lys
705                 710                 715                 720

Ser Thr Arg Phe Lys Pro Thr Arg Ile Ile Tyr Tyr Arg Gly Gly Val
                725                 730                 735

Ser Glu Gly Gln Met Lys Gln Val Ala Trp Pro Glu Leu Ile Ala Ile
            740                 745                 750

Arg Lys Ala Cys Ile Ser Leu Glu Glu Asp Tyr Arg Pro Gly Ile Thr
        755                 760                 765

Tyr Ile Val Val Gln Lys Arg His His Thr Arg Leu Phe Cys Ala Asp
    770                 775                 780

Lys Thr Glu Arg Val Gly Lys Ser Gly Asn Val Pro Ala Gly Thr Thr
785                 790                 795                 800

Val Asp Ser Thr Ile Thr His Pro Ser Glu Phe Asp Phe Tyr Leu Cys
                805                 810                 815

Ser His Ala Gly Ile Gln Gly Thr Ser Arg Pro Ser His Tyr Gln Val
            820                 825                 830

Leu Trp Asp Asp Asn Cys Phe Thr Ala Asp Glu Leu Gln Leu Leu Thr
        835                 840                 845

Tyr Gln Leu Cys His Thr Tyr Val Arg Cys Thr Arg Ser Val Ser Ile
    850                 855                 860

Pro Ala Pro Ala Tyr Tyr Ala Arg Leu Val Ala Phe Arg Ala Arg Tyr
865                 870                 875                 880

His Leu Val Asp Lys Asp His Asp Ser Ala Glu Gly Ser His Val Ser
                885                 890                 895

Gly Gln Ser Asn Gly Arg Asp Pro Gln Ala Leu Ala Lys Ala Val Gln
            900                 905                 910

Ile His His Asp Thr Gln His Thr Met Tyr Phe Ala
        915                 920
```

```
<210> SEQ ID NO 71
<211> LENGTH: 855
<212> TYPE: PRT
<213> ORGANISM: Homo sapiens
<220> FEATURE:
<221> NAME/KEY: MISC_FEATURE
<223> OTHER INFORMATION: eIF2C4, predicted protein sequence

<400> SEQUENCE: 71

Ala Gly Pro Ala Gly Ala Gln Pro Leu Leu Met Val Pro Arg Arg Pro
1               5                   10                  15

Gly Tyr Gly Thr Met Gly Lys Pro Ile Lys Leu Leu Ala Asn Cys Phe
            20                  25                  30

Gln Val Glu Ile Pro Lys Ile Asp Val Tyr Leu Tyr Glu Val Asp Ile
        35                  40                  45

Lys Pro Asp Lys Cys Pro Arg Arg Val Asn Arg Glu Val Val Asp Ser
    50                  55                  60

Met Val Gln His Phe Lys Val Thr Ile Phe Gly Asp Arg Arg Pro Val
65                  70                  75                  80

Tyr Asp Gly Lys Arg Ser Leu Tyr Thr Ala Asn Pro Leu Pro Val Ala
                85                  90                  95

Thr Thr Gly Val Asp Leu Asp Val Thr Leu Pro Gly Glu Gly Gly Lys
            100                 105                 110

Asp Arg Pro Phe Lys Val Ser Ile Lys Phe Val Ser Arg Val Ser Trp
        115                 120                 125

His Leu Leu His Glu Val Leu Thr Gly Arg Thr Leu Pro Glu Pro Leu
    130                 135                 140

Glu Leu Asp Lys Pro Ile Ser Thr Asn Pro Val His Ala Val Asp Val
145                 150                 155                 160

Val Leu Arg His Leu Pro Ser Met Lys Tyr Thr Pro Val Gly Arg Ser
                165                 170                 175

Phe Phe Ser Ala Pro Glu Gly Tyr Asp His Pro Leu Gly Gly Gly Arg
            180                 185                 190

Glu Val Trp Phe Gly Phe His Gln Ser Val Arg Pro Ala Met Trp Lys
        195                 200                 205

Met Met Leu Asn Ile Asp Val Ser Ala Thr Ala Phe Tyr Lys Ala Gln
    210                 215                 220

Pro Val Ile Gln Phe Met Cys Glu Val Leu Asp Ile His Asn Ile Asp
225                 230                 235                 240

Glu Gln Pro Arg Pro Leu Thr Asp Ser His Arg Val Lys Phe Thr Lys
                245                 250                 255

Glu Ile Lys Gly Leu Lys Val Glu Val Thr His Cys Gly Thr Met Arg
            260                 265                 270

Arg Lys Tyr Arg Val Cys Asn Val Thr Arg Arg Pro Ala Ser His Gln
        275                 280                 285

Thr Phe Pro Leu Gln Leu Glu Asn Gly Gln Thr Val Glu Arg Thr Val
    290                 295                 300

Ala Gln Tyr Phe Arg Glu Lys Tyr Thr Leu Gln Leu Lys Tyr Pro His
305                 310                 315                 320

Leu Pro Cys Leu Gln Val Gly Gln Glu Gln Lys His Thr Tyr Leu Pro
                325                 330                 335

Leu Glu Val Cys Asn Ile Val Ala Gly Gln Arg Cys Ile Lys Lys Leu
            340                 345                 350

Thr Asp Asn Gln Thr Ser Thr Met Ile Lys Ala Thr Ala Arg Ser Ala
        355                 360                 365
```

-continued

Pro Asp Arg Gln Glu Glu Ile Ser Arg Leu Val Arg Ser Ala Asn Tyr
370                 375                 380

Glu Thr Asp Pro Phe Val Gln Glu Phe Gln Phe Lys Val Arg Asp Glu
385                 390                 395                 400

Met Ala His Val Thr Gly Arg Val Leu Pro Ala Pro Met Leu Gln Tyr
        405                 410                 415

Gly Gly Arg Asn Arg Thr Val Ala Thr Pro Ser His Gly Val Trp Asp
            420                 425                 430

Met Arg Gly Lys Gln Phe His Thr Gly Val Glu Ile Lys Met Trp Ala
        435                 440                 445

Ile Ala Cys Phe Ala Thr Gln Arg Gln Cys Arg Glu Glu Ile Leu Lys
450                 455                 460

Gly Phe Thr Asp Gln Leu Arg Lys Ile Ser Lys Asp Ala Gly Met Pro
465                 470                 475                 480

Ile Gln Gly Gln Pro Cys Phe Cys Lys Tyr Ala Gln Gly Ala Asp Ser
            485                 490                 495

Val Glu Pro Met Phe Arg His Leu Lys Asn Thr Tyr Ser Gly Leu Gln
        500                 505                 510

Leu Ile Ile Val Ile Leu Pro Gly Lys Thr Pro Val Tyr Ala Glu Val
515                 520                 525

Lys Arg Val Gly Asp Thr Leu Leu Gly Met Ala Thr Gln Cys Val Gln
530                 535                 540

Val Lys Asn Val Ile Lys Thr Ser Pro Gln Thr Leu Ser Asn Leu Cys
545                 550                 555                 560

Leu Lys Ile Asn Val Lys Leu Gly Gly Ile Asn Asn Ile Leu Val Pro
            565                 570                 575

His Gln Arg Pro Ser Val Phe Gln Gln Pro Val Ile Phe Leu Gly Ala
        580                 585                 590

Asp Val Thr His Pro Pro Ala Gly Asp Gly Lys Lys Pro Ser Ile Ala
            595                 600                 605

Ala Val Val Gly Ser Met Asp Ala His Pro Ser Arg Tyr Cys Ala Thr
610                 615                 620

Val Arg Val Gln Arg Pro Arg Gln Glu Ile Ile Gln Asp Leu Ala Ser
625                 630                 635                 640

Met Val Arg Glu Leu Leu Ile Gln Phe Tyr Lys Ser Thr Arg Phe Lys
            645                 650                 655

Pro Thr Arg Ile Ile Phe Tyr Arg Asp Gly Val Ser Glu Gly Gln Phe
            660                 665                 670

Arg Gln Val Leu Tyr Tyr Glu Leu Leu Ala Ile Arg Glu Ala Cys Ile
        675                 680                 685

Ser Leu Glu Lys Asp Tyr Gln Pro Gly Ile Thr Tyr Ile Val Val Gln
690                 695                 700

Lys Arg His His Thr Arg Leu Phe Cys Ala Asp Arg Thr Glu Arg Val
705                 710                 715                 720

Gly Arg Ser Gly Asn Ile Pro Ala Gly Thr Thr Val Asp Thr Asp Ile
            725                 730                 735

Thr His Pro Tyr Glu Phe Asp Phe Tyr Leu Cys Ser His Ala Gly Ile
        740                 745                 750

Gln Gly Thr Ser Arg Pro Ser His Tyr His Val Leu Trp Asp Asp Asn
            755                 760                 765

Cys Phe Thr Ala Asp Glu Leu Gln Leu Leu Thr Tyr Gln Leu Cys His
770                 775                 780

Thr Tyr Val Arg Cys Thr Arg Ser Val Ser Ile Pro Ala Pro Ala Tyr

```
                785                 790                 795                 800
Tyr Ala His Leu Val Ala Phe Arg Ala Arg Tyr His Leu Val Asp Lys
                    805                 810                 815

Glu His Asp Ser Ala Glu Gly Ser His Val Ser Gly Gln Ser Asn Gly
                    820                 825                 830

Arg Asp Pro Gln Ala Leu Ala Lys Ala Val Gln Ile His Gln Asp Thr
                    835                 840                 845

Leu Arg Thr Met Tyr Phe Ala
                    850                 855

<210> SEQ ID NO 72
<211> LENGTH: 764
<212> TYPE: PRT
<213> ORGANISM: Homo sapiens
<220> FEATURE:
<221> NAME/KEY: MISC_FEATURE
<223> OTHER INFORMATION: HILI, predicted protein sequence

<400> SEQUENCE: 72

Ile Ser Ser Gly Asp Ala Gly Ser Thr Phe Met Glu Arg Gly Val Lys
1               5                   10                  15

Asn Lys Gln Asp Phe Met Asp Leu Ser Ile Cys Thr Arg Glu Lys Leu
            20                  25                  30

Ala His Val Arg Asn Cys Lys Thr Gly Ser Ser Gly Ile Pro Val Lys
        35                  40                  45

Leu Val Thr Asn Leu Phe Asn Leu Asp Phe Pro Gln Asp Trp Gln Leu
    50                  55                  60

Tyr Gln Tyr His Val Thr Tyr Ile Pro Asp Leu Ala Ser Arg Arg Leu
65                  70                  75                  80

Arg Ile Ala Leu Leu Tyr Ser His Ser Glu Leu Ser Asn Lys Ala Lys
                85                  90                  95

Ala Phe Asp Gly Ala Ile Leu Phe Leu Ser Gln Lys Leu Glu Glu Lys
            100                 105                 110

Val Thr Glu Leu Ser Ser Glu Thr Gln Arg Gly Glu Thr Ile Lys Met
        115                 120                 125

Thr Ile Thr Leu Lys Arg Glu Leu Pro Ser Ser Pro Val Cys Ile
    130                 135                 140

Gln Val Phe Asn Ile Ile Phe Arg Lys Ile Leu Lys Lys Leu Ser Met
145                 150                 155                 160

Tyr Gln Ile Gly Arg Asn Phe Tyr Asn Pro Ser Glu Pro Met Glu Ile
                165                 170                 175

Pro Gln His Lys Leu Ser Leu Trp Pro Gly Phe Ala Ile Ser Val Ser
            180                 185                 190

Tyr Phe Glu Arg Lys Leu Leu Phe Ser Ala Asp Val Ser Tyr Lys Val
        195                 200                 205

Leu Arg Asn Glu Thr Val Leu Glu Phe Met Thr Ala Leu Cys Gln Arg
    210                 215                 220

Thr Gly Leu Ser Cys Phe Thr Gln Thr Cys Glu Lys Gln Leu Ile Gly
225                 230                 235                 240

Leu Ile Val Leu Thr Arg Tyr Asn Asn Arg Thr Tyr Ser Ile Asp Asp
                245                 250                 255

Ile Asp Trp Ser Val Lys Pro Thr His Thr Phe Gln Lys Arg Asp Gly
            260                 265                 270

Thr Glu Ile Thr Tyr Val Asp Tyr Tyr Lys Gln Gln Tyr Asp Ile Thr
        275                 280                 285
```

-continued

Val Ser Asp Leu Asn Gln Pro Met Leu Val Ser Leu Leu Lys Lys Lys
290                 295                 300

Arg Asn Asp Asn Ser Glu Ala Gln Leu Ala His Leu Ile Pro Glu Leu
305                 310                 315                 320

Cys Phe Leu Thr Gly Leu Thr Asp Gln Ala Thr Ser Asp Phe Gln Leu
                325                 330                 335

Met Lys Ala Val Ala Glu Lys Thr Arg Leu Ser Pro Ser Gly Arg Gln
                340                 345                 350

Gln Arg Leu Ala Arg Leu Val Asp Asn Ile Gln Arg Asn Thr Asn Ala
            355                 360                 365

Arg Phe Glu Leu Glu Thr Trp Gly Leu His Phe Gly Ser Gln Ile Ser
370                 375                 380

Leu Thr Gly Arg Ile Val Pro Ser Glu Lys Ile Leu Met Gln Asp His
385                 390                 395                 400

Ile Cys Gln Pro Val Ser Ala Ala Asp Trp Ser Lys Asp Ile Arg Thr
                405                 410                 415

Cys Lys Ile Leu Asn Ala Gln Ser Leu Asn Thr Trp Leu Ile Leu Cys
                420                 425                 430

Ser Asp Arg Thr Glu Tyr Val Ala Glu Ser Phe Leu Asn Cys Leu Arg
            435                 440                 445

Arg Val Ala Gly Ser Met Gly Phe Asn Val Met Cys Ile Leu Pro Ser
450                 455                 460

Asn Gln Lys Thr Tyr Tyr Asp Ser Ile Lys Lys Tyr Leu Ser Ser Asp
465                 470                 475                 480

Cys Pro Val Pro Ser Gln Cys Val Leu Ala Arg Thr Leu Asn Lys Gln
                485                 490                 495

Gly Met Met Met Ser Ile Ala Thr Lys Ile Ala Met Gln Met Thr Cys
                500                 505                 510

Lys Leu Gly Gly Glu Leu Trp Ala Val Glu Ile Pro Leu Lys Ser Leu
            515                 520                 525

Met Val Val Gly Ile Asp Val Cys Lys Asp Ala Leu Ser Lys Asp Val
530                 535                 540

Met Val Val Gly Cys Val Ala Ser Val Asn Pro Arg Ile Thr Arg Trp
545                 550                 555                 560

Phe Ser Arg Cys Ile Leu Gln Arg Thr Met Thr Asp Val Ala Asp Cys
                565                 570                 575

Leu Lys Val Phe Met Thr Gly Ala Leu Asn Lys Trp Tyr Lys Tyr Asn
                580                 585                 590

His Asp Leu Pro Ala Arg Ile Ile Val Tyr Arg Ala Gly Val Gly Asp
            595                 600                 605

Gly Gln Leu Lys Thr Leu Ile Glu Tyr Glu Val Pro Gln Leu Leu Ser
610                 615                 620

Ser Val Ala Glu Ser Ser Asn Thr Ser Ser Arg Leu Ser Val Ile
625                 630                 635                 640

Val Val Arg Lys Lys Cys Met Pro Arg Phe Phe Thr Glu Met Asn Arg
                645                 650                 655

Thr Val Gln Asn Pro Pro Leu Gly Thr Val Val Asp Ser Glu Ala Thr
                660                 665                 670

Arg Asn Glu Trp Gln Tyr Asp Phe Tyr Leu Ile Ser Gln Val Ala Cys
            675                 680                 685

Arg Gly Thr Val Ser Pro Thr Tyr Tyr Asn Val Ile Tyr Asp Asp Asn
690                 695                 700

Gly Leu Lys Pro Asp His Met Gln Arg Leu Thr Phe Lys Leu Cys His

```
                    705                 710                 715                 720
Leu Tyr Tyr Asn Trp Pro Gly Ile Val Ser Val Pro Ala Pro Cys Gln
                725                 730                 735

Tyr Ala His Lys Leu Thr Phe Leu Val Ala Gln Ser Ile His Lys Glu
            740                 745                 750

Pro Ser Leu Glu Leu Ala Asn His Leu Phe Tyr Leu
        755                 760

<210> SEQ ID NO 73
<211> LENGTH: 861
<212> TYPE: PRT
<213> ORGANISM: Homo sapiens
<220> FEATURE:
<221> NAME/KEY: MISC_FEATURE
<223> OTHER INFORMATION: HIWI, predicted protein sequence

<400> SEQUENCE: 73

Met Thr Gly Arg Ala Arg Ala Arg Gly Arg Ala Arg Gly Gln
1               5                   10                  15

Glu Thr Ala Gln Leu Val Gly Ser Thr Ala Ser Gln Pro Gly Tyr
            20                  25                  30

Ile Gln Pro Arg Pro Gln Pro Pro Ala Glu Gly Glu Leu Phe Gly
        35                  40                  45

Arg Gly Arg Gln Arg Gly Thr Ala Gly Gly Thr Ala Lys Ser Gln Gly
50                  55                  60

Leu Gln Ile Ser Ala Gly Phe Gln Glu Leu Ser Leu Ala Glu Arg Gly
65                  70                  75                  80

Gly Arg Arg Arg Asp Phe His Asp Leu Gly Val Asn Thr Arg Gln Asn
                85                  90                  95

Leu Asp His Val Lys Glu Ser Lys Thr Gly Ser Ser Gly Ile Ile Val
            100                 105                 110

Arg Leu Ser Thr Asn His Phe Arg Leu Thr Ser Arg Pro Gln Trp Ala
        115                 120                 125

Leu Tyr Gln Tyr His Ile Asp Tyr Asn Pro Leu Met Glu Ala Arg Arg
130                 135                 140

Leu Arg Ser Ala Leu Leu Phe Gln His Glu Asp Leu Ile Gly Lys Cys
145                 150                 155                 160

His Ala Phe Asp Gly Thr Ile Leu Phe Leu Pro Lys Arg Leu Gln Gln
                165                 170                 175

Lys Val Thr Glu Val Phe Ser Lys Thr Arg Asn Gly Glu Asp Val Arg
            180                 185                 190

Ile Thr Ile Thr Leu Thr Asn Glu Leu Pro Pro Thr Ser Pro Thr Cys
        195                 200                 205

Leu Gln Phe Tyr Asn Ile Ile Phe Arg Arg Leu Leu Lys Ile Met Asn
210                 215                 220

Leu Gln Gln Ile Gly Arg Asn Tyr Tyr Asn Pro Asn Asp Pro Ile Asp
225                 230                 235                 240

Ile Pro Ser His Arg Leu Val Ile Trp Pro Gly Phe Thr Thr Ser Ile
                245                 250                 255

Leu Gln Tyr Glu Asn Ser Ile Met Leu Cys Thr Asp Val Ser His Lys
            260                 265                 270

Val Leu Arg Ser Glu Thr Val Leu Asp Phe Met Phe Asn Phe Tyr His
        275                 280                 285

Gln Thr Glu Glu His Lys Phe Gln Glu Gln Val Ser Lys Glu Leu Ile
290                 295                 300
```

```
Gly Leu Val Val Leu Thr Lys Tyr Asn Asn Lys Thr Tyr Arg Val Asp
305                 310                 315                 320

Asp Ile Asp Trp Asp Gln Asn Pro Lys Ser Thr Phe Lys Lys Ala Asp
            325                 330                 335

Gly Ser Glu Val Ser Phe Leu Glu Tyr Tyr Arg Lys Gln Tyr Asn Gln
        340                 345                 350

Glu Ile Thr Asp Leu Lys Gln Pro Val Leu Val Ser Gln Pro Lys Arg
            355                 360                 365

Arg Arg Gly Pro Gly Gly Thr Leu Pro Gly Pro Ala Met Leu Ile Pro
370                 375                 380

Glu Leu Cys Tyr Leu Thr Gly Leu Thr Asp Lys Met Arg Asn Asp Phe
385                 390                 395                 400

Asn Val Met Lys Asp Leu Ala Val His Thr Arg Leu Thr Pro Glu Gln
                405                 410                 415

Arg Gln Arg Glu Val Gly Arg Leu Ile Asp Tyr Ile His Lys Asn Asp
            420                 425                 430

Asn Val Gln Arg Glu Leu Arg Asp Trp Gly Leu Ser Phe Asp Ser Asn
        435                 440                 445

Leu Leu Ser Phe Ser Gly Arg Ile Leu Gln Thr Glu Lys Ile His Gln
450                 455                 460

Gly Gly Lys Thr Phe Asp Tyr Asn Pro Gln Phe Ala Asp Trp Ser Lys
465                 470                 475                 480

Glu Thr Arg Gly Ala Pro Leu Ile Ser Val Lys Pro Leu Asp Asn Trp
                485                 490                 495

Leu Leu Ile Tyr Thr Arg Arg Asn Tyr Glu Ala Ala Asn Ser Leu Ile
            500                 505                 510

Gln Asn Leu Phe Lys Val Thr Pro Ala Met Gly Met Gln Met Arg Lys
        515                 520                 525

Ala Ile Met Ile Glu Val Asp Asp Arg Thr Glu Ala Tyr Leu Arg Val
530                 535                 540

Leu Gln Gln Lys Val Thr Ala Asp Thr Gln Ile Val Val Cys Leu Leu
545                 550                 555                 560

Ser Ser Asn Arg Lys Asp Lys Tyr Asp Ala Ile Lys Lys Tyr Leu Cys
                565                 570                 575

Thr Asp Cys Pro Thr Pro Ser Gln Cys Val Val Ala Arg Thr Leu Gly
            580                 585                 590

Lys Gln Gln Thr Val Met Ala Ile Ala Thr Lys Ile Ala Leu Gln Met
        595                 600                 605

Asn Cys Lys Met Gly Gly Glu Leu Trp Arg Val Asp Ile Pro Leu Lys
610                 615                 620

Leu Val Met Ile Val Gly Ile Asp Cys Tyr His Asp Met Thr Ala Gly
625                 630                 635                 640

Arg Arg Ser Ile Ala Gly Phe Val Ala Ser Ile Asn Glu Gly Met Thr
                645                 650                 655

Arg Trp Phe Ser Arg Cys Ile Phe Gln Asp Arg Gly Gln Glu Leu Val
            660                 665                 670

Asp Gly Leu Lys Val Cys Leu Gln Ala Ala Leu Arg Ala Trp Asn Ser
        675                 680                 685

Cys Asn Glu Tyr Met Pro Ser Arg Ile Ile Val Tyr Arg Asp Gly Val
690                 695                 700

Gly Asp Gly Gln Leu Lys Thr Leu Val Asn Tyr Glu Val Pro Gln Phe
705                 710                 715                 720

Leu Asp Cys Leu Lys Ser Ile Gly Arg Gly Tyr Asn Pro Arg Leu Thr
```

```
              725                 730                 735
Val Ile Val Val Lys Lys Arg Val Asn Thr Arg Phe Phe Ala Gln Ser
                740                 745                 750

Gly Gly Arg Leu Gln Asn Pro Leu Pro Gly Thr Val Ile Asp Val Glu
                755                 760                 765

Val Thr Arg Pro Glu Trp Tyr Asp Phe Phe Ile Val Ser Gln Ala Val
        770                 775                 780

Arg Ser Gly Ser Val Ser Pro Thr His Tyr Asn Val Ile Tyr Asp Asn
785                 790                 795                 800

Ser Gly Leu Lys Pro Asp His Ile Gln Arg Leu Thr Tyr Lys Leu Cys
                805                 810                 815

His Ile Tyr Tyr Asn Trp Pro Gly Val Ile Arg Val Pro Ala Pro Cys
                820                 825                 830

Gln Tyr Ala His Lys Leu Ala Phe Leu Val Gly Gln Ser Ile His Arg
                835                 840                 845

Glu Pro Asn Leu Ser Leu Ser Asn Arg Leu Tyr Tyr Leu
        850                 855                 860
```

<210> SEQ ID NO 74
<211> LENGTH: 2571
<212> TYPE: DNA
<213> ORGANISM: Homo sapiens
<220> FEATURE:
<221> NAME/KEY: misc_feature
<223> OTHER INFORMATION: eIF2C1, cDNA sequence of predicted ORF

<400> SEQUENCE: 74

```
atggaagcgg gaccctcggg agcagctgcg ggcgcttacc tgccccccct gcagcaggtg     60
ttccaggcac ctcgccggcc tggcattggc actgtgggga aaccaatcaa gctcctggcc    120
aattactttg aggtggacat ccctaagatc gacgtgtacc actacgaggt ggacatcaag    180
ccggataagt gtccccgtag agtcaaccgg gaagtggtgg aatacatggt ccagcatttc    240
aagcctcaga tctttggtga tcgcaagcct gtgtatgatg aaagaagaa catttacact    300 gtcacagcac tgcccattgg caacgaacgg gtcgactttg aggtgacaat ccctgggaa    360 gggaaggatc gaatctttaa ggtctccatc aagtggctag ccattgtgag ctggcgaatg    420
ctgcatgagg ccctggtcag cggccagatc cctgttccct ggagtctgt gcaagccctg    480 gatgtggcca tgaggcacct ggcatccatg aggtacaccc ctgtgggccg ctccttcttc    540
tcaccgcctg agggctacta ccacccgctg ggggtgggc gcgaggtctg gttcggcttt    600
caccagtctg tgcgccctgc catgtggaag atgatgctca acattgatgt ctcagccact    660 gcctttttata aggcacagcc agtgattgag ttcatgtgtg aggtgctgga catcaggaac    720
atagatgagc agcccaagcc cctcacggac tctcagcgcg ttcgcttcac caaggagatc    780
aagggcctga aggtggaagt cacccactgt ggacagatga gaggaagta ccgcgtgtgt    840 aatgttaccc gtcgccctgc tagccatcag acattcccct acagctggaa gagtggacag    900
actgtggagt gcacagtggc acagtatttc aagcagaaat ataaccttca gctcaagtat    960
ccccatctgc cctgcctaca gttggccag gaacaaaagc ataccctacct tccccctagag   1020 gtctgtaaca ttgtgctgg gcagcgctgt attaaaaagc tgaccgacaa ccagacctcg   1080
accatgataa aggccacagc tagatccgct ccagacagac aggaggagat cagtcgcctg   1140
atgaagaatg ccagctacaa cttagatccc tacatccagg aatttgggat caaagtgaag   1200
gatgacatga cggaggtgac agggcgagtg ctgccggcgc ccatcttgca gtacggcggc   1260
```

```
cggaaccggg ccattgccac acccaatcag ggtgtctggg acatgcgggg gaaacagttc   1320
tacaatggga ttgagatcaa agtctgggcc atcgcctgct tcgcaccca aaaacagtgt   1380 cgagaagagg tgctcaagaa cttcacagac cagctgcgga agatttccaa ggatgcgggg   1440
atgcctatcc agggtcaacc ttgtttctgc aaatatgcac aggggcaga cagcgtggag   1500 cctatgttcc ggcatctcaa gaacacctac tcagggctgc agctcattat tgtcatcctg   1560
ccagggaaga cgccggtgta tgctgaggtg aaacgtgtcg agatacact cttgggaatg   1620 gctacgcagt gtgtgcaggt gaagaacgtg gtcaagacct cacctcagac tctgtccaac   1680
ctctgcctca agatcaatgt caaacttggt ggcattaaca acatcctagt cccacaccag   1740
cgctctgccg tttttcaaca gccagtgata ttcctgggag cagatgttac acacccccca   1800 gcagggatg ggaaaaaacc ttctatcaca gcagtggtag gcagtatgga tgcccacccc   1860
agccgatact gtgctactgt gcgggtacag cgaccacggc aagagatcat tgaagacttg   1920
tcctacatgg tgcgtgagct cctcatccaa ttctacaagt ccacccgttt caagcctacc   1980
cgcatcatct tctaccgaga tggggtgcct gaaggccagc taccccagat actccactat   2040
gagctactgg ccattcgtga tgcctgcatc aaactggaaa aggactacca gcctgggatc   2100
acttatattg tggtgcagaa acgccatcac acccgccttt tctgtgctga caagaatgag   2160
cgaattggga agagtggtaa catcccagct gggaccacag tggacaccaa catcacccac   2220
ccatttgagt ttgacttcta tctgtgcagc cacgcaggca tccagggcac cagccgacca   2280
tcccattact atgttctttg ggatgacaac cgtttcacag cagatgagct ccagatcctg   2340
acgtaccagc tgtgccacac ttacgtacga tgcacacgct ctgtctctat cccagcacct   2400
gcctactatg cccgcctggt ggctttccgg gcacgatacc acctggtgga caaggagcat   2460
gacagtggag aggggagcca catatcgggg cagagcaatg gcgggaccc ccaggccctg   2520 gccaaagccg tgcaggttca ccaggatact ctgcgcacca tgtacttcgc t              2571
```

<210> SEQ ID NO 75
<211> LENGTH: 2580
<212> TYPE: DNA
<213> ORGANISM: Homo sapiens
<220> FEATURE:
<221> NAME/KEY: misc_feature
<223> OTHER INFORMATION: eIF2C2, cDNA sequence of predicted ORF
<400> SEQUENCE: 75

```
atgggtgttc tctctgccat tcccgcactt gcacctcctg cgccgccgcc ccccatccaa     60
ggatatgcct tcaagcctcc acctagaccc gactttggga cctccgggag aacaatcaaa    120
ttacaggcca atttcttcga aatggacatc cccaaaattg acatctatca ttatgaattg    180
gatatcaagc cagagaagtg cccgaggaga gttaacaggg aaatcgtgga acacatggtc    240
cagcacttta aaacacagat ctttgggat cggaagcccg tgtttgacgg caggaagaat    300
ctatacacag ccatgcccct tccgattggg agggacaagg tggagctgga ggtcacgctg    360
ccaggagaag gcaaggatcg catcttcaag gtgtccatca gtgggtgtc ctgcgtgagc    420 ttgcaggcgt tacacgatgc actttcaggg cggctgccca gcgtccctt tgagacgatc    480 caggccctgg acgtggtcat gaggcacttg ccatccatga ggtacacccc cgtgggccgc    540
tccttcttca ccgcgtccga aggctgctct aaccctcttg gcgggggccg agaagtgtgg    600
tttggcttcc atcagtccgt ccggccttct ctctggaaaa tgatgctgaa aattgatgtg    660
tcagcaacag cgttttacaa ggcacagcca gtaatcgagt ttgtttgtga agttttggat    720
```

```
tttaaaagta ttgaagaaca acaaaaacct ctgacagatt cccaaagggt aaagtttacc      780
aaagaaatta aaggtctaaa ggtggagata acgcactgtg ggcagatgaa gaggaagtac      840
cgtgtctgca atgtgacccg gcggcccgcc agtcaccaaa cattcccgct gcagcaggag      900
agcgggcaga cggtggagtg cacggtggcc cagtatttca aggacaggca caagttggtt      960
ctgcgctacc cccacctccc atgtttacaa gtcggacagg agcagaaaca cacctacctt     1020
cccctggagg tctgtaacat tgtggcagga caaagatgta ttaaaaaatt aacgacaatt     1080
cagacctcaa ccatgatcag agcaactgct aggtcggcgc ccgatcggca agaagagatt     1140
agcaaattga tgcgaagtgc aagtttcaac acagatccat acgtccgtga atttggaatc     1200
atggtcaaag atgagatgac agacgtgact gggcgggtgc tgcagccgcc ctccatcctc     1260
tacgggggca ggaataaagc tattgcgacc cctgtccagg gcgtctggga catgcggaac     1320
aagcagttcc acacgggcat cgagatcaag gtgtgggcca ttgcgtgctt cgcccccag      1380 cgccagtgca cggaagtcca tctgaagtcc ttcacagagc agctcagaaa gatctcgaga     1440
gacgctggca tgcccatcca gggccagccg tgcttctgca atacgcgca gggggcggac      1500 agcgtggagc ccatgttccg gcacctgaag aacacgtatg cgggcctgca gctggtggtg     1560
gtcatcctgc ccggcaagac gccgtgtac gccgaggtca gcgcgtggg agacacggtg      1620 ctggggatgg ccacgcagtg cgtgcagatg aagaacgtgc agaggaccac gccacagacc     1680
ctgtccaacc tttgcctgaa gatcaacgtc aagctgggag gcgtgaacaa catcctgctg     1740
ccccagggca ggccgccggt gttccagcag cccgtcatct ttctgggagc agacgtcact     1800
cacccccccg ccggggatgg gaagaagccc tccattgccg ccgtggtggg cagcatggac     1860
gcccacccca atcgctactg cgccaccgtg cgcgtgcagc agcaccggca ggagatcata     1920
caagacctgg ccgccatggt ccgcgagctc ctcatccagt tctacaagtc cacgcgcttc     1980
aagcccaccc gcatcatctt ctaccgcgac ggtgtctctg aaggccagtt ccagcaggtt     2040
ctccaccacg agttgctggc catccgtgag gcctgtatca agctagaaaa agactaccag     2100
cccgggatca ccttcatcgt ggtgcagaag aggcaccaca cccggctctt ctgcactgac     2160
aagaacgagc gggttgggaa aagtggaaac attccagcag gcacgactgt ggacacgaaa     2220
atcacccacc ccaccgagtt cgacttctac ctgtgtagtc acgctggcat ccaggggaca     2280
agcaggcctt cgcactatca cgtcctctgg gacgacaatc gtttctcctc tgatgagctg     2340
cagatcctaa cctaccagct gtgtcacacc tacgtgcgct gcacacgctc cgtgtccatc     2400
ccagcgccag catactacgc tcacctggtg gccttccggg ccaggtacca cctggtggat     2460
aaggaacatg acagtgctga aggaagccat acctctgggc agagtaacgg gcgagaccac     2520
caagcactgg ccaaggcggt ccaggttcac caagacactc tgcgcaccat gtactttgct     2580
```

<210> SEQ ID NO 76
<211> LENGTH: 2772
<212> TYPE: DNA
<213> ORGANISM: Homo sapiens
<220> FEATURE:
<221> NAME/KEY: misc_feature
<223> OTHER INFORMATION: eIF2C3, cDNA sequence of predicted ORF

<400> SEQUENCE: 76

```
agccggagcc gggtccctgt ccccgggccg ggcgccgccg ccgcccctg cccagcgccc        60 gcgtctccgc ggcgccaccc cagcgccaat attccggaga tcaagcgtta cgcggcggcg      120
gcggcggcgg cggcggggcc cggagcggga ggcgccgggg accggggcga ggcggccccc      180
```

```
gccgccgcca tggaggcgct gggacccgga cctccggcta gcctgtttca gccacctcgt    240
cgtcctggcc ttggaactgt tggaaaacca attcgactgt tagccaatca ttttcaggtt    300
cagattccta aaatagatgt gtatcactat gatgtggata ttaagcctga aaacggcct     360 cgtagagtca acaggggagt agtagataca atggtgcggc acttcaagat gcaaatattt    420
ggtgatcggc agcctgggta tgatggcaaa agaaacatgt acacagcaca tccactacca    480
attggacggg ataggggttga tatggaggtg actcttccag gcgagggtaa agaccaaaca    540
tttaaagtgt ctgttcagtg ggtgtcagtt gtgagccttc agttgctttt agaagctttg    600
gctgggcact tgaatgaagt cccagatgac tcagtacaag cacttgatgt tatcacaaga    660
caccttccct ccatgaggta caccccagtg ggccgttcct ttttctcacc cccggaaggt    720
tactaccacc ctctggggag gggcaggggag gtctggtttg gttttcatca gtctgtgaga    780
cctgccatgt ggaatatgat gctcaacatt gatgtatctg caactgcttt ctaccgggct    840
cagcctatca ttgagttcat gtgtgaggtt ttagacattc agaacatcaa tgaacagacc    900
aaacctctaa cagactccca gcgtgtcaaa tttaccaaag aaatcagagg tctcaaagtt    960
gaggtgaccc actgtggaca gatgaaacga aaataccgag tttgtaatgt gactagacgg   1020
ccagccagtc atcaaacttt tcctttgcag ctagaaaacg gtcaagctat ggaatgtaca   1080
gtagctcaat attttaagca aaagtatagt ctgcaactga ataccccca tcttccctgt    1140 ctccaagtgg acaagaaca aaagcataca tacttgccac tcgaggtctg taatatagtg    1200
gcaggacagc gatgtatcaa gaagctcaca gacaatcaga cttccacaat gatcaaagct   1260
acagcaagat ctgctcctga cagacaggaa gagatcagta gactggtgaa gagcaacagt   1320
atggtgggtg gacctgatcc ataccttaaa gaatttggta ttgttgtcca caatgaaatg   1380
acagagctca caggcagggt acttccagca ccaatgctgc aatatggagg ccggaataaa   1440
acagtagcca cacccaacca gggtgtctgg gacatgcgag gaaagcagtt ttatgctggc   1500
attgaaatta agtttgggc agttgcttgt tttgcacctc agaaacaatg tagggaagat   1560
ttactaaaga gtttcactga ccagctgcgt aaaatctcta aggatgcagg aatgcccatc   1620
cagggtcagc catgtttctg caagtatgca caaggtgcag acagtgtgga gcctatgttt   1680
aaacatctga aaatgactta tgtgggccta cagctaatag tggttatcct gcctggaaag   1740
acaccagtat atgcggaggt gaaacgtgtt ggagataccc ttctaggtat ggccacacag   1800
tgtgtccagg taaaaaatgt agtgaagacc tcacctcaaa cccttccaa tctttgcctg    1860 aagataaatg caaacttgg aggaattaac aatgtgcttg tgcctcatca aaggccctcg   1920
gtgttccagc agcctgtcat cttcctggga gcggatgtca cacacccccc agcagggggat   1980 gggaagaaac cttccattgc tgctgtggtt ggcagtatgg atggccaccc cagccggtac   2040
tgtgccaccg ttcgggtgca gacttcccgg caggagatct cccaagagct cctctacagt   2100
caagaggtca tccaggacct gactaacatg gttcgagagc tgctgattca gttctacaaa   2160
tccacacgct tcaaacccac tcggatcatc tattaccgtg gaggggtatc tgagggacaa   2220
atgaaacagg tagcttggcc agaactaata gcaattcgaa aggcatgtat tagcttggaa   2280
gaagattacc ggccaggaat aacttatatt gtggtgcaaa aaagacatca cacgcgactc   2340
ttctgtgcag ataaaacaga aagggtaggg aaaagtggca atgtaccagc aggcactaca   2400
gtggatagta ccatcacaca tccatctgag tttgactttt acctctgtag tcatgcagga   2460
attcagggaa ccagccgtcc ctcacattac caggtcttgt gggatgacaa ctgcttcact   2520
gcagatgaac tccagctact gacttaccag ctgtgtcaca cctatgtgag gtgcactcgc   2580
```

```
tcagtctcta ttccagcccc tgcatattat gcccggcttg tagcatttag ggcaaggtat    2640
catctggtgg ataaagatca tgacagtgcg gaaggcagtc atgtgtcagg acagagcaac    2700
ggccgggatc ctcaggcctt ggctaaggct gtgcaaatcc accatgatac ccagcacacg    2760
atgtattttg cc                                                       2772

<210> SEQ ID NO 77
<211> LENGTH: 2568
<212> TYPE: DNA
<213> ORGANISM: Homo sapiens
<220> FEATURE:
<221> NAME/KEY: misc_feature
<223> OTHER INFORMATION: eIF2C4, cDNA sequence of predicted ORF

<400> SEQUENCE: 77
gcaggacccg ctggggccca gcccctactc atggtgccca gaagacctgg ctatggcacc      60
atgggcaaac ccattaaact gctggctaac tgttttcaag ttgaaatccc aaagattgat     120
gtctacctct atgaggtaga tattaaacca gacaagtgtc ctaggagagt gaacaggagc     180
gtggttgact caatggttca gcattttaaa gtaactatat ttggagaccg tagaccagtt     240
tatgatggaa aaagaagtct ttacaccgcc aatccacttc ctgtggcaac tacagggta      300 gatttagacg ttactttacc tggggaaggt ggaaagatc gaccttcaa ggtgtcaatc      360 aaatttgtct ctcgggtgag ttggcaccta ctgcatgaag tactgacagg acggaccttg     420
cctgagccac tggaattaga caagccaatc agcactaacc ctgtccatgc cgttgatgtg     480
gtgctacgac atctgccctc catgaaatac acacctgtgg ggcgttcatt tttctccgct     540
ccagaaggat atgaccaccc tctgggaggg ggcagggaag tgtggtttgg attccatcag     600
tctgttcggc ctgccatgtg gaaaatgatg cttaatatcg atgtttctgc cactgccttc     660
tacaaagcac aacctgtaat tcagttcatg tgtgaagttc ttgatattca taatattgat     720
gagcaaccaa gacctctgac tgattctcat cgggtaaaat tcaccaaaga gataaaaggt     780
ttgaaggttg aagtgactca ttgtggaaca atgagacgga ataccgtgt ttgtaatgta     840 acaaggaggc ctgccagtca tcaaaccttt cctttacagt tagaaaacgg ccaaactgtg     900
gagagaacag tagcgcagta tttcagagaa aagtatactc ttcagctgaa gtacccgcac     960
cttccctgtc tgcaagtcgg gcaggaacag aaacacacct acctgccact agaagtctgt    1020
aatattgtgg cagggcaacg atgtatcaag aagctaacag acaatcagac ttccactatg    1080
atcaaggcaa cagcaagatc tgcaccagat agacaagagg aaattagcag attggtaaga    1140
agtgcaaatt atgaaacaga tccatttgtt caggagtttc aatttaaagt tcgggatgaa    1200
atggctcatg taactggacg cgtacttcca gcacctatgc tccagtatgg aggacgaat    1260 cggacagtag caacaccgag ccatggagta tgggacatgc gagggaaaca attccacaca    1320
ggagttgaaa tcaaaatgtg ggctatcgct tgttttgcca cacagaggca gtgcagagaa    1380
gaaatattga agggtttcac agaccagctg cgtaagattt ctaaggatgc agggatgccc    1440
atccagggcc agccatgctt ctgcaaatat gcacaggggg cagacagcgt agagcccatg    1500
ttccggcatc tcaagaacac atattctggc ctacagctta ttatcgtcat cctgccgggg    1560
aagacaccag tgtatgcgga agtgaaacgt gtaggagaca cttttggg tatggctaca    1620 caatgtgttc aagtcaagaa tgtaataaaa acatctcctc aaactctgtc aaacttgtgc    1680
ctaaagataa atgttaaact cggagggatc aataatatc ttgtacctca tcaaagacct    1740
tctgtgttcc agcaaccagt gatctttttg ggagccgatg tcactcatcc acctgctggt    1800
```

```
gatggaaaga agccttctat tgctgctgtt gtaggtagta tggatgcaca cccaagcaga    1860
tactgtgcca cagtaagagt tcagagaccc cgacaggaga tcatccagga cttggcctcc    1920
atggtccggg aacttcttat tcaattttat aagtcaactc ggttcaagcc tactcgtatc    1980
atcttttatc gggatggtgt ttcagagggg cagtttaggc aggtattata ttatgaacta    2040
ctagcaattc gagaagcctg catcagtttg gagaaagact atcaacctgg ataacctac     2100 attgtagttc agaagagaca tcacactcga ttattttgtg ctgataggac agaaagggtt    2160
ggaagaagtg gcaatatccc agctggaaca acagttgata cagacattac acacccatat    2220
gagttcgatt tttacctctg tagccatgct ggaatacagg gtaccagtcg tccttcacac    2280
tatcatgttt tatgggatga taactgcttt actgcagatg aacttcagct gctaacttac    2340
cagctctgcc acacttacgt acgctgtaca cgatctgttt ctatacctgc accagcgtat    2400
tatgctcacc tggtagcatt tagagccaga tatcatcttg tggacaaaga acatgacagt    2460
gctgaaggaa gtcacgtttc aggacaaagc aatgggcgag atccacaagc tcttgccaag    2520
gctgtacaga ttcaccaaga taccttacgc acaatgtact tcgcttaa               2568

<210> SEQ ID NO 78
<211> LENGTH: 2292
<212> TYPE: DNA
<213> ORGANISM: Homo sapiens
<220> FEATURE:
<221> NAME/KEY: misc_feature
<223> OTHER INFORMATION: HILI, cDNA sequence of predicted ORF

<400> SEQUENCE: 78
atatcttctg gtgatgctgg aagtaccttc atggaaagag gtgtgaaaaa caaacaggac      60
tttatggatt tgagtatctg taccagagaa aaattggcac atgtgagaaa ttgtaaaaca     120
ggttccagtg gaatacctgt gaaactggtt acaaacctct ttaacttaga ttttcccccaa    180 gactggcagc tataccagta ccatgtgaca tatattccag atttagcatc tagaaggctg     240
agaattgctt tactttatag tcatagtgaa cttccaacaa aagcaaaagc attcgacggt     300
gccatccttt ttctgtcaca aaagctagaa gaaaaggtca cagagttgtc aagtgaaact     360
caaagaggtg agactataaa gatgactatc accctgaaga gggagctgcc atcaagttct     420
cccgtgtgca tccaggtctt caatatcatc ttcagaaaga tcctcaaaaa gttgtccatg     480
taccaaattg gacggaactt ctataatcct tcagagccaa tggaaattcc ccagcacaaa     540
ttatcccttt ggcctgggtt tgccatttct gtgtcatatt ttgaaaggaa gctcctgttt     600
agtgctgatg tgagttacaa agtcctccgg aatgagacgg ttctggaatt catgactgct     660
ctctgtcaaa gaactggctt gtcctgtttc acccagacgt gtgagaagca gctaataggg     720
ctcattgtcc ttacaagata caataacaga acctactcca ttgatgacat tgactggtca     780
gtgaagccca cacaccctt tcagaagcgg atggcaccg agatcaccta tgtggattac      840
tacaagcagc agtatgatat tactgtatcg gacctgaatc agcccatgct tgttagtctg     900
ttaaagaaga agagaaatga caacagtgag gctcagctcg cccacctgat acctgagctc     960
tgctttctaa cagggctgac tgaccaggca acatctgatt tccagctgat gaaggctgtg    1020
gctgaaaaga cacgtctcag tccttcaggc cggcagcagc gcctggccag gcttgtggac    1080
aacatccaga ggaataccaa tgctcgcttt gaactagaga cctggggact gcattttgga    1140
agccagatat ctctgactgg ccggattgtg ccttcagaaa aaatattaat gcaagaccac    1200
atatgtcaac ctgtgtctgc tgctgactgg tccaaggata ttcgaacttg caagatttta    1260
```

```
aatgcacagt ctttgaatac ctggttgatt ttatgtagcg acagaactga atatgttgcc    1320
gagagctttc tgaactgctt gagaagagtt gcaggttcca tgggatttaa tgtaatgtgc    1380
attctgcctt ctaatcagaa gacctattat gattccatta aaaatatttt gagctcagac    1440
tgcccagtcc caagccaatg tgtgcttgct cggaccttga ataaacaggg catgatgatg    1500
agtatcgcca ccaagatcgc tatgcagatg acttgcaagc tcggaggcga gctgtgggct    1560
gtggaaatac ctttaaagtc cctgatggtg gtcggtattg atgtctgtaa agatgcactc    1620
agcaaggacg tgatggttgt tggatgcgtg ccagtgtta accccagaat caccaggtgg    1680
ttttcccgct gtatccttca gagaacaatg actgatgttg cagattgctt gaaagttttc    1740
atgactggag cactcaacaa atggtacaag tacaatcatg atttgccagc acggataatt    1800
gtgtaccgtg ctggtgtagg ggatggtcag ctgaaaacac ttattgaata tgaagtccca    1860
cagctgctga gcagtgtggc agaatccagc tcaaatacca gctcaagact gtcggtgatt    1920
gtggtcagga agaagtgcat gccacgattc tttaccgaaa tgaaccgcac tgtacagaac    1980 ccccccacttg gcactgttgt ggattcagaa gcaacacgta acgaatggca gtatgacttt    2040
tatctgatca gccaggtggc ctgccgggga actgttagtc ctacctacta taatgtcatc    2100
tatgatgaca acggcttgaa gcccgaccat atgcagagac ttacattcaa attgtgccac    2160
ctgtactaca actggccggg catagtcagt gtcccagcac catgtcagta tgctcacaag    2220
ctgacctttc tggtggcaca aagcattcat aaagaaccca gtctggaatt agccaaccat    2280
ctcttctacc tg    2292

<210> SEQ ID NO 79
<211> LENGTH: 2583
<212> TYPE: DNA
<213> ORGANISM: Homo sapiens
<220> FEATURE:
<221> NAME/KEY: misc_feature
<223> OTHER INFORMATION: HIWI, cDNA sequence of predicted ORF

<400> SEQUENCE: 79
atgactggga gagcccgagc cagagccaga ggaagggccc gcggtcagga gacagcgcag      60
ctggtgggct ccactgccag tcagcaacct ggttatattc agcctaggcc tcagccgcca     120
ccagcagagg gggaattatt tggccgtgga cggcagagag gaacagcagg aggaacagcc     180
aagtcacaag gactccagat atctgctgga tttcaggagt tatcgttagc agagagagga     240
ggtcgtcgta gagattttca tgatcttggt gtgaatacaa ggcagaacct agaccatgtt     300
aaagaatcaa aaacaggttc ttcaggcatt atagtaaggt taagcactaa ccatttccgg     360
ctgacatccc gtccccagtg ggcctttata cagtatcaca ttgactataa cccactgatg     420
gaagccagaa gactccgttc agctcttctt tttcaacacg aagatctaat tggaaagtgc     480
catgcttttg atgaacgat attattttta cctaaaagac tacagcaaaa ggttactgaa     540 gttttagta agacccggaa tggagaggat gtgaggataa cgatcacttt aacaaatgaa     600
cttccaccta catcaccaac ttgtttgcag ttctataata ttattttcag gaggcttttg     660
aaaatcatga atttgcaaca aattggacga attattata acccaaatga cccaattgat     720
attccaagtc acaggttggt gatttggcct ggcttcacta cttccatcct tcagtatgaa     780
aacagcatca tgctctgcac tgacgttagc cataaagtcc ttcgaagtga gactgttttg     840
gatttcatgt tcaactttta tcatcagaca gaagaacata aatttcaaga acaagtttcc     900
aaagaactaa taggtttagt tgttcttacc aagtataaca ataagacata cagagtggat     960
```

```
gatattgact gggaccagaa tcccaagagc acctttaaga aagccgacgg ctctgaagtc    1020
agcttcttag aatactacag gaagcaatac aaccaagaga tcaccgactt gaagcagcct    1080
gtcttggtca gccagcccaa gagaaggcgg ggccctgggg ggacactgcc agggcctgcc    1140
atgctcattc ctgagctctg ctatcttaca ggtctaactg ataaaatgcg taatgatttt    1200
aacgtgatga agacttagc cgttcataca agactaactc cagagcaaag gcagcgtgaa    1260
gtgggacgac tcattgatta cattcataaa acgataatg ttcaaaggga gcttcgagac    1320
tggggtttga gctttgattc caacttactg tccttctcag gaagaatttt gcaaacagaa    1380
aagattcacc aaggtggaaa acatttgat tacaatccac aatttgcaga ttggtccaaa    1440
gaaacaagag gtgcaccatt aattagtgtt aagccactag ataactggct gttgatctat    1500
acgcgaagaa attatgaagc agccaattca ttgatacaaa atctatttaa agttacacca    1560
gccatgggca tgcaaatgag aaaagcaata atgattgaag tggatgacag aactgaagcc    1620
tacttaagag tcttacagca aaaggtcaca gcagacaccc agatagttgt ctgtctgttg    1680
tcaagtaatc ggaaggacaa atacgatgct attaaaaaat acctgtgtac agattgccct    1740
accccaagtc agtgtgtggt ggcccgaacc ttaggcaaac agcaaactgt catggccatt    1800
gctacaaaga ttgccctaca gatgaactgc aagatgggag gagagctctg gagggtggac    1860 atcccccctga agctcgtgat gatcgttggc atcgattgtt accatgacat gacagctggg    1920
cggaggtcaa tcgcaggatt tgttgccagc atcaatgaag ggatgacccg ctggttctca    1980
cgctgcatat ttcaggatag aggacaggag ctggtagatg ggctcaaagt ctgcctgcaa    2040
gcggctctga gggcttggaa tagctgcaat gagtacatgc ccagccggat catcgtgtac    2100
cgcgatggcg taggagacgg ccagctgaaa acactggtga actacgaagt gccacagttt    2160
ttggattgtc taaaatccat tggtagaggt tacaacccta gactaacggt aattgtggtg    2220
aagaaaagag tgaacaccag attttttgct cagtctggag gaagacttca gaatccactt    2280
cctggaacag ttattgatgt agaggttacc agaccagaat ggtatgactt ttttatcgtg    2340
agccaggctg tgagaagtgg tagtgtttct cccacacatt acaatgtcat ctatgacaac    2400
agcggcctga gccagacca catacagcgc ttgacctaca agctgtgcca catctattac    2460
aactggccag gtgtcattcg tgttcctgct ccttgccagt acgcccacaa gctggctttt    2520
cttgttggcc agagtattca cagagagcca aatctgtcac tgtcaaaccg cctttactac    2580
ctc                                                                  2583
```

<210> SEQ ID NO 80
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 80

```
gaggtctgta acattgtggc                                                  20
```

<210> SEQ ID NO 81
<211> LENGTH: 20
<212> TYPE: DNA
<213> ORGANISM: Artificial Sequence
<220> FEATURE:

```
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 81
cggtagaaga tgatgcgggt                                                     20

<210> SEQ ID NO 82
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 82
gaggtctgta acattgtggc                                                     20

<210> SEQ ID NO 83
<211> LENGTH: 24
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 83
aagttcttga gcacctcttc tcga                                                24

<210> SEQ ID NO 84
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 84
gaggtctgta acattgtggc                                                     20

<210> SEQ ID NO 85
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 85
cggtagaaga tgatgcgggt                                                     20

<210> SEQ ID NO 86
<211> LENGTH: 18
<212> TYPE: DNA
<213> ORGANISM: Artificial Sequence
```

```
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 86
ccacaccagc gctctgcc                                                        18

<210> SEQ ID NO 87
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C1, primer (5'-3')

<400> SEQUENCE: 87
ctcacgcacc atgtagga                                                        18

<210> SEQ ID NO 88
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 88
gaggtctgta acattgtggc                                                      20

<210> SEQ ID NO 89
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 89
cggtagaaga tgatgcgggt                                                      20

<210> SEQ ID NO 90
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 90
atcctgctgc cccaaggg                                                        18

<210> SEQ ID NO 91
<211> LENGTH: 18
<212> TYPE: DNA
```

```
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 91
gatctcctgc cggtgctg                                                  18

<210> SEQ ID NO 92
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 92
gaggtctgta acattgtggc                                                20

<210> SEQ ID NO 93
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 93
cggtagaaga tgatgcgggt                                                20

<210> SEQ ID NO 94
<211> LENGTH: 20
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 94
gaggtctgta acattgtggc                                                20

<210> SEQ ID NO 95
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C2, primer (5'-3')

<400> SEQUENCE: 95
gatctcctgc cggtgctg                                                  18

<210> SEQ ID NO 96
<211> LENGTH: 24
```

```
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 96
agagcaacag tatggtgggt ggac                                          24

<210> SEQ ID NO 97
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 97
tggatgtgtg atggtact                                                 18

<210> SEQ ID NO 98
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 98
cctctacagt caagaggt                                                 18

<210> SEQ ID NO 99
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 99
tggatgtgtg atggtact                                                 18

<210> SEQ ID NO 100
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 100
cacttgaatg aagtccca                                                 18

<210> SEQ ID NO 101
```

```
<211> LENGTH: 24
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 101
tcctggatga cctcttgact gtag                                              24

<210> SEQ ID NO 102
<211> LENGTH: 24
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 102
agagcaacag tatggtgggt ggac                                              24

<210> SEQ ID NO 103
<211> LENGTH: 24
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C3, primer (5'-3')

<400> SEQUENCE: 103
tcctggatga cctcttgact gtag                                              24

<210> SEQ ID NO 104
<211> LENGTH: 26
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C4, primer (5'-3')

<400> SEQUENCE: 104
tccggcatct caagaacaca tattct                                            26

<210> SEQ ID NO 105
<211> LENGTH: 26
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C4, primer (5'-3')

<400> SEQUENCE: 105
gaactcatat gggtgtgtaa tgtctg                                            26
```

```
<210> SEQ ID NO 106
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C4, primer (5'-3')

<400> SEQUENCE: 106
atccaggact tggcctcc                                                 18

<210> SEQ ID NO 107
<211> LENGTH: 26
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: eIF2C4, primer (5'-3')

<400> SEQUENCE: 107
gaactcatat gggtgtgtaa tgtctg                                        26

<210> SEQ ID NO 108
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: HILI, primer (5'-3')

<400> SEQUENCE: 108
cagcacaaat tatcccTT                                                 18

<210> SEQ ID NO 109
<211> LENGTH: 23
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: HILI, primer (5'-3')

<400> SEQUENCE: 109
cggcctgaag gactgagacg tgt                                           23

<210> SEQ ID NO 110
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: HILI, primer (5'-3')

<400> SEQUENCE: 110
cagcacaaat tatcccTT                                                 18
```

<210> SEQ ID NO 111
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: HILI, primer (5'-3')

<400> SEQUENCE: 111
gtgtgtgggc ttcactga                                                 18

<210> SEQ ID NO 112
<211> LENGTH: 26
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: HILI, primer (5'-3')

<400> SEQUENCE: 112
tctctgtcaa agaactggct tgtcct                                        26

<210> SEQ ID NO 113
<211> LENGTH: 18
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: HILI, primer (5'-3')

<400> SEQUENCE: 113
ctgtacagtg cggttcat                                                 18

<210> SEQ ID NO 114
<211> LENGTH: 26
<212> TYPE: DNA
<213> ORGANISM: Artificial Sequence
<220> FEATURE:
<223> OTHER INFORMATION: Oligodeoxynucleotide with homology to human
      gene
<220> FEATURE:
<221> NAME/KEY: misc_feature
<223> OTHER INFORMATION: HILI, primer (5'-3')

<400> SEQUENCE: 114
tctctgtcaa agaactggct tgtcct                                        26

<210> SEQ ID NO 115
<211> LENGTH: 23
<212> TYPE: DNA
<213> ORGANISM: Artificial Sequence
<220> FEATURE:
<223> OTHER INFORMATION: Oligodeoxynucleotide with homology to human
      gene

```
<220> FEATURE:
<221> NAME/KEY: misc_feature
<223> OTHER INFORMATION: HILI, primer (5'-3')

<400> SEQUENCE: 115
cggcctgaag gactgagacg tgt                                              23
```